(12) United States Patent
O'Riordan et al.

(10) Patent No.: US 12,031,894 B2
(45) Date of Patent: *Jul. 9, 2024

(54) ANALYTICAL ULTRACENTRIFUGATION FOR CHARACTERIZATION OF RECOMBINANT VIRAL PARTICLES

(71) Applicant: Genzyme Corporation, Cambridge, MA (US)

(72) Inventors: Catherine R. O'Riordan, Cambridge, MA (US); Brenda Burnham, Hopkinton, MA (US)

(73) Assignee: GENZYME CORPORATION, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/513,970

(22) Filed: Nov. 20, 2023

(65) Prior Publication Data
US 2024/0085301 A1  Mar. 14, 2024

Related U.S. Application Data

(63) Continuation of application No. 18/188,176, filed on Mar. 22, 2023, which is a continuation of application No. 16/547,144, filed on Aug. 21, 2019, now Pat. No. 11,639,887, which is a continuation of application No. 15/544,498, filed as application No. PCT/US2016/013947 on Jan. 19, 2016, now Pat. No. 10,429,288.

(60) Provisional application No. 62/105,714, filed on Jan. 20, 2015.

(51) Int. Cl.
*G01N 15/04* (2006.01)
*C12N 7/00* (2006.01)
*G01N 1/40* (2006.01)

(52) U.S. Cl.
CPC .......... *G01N 15/042* (2013.01); *C12N 7/00* (2013.01); *G01N 1/405* (2013.01); *G01N 1/4077* (2013.01); *C12N 2710/10351* (2013.01); *C12N 2750/14151* (2013.01); *G01N 2001/4083* (2013.01); *G01N 2015/045* (2013.01)

(58) Field of Classification Search
CPC .. C07K 2317/92; C07K 14/005; A61K 39/12; C12N 15/86; C12N 2750/14143; C12N 15/864; C12N 2750/14152; G01N 33/68; G01N 2001/4083; C12Q 1/70
See application file for complete search history.

(56) References Cited

U.S. PATENT DOCUMENTS

| | | |
|---|---|---|
| 5,622,856 A | 4/1997 | Natsoulis et al. |
| 6,001,650 A | 12/1999 | Colosi |
| 6,989,264 B2 | 1/2006 | Atkinsin et al. |
| 7,348,134 B2 | 3/2008 | Lingappa |
| 8,137,948 B2 | 3/2012 | Qu et al. |
| 10,429,288 B2 | 10/2019 | O'riordan et al. |
| 11,639,887 B2 | 5/2023 | O'riordan et al. |
| 2009/0017542 A1 | 1/2009 | Colosi |
| 2017/0362608 A1* | 12/2017 | McLaughlin .......... C12N 15/86 |
| 2020/0225139 A1 | 7/2020 | O'riordan et al. |
| 2023/0288308 A1 | 9/2023 | O'riordan et al. |
| 2024/0077402 A1 | 3/2024 | O'riordan et al. |

FOREIGN PATENT DOCUMENTS

| | | | |
|---|---|---|---|
| JP | H11-512926 A | 11/1999 | |
| JP | 2003-511037 A | 3/2003 | |
| WO | WO1997006272 A2 | 2/1997 | |
| WO | WO1997006272 A3 | 2/1997 | |
| WO | WO-0125462 A1 * | 4/2001 | ............. C12N 15/86 |
| WO | WO2001025462 A1 | 4/2001 | |
| WO | WO-2010/148143 A1 | 12/2010 | |
| WO | WO-2014125101 A1 * | 8/2014 | ......... A61K 48/0091 |
| WO | WO-2016118520 A1 | 7/2016 | |

OTHER PUBLICATIONS

Rose JA, Hoggan MD, Shatkin AJ. Nucleic acid from an adeno-associated virus: chemical and physical studies. Proc Natl Acad Sci U S A. Jul. 1966;56(1):86-92. (Year: 1966).*
Cervelli T, Backovic A, Galli A. Formation of AAV single stranded DNA genome from a circular plasmid in *Saccharomyces cerevisiae*. PLoS One. 2011;6(8):e23474. Epub Aug. 10, 2011. (Year: 2011).*
Hauck B, Zhao W, High K, Xiao W. Intracellular viral processing, not single-stranded DNA accumulation, is crucial for recombinant adeno-associated virus transduction. J Virol. Dec. 2004;78(24):13678-86. (Year: 2004).*
Rosenbloom J, Schumaker VN. Analytical Ultracentrifugation of T4R Bacteriophage DNA in Preformed Sucrose Density Gradients. Biochemistry. Nov.-Dec. 1963;2:1206-11. (Year: 1963).*
Hatters DM, Wilson L, Atcliffe BW, Mulhern TD, Guzzo-Pernell N, Howlett GJ. Sedimentation analysis of novel DNA structures formed by homo-oligonucleotides. Biophys J. Jul. 2001;81(1):371-81. (Year: 2001).*

(Continued)

*Primary Examiner* — Rachel B Gill
(74) *Attorney, Agent, or Firm* — MORRISON & FOERSTER LLP

(57) ABSTRACT

Provided herein are methods to characterize preparations of recombinant viral particles using analytical ultracentrifugation. Recombinant viral particles include recombinant adeno-associated viral particles, recombinant adenoviral particles, recombinant lentiviral particles and recombinant herpes simplex virus particles. Variant species of recombinant viral particles including empty capsids and recombinant viral particles with variant genomes (fragmented genomes, aggregates, recombinants) can be identified and quantitated. The methods can be used to characterize preparations of recombinant viral particles regardless of the sequence of the recombinant viral genome or the serotype of the recombinant viral capsid.

30 Claims, 17 Drawing Sheets

(56) References Cited

OTHER PUBLICATIONS

Arisaka, F. (2011). "The Fundamentals of Analytical Ultracentrifugation," Seibutsu Kogaku Kaishi 89(7):375-377, 8 pages (English Translation).
Berkowitz, S. A. et al. (2015). "Characterizing Biopharmaceuticals Using Analytical Ultracentrifugation," Chapter 9 in Biophysical Characterization of Proteins In Developing Biopharmaceuticals:211-260.
Berkowitz, S.A. et al. (Mar. 1, 2007, e-pub. Dec. 20, 2006). "Monitoring the Homogeneity of Adenovirus Preparations (A Gene Therapy Delivery System) Using Analytical Ultracentrifugation," *Anal. Biochem.* 362(1):16-37.
Bo, H. et al. (Jan. 25, 2015, e-pub. Nov. 26, 2014). "Chromatographic Purification of Adenoviral Vectors on Anion-Exchange Resins," *Eur. J. Pharm. Sci.* 67:119-125.
Burnham, B. et al. (Dec. 1, 2015, e-pub. Oct. 15, 2015). "Analytical Ultracentrifugation as an Approach to Characterize Recombinant Adeno-Associated Viral Vectors," *Hum. Gene Ther. Methods* 26(6):228-242.
Cantin, R. et al. (Sep. 30, 2008, e-pub Jul. 31, 2008). Discrimination Between Exosomes and HIV-1: Purification of Both Vesicles From Cell-Free Supernatants, J Immunol Methods. 338(1-2):21-30.
Center, R.J. et al. (Dec. 18, 2001). "Oligomeric Structure Ofvirion-Associated and Soluble Forms of The Simian Immunodeficiency Virus Envelope Protein In The Prefusion Activated Conformation," Proc Natl Acad Sci U SA. 98(26):14877-14882.
Cole, J.L. et al. (2008). "Analytical Ultracentrifugation: Sedimentation Velocity and Sedimentation Equilibrium," Methods *Cell Biol.* 84:143-179.
Cole, J.L. et al. (Dec. 1999). "Analytical Ultracentrifugation as a Contemporary Biomolecular Research Tool," *J. Biomol. Tech.* 10(4):163-176.
Cole, J.L. et al. (Dec. 3, 1996). "Characterization of Human Cytomegalovirus Protease Dimerization by Analytical Centrifugation", *Biochemistry* 35(48):15601-15610.
Collaud, F. et al. (2014). "An Optimized AAV Vector for Liver-Directed Expression of the UGT1A1 Gene in Crigler-Najjar Syndrome towards Clinical Development," Mol. Ther. 22(Supplement 1):S110-S111, No. 286 (2 pages).
Collaud, F. et al. (Mar. 2019). "Preclinical Development of an AAV8-Hugt1a1 Vector for The Treatment of Crigler-Najjar Syndrome," Molecular Therapy-Methods & Clinical Development 12:157-174.
Combined Power of Attorney by Assignee and Statements under 37 CFR §3.73(c) and 3.71 of Genzyme Corporation for U.S. Pat. No. 10,429,288, dated Oct. 17, 2023, 6 pages.
Curriculum Vitae of Jeffrey C. Hansen for U.S. Pat. No. 10,429,288, dated Aug. 22, 2022, Case No. IPR2023-1045, Petitioner Novartis Gene Therapies Inc. and Novartis Pharmaceuticals Corporation, Patent Owner Genzyme Corporation, 8 pages.
Curriculum Vitae of Jeffrey C. Hansen for U.S. Pat. No. 10,429,288, dated Aug. 22, 2022, Case No. IPR2023-1044, Petitioner Novartis Gene Therapies Inc. and Novartis Pharmaceuticals Corporation, Patent Owner Genzyme Corporation, 8 pages.
Dafforn, T. R. (2007). "So How Do You Know You Have a Macromolecular Complex?" Acta Crystallographica Section D: Biological Crystallography D63(1):17-25.
Declaration of Jeffrey C. Hansen, Ph.D. for U.S. Pat. No. 10,429,288, dated Oct. 18, 2023, Case No. IPR2023-1045, Petitioner Novartis Gene Therapies Inc. and Novartis Pharmaceuticals Corporation, Patent Owner Genzyme Corporation, 77 pages.
Declaration of Jeffrey C. Hansen, Ph.D. for U.S. Pat. No. 10,429,288, dated Oct. 11, 2023, Case No. IPR2023-1044, Petitioner Novartis Gene Therapies Inc. and Novartis Pharmaceuticals Corporation, Patent Owner Genzyme Corporation, 81 pages.
Declaration of Steven A. Berkowitz, Ph.D. for U.S. Pat. No. 10,429,288, dated Jun. 30, 2023, Case No. IPR2023-1045, Petitioner Novartis Gene Therapies Inc. and Novartis Pharmaceuticals Corporation, Patent Owner Genzyme Corporation, 132 pages.
Defendants' Initial Invalidity Contentions Regarding U.S. Pat. No. 10,429,288, dated Nov. 6, 2023, C.A. No. 23-554-RGA, Plaintiffs Genzyme Corporation and Aventis, Inc., Defendants Novartis Gene Therapies Inc. and Novartis Pharmaceuticals Corporation, 34 pages.
EPO Third Party Observation mailed on Jul. 30, 2020, for EP Application No. 16703205.1, filed on Jan. 19, 2016, 33 pages.
European Medicines Agency (Jul. 19, 2012) "Assessment Report: Glybera," Committee for Medicinal Products for Human Use (CHMP), Procedure No. EMEA/H/C/002145, 147 pages.
Falabella, J.B. et al. (Jul. 6, 2010). "Characterization of Gold Nanoparticles Modified with Single-Stranded DNA Using Analytical Ultracentrifugation and Dynamic Light Scattering," Langmuir 26(15):12740-12747.
Fumio, A. (2011). "Basis for Ultracentrifugal Analysis," Bioengineering 89(7):11 pages. (English Translation).
Furst, A. (May 1997). "The XL-I Analytical Ultracentrifuge with Rayleigh Interference Optics," *Eur. Biophys. J.* 35(5-6):307-310.
Gao, K. et al. (Jan. 2014). "Empty Virions In AAV8 Vector Preparations Reduce Transduction Efficiency and May Cause Total Viral Particle Dose-Limiting Side Effects," Molecular Therapy—Methods & Clinical Development 1(9), 8 pages.
Goins, W.F. et al. (2014). "Engineering HSV-1 Vectors for Gene Therapy," Chapter 5 in Herpes Simplex Virus: Methods in Molecular Biology, Springer Science+Business Media, New York, 1144:63-79.
Gombold, J. et al. (May 2006). "Lot Release and Characterization Testing of Live-Virus Based Vaccines and Gene Therapy Products Part1," BioProcess Int 4:46-56.
Grange, J. (Jul. 1974). "Determination of the Sedimentation Coefficient of Vaccinia Virus DNA by Analytical Ultracentrifugation," Nucleic Acids Research 1(7):901-906.
Hauck, B. et al. (Jan. 2009, e-pub. Oct. 21, 2008). "Undetectable Transcription of Cap In a Clinical AAV Vector: Implications for Preformed Capsid In Immune Responses", Mol Ther. 17(1):144-152.
Hoque, M. et al. (1999). "Chimeric Virus-Like Particle Formation of Adeno-Associated Virus," Biochemical And Biophysical Research Communications 266(2):371-376.
International Search Report mailed Dec. 4, 2016, for PCT Application No. PCT/US2016/013947, filed Jan. 19, 2016, 3 pages.
Kapranov, P. et al. (Jan. 2012, e-pub. Aug. 29, 2011). "Native Molecular State of Adeno-Associated Viral Vectors Revealed by Single-Molecule Sequencing," *Hum. Gene Ther.* 23(1):46-55.
Lauffer, M.A. (1943). "The Sedimentation Rate of The Infectious Principle of Tobacco Mosaic Virus," J Biol Chem.151(2):627-634.
Lingappa J.R. et al. (2009, e-pub. May 7, 2009). "Assembly of Immature HIV-1 Capsids Using a Cell-Free System," Methods Mol Biol. 485:185-195, 10 pages.
Lingappa, J. R. et al. (Feb. 10, 1997). "A Multistep, ATP-Dependent Pathway for Assembly of Human Immunodeficiency Virus Capsids In a Cell-Free System," The Journal of Cell Biology 136(3):567-581.
Matsushita, T. et al. (1995). "Adeno-Associated Virus Vectors Can Be Efficiently Produced Without Helper Virus," Gene Therapy 5(7):938-945, 13 pages.
McCarty, D.M. (Oct. 2008, e-pub. Aug. 5, 2008). "Self-complementary AAV Vectors; Advances and Applications," Molecular Therapy 16:1648-1656.
McCarty, D.M. et al. (Aug. 2001) "Self-Complementary Recombinant Adeno-Associated Virus (scAAV) Vectors Promote Efficient Transduction Independently of DNA Synthesis," *Gene Ther.* 8(16):1248-1254.
Notice of Filing Date Accorded to Petition and Time for Filing Patent Owner Preliminary Response for U.S. Pat. No. 10,429,288, mailed Jul. 19, 2023, Case No. IPR2023-1045, Petitioner Novartis Gene Therapies Inc. and Novartis Pharmaceuticals Corporation, Patent Owner Genzyme Corporation, 6 pages.
Notice of Filing Date Accorded to Petition and Time for Filing Patent Owner Preliminary Response for U.S. Pat. No. 10,429,288, mailed Jul. 11, 2023, Case No. IPR2023-1044, Petitioner Novartis Gene Therapies Inc. and Novartis Pharmaceuticals Corporation, Patent Owner Genzyme Corporation, 6 pages.

(56) References Cited

OTHER PUBLICATIONS

Ozawa, K. (2007). "Gene Therapy Using A01AV Vectors," Drug Delivery System 22(6):643-650.
Patent Owner's Mandatory Notices Pursuant to 37 C.F.R. Section 42.8 for U.S. Pat. No. 10,429,288, dated Jul. 11, 2023, Case No. IPR2023-1045, Petitioner Novartis Gene Therapies Inc. and Novartis Pharmaceuticals Corporation, Patent Owner Genzyme Corporation, 5 pages.
Patent Owner's Mandatory Notices Pursuant to 37 C.F.R. Section 42.8 for U.S. Pat. No. 10,429,288, dated Jul. 11, 2023, Case No. IPR2023-1044, Petitioner Novartis Gene Therapies Inc. and Novartis Pharmaceuticals Corporation, Patent Owner Genzyme Corporation, 5 pages.
Patent Owner's Power of Attorney for U.S. Pat. No. 10,429,288, dated Jul. 11, 2023, Case No. IPR2023-1045, Petitioner Novartis Gene Therapies Inc. and Novartis Pharmaceuticals Corporation, Patent Owner Genzyme Corporation, 3 pages.
Patent Owner's Power of Attorney for U.S. Pat. No. 10,429,288, dated Jul. 10, 2023, Case No. IPR2023-1044, Petitioner Novartis Gene Therapies Inc. and Novartis Pharmaceuticals Corporation, Patent Owner Genzyme Corporation, 3 pages.
Patent Owner's Preliminary Response for U.S. Pat. No. 10,429,288, dated Oct. 19, 2023, Case No. IPR2023-1045, Petitioner Novartis Gene Therapies Inc. and Novartis Pharmaceuticals Corporation, Patent Owner Genzyme Corporation, 71 pages.
Patent Owner's Preliminary Response for U.S. Pat. No. 10,429,288, dated Oct. 11, 2023, Case No. IPR2023-1044, Petitioner Novartis Gene Therapies Inc. and Novartis Pharmaceuticals Corporation, Patent Owner Genzyme Corporation, 81 pages.
Petition for Inter Partes Review for U.S. Pat. No. 10,429,288, dated Jun. 30, 2023, Case No. IPR2023-1045, Petitioner Novartis Gene Therapies Inc. and Novartis Pharmaceuticals Corporation, Patent Owner Genzyme Corporation, 80 pages.
Petition for Inter Partes Review for U.S. Pat. No. 10,429,288, dated Jun. 30, 2023, Case No. IPR2023-1044, Petitioner Novartis Gene Therapies Inc. and Novartis Pharmaceuticals Corporation, Patent Owner Genzyme Corporation, 80 pages.
Petitioner Novartis Gene Therapies, Inc.'s Power of Attorney and Designation of Lead and Backup Counsel for U.S. Pat. No. 10,429,288, dated Jun. 20, 2023, Case No. IPR2023-1045, Petitioner Novartis Gene Therapies Inc. and Novartis Pharmaceuticals Corporation, Patent Owner Genzyme Corporation, 3 pages.
Petitioner Novartis Gene Therapies, Inc.'s Power of Attorney and Designation of Lead and Backup Counsel for U.S. Pat. No. 10,429,288, dated Jun. 20, 2023, Case No. IPR2023-1044, Petitioner Novartis Gene Therapies Inc. and Novartis Pharmaceuticals Corporation, Patent Owner Genzyme Corporation, 3 pages.
Petitioner Novartis Pharmaceuticals Corporation's Power of Attorney and Designation of Lead and Backup Counsel for U.S. Pat. No. 10,429,288, dated Jun. 20, 2023, Case No. IPR2023-1045, Petitioner Novartis Gene Therapies Inc. and Novartis Pharmaceuticals Corporation, Patent Owner Genzyme Corporation, 3 pages.
Petitioner Novartis Pharmaceuticals Corporation's Power of Attorney and Designation of Lead and Backup Counsel for U.S. Pat. No. 10,429,288, dated Jun. 20, 2023, Case No. IPR2023-1044, Petitioner Novartis Gene Therapies Inc. and Novartis Pharmaceuticals Corporation, Patent Owner Genzyme Corporation, 3 pages.
Petitioner's Exhibit List for U.S. Pat. No. 10,429,288, dated Jun. 30, 2023, Case No. IPR2023-1045, Petitioner Novartis Gene Therapies Inc. and Novartis Pharmaceuticals Corporation, Patent Owner Genzyme Corporation, 4 pages.
Petitioner's Exhibit List for U.S. Pat. No. 10,429,288, dated Jun. 30, 2023, Case No. IPR2023-1044, Petitioner Novartis Gene Therapies Inc. and Novartis Pharmaceuticals Corporation, Patent Owner Genzyme Corporation, 4 pages.
Petitioner's Supplemental Paper and Notice Ranking Petitions for U.S. Pat. No. 10,429,288, dated Jun. 30, 2023, Case No. IPR2023-1045, Petitioner Novartis Gene Therapies Inc. and Novartis Pharmaceuticals Corporation, Patent Owner Genzyme Corporation, 5 pages.
Petitioner's Supplemental Paper and Notice Ranking Petitions for U.S. Pat. No. 10,429,288, dated Jun. 30, 2023, Case No. IPR2023-1044, Petitioner Novartis Gene Therapies Inc. and Novartis Pharmaceuticals Corporation, Patent Owner Genzyme Corporation, 5 pages.
Qu, G. et al. (Mar. 2007, e-pub. Dec. 28, 2006). "Separation of Adeno-Associated Virus Type 2 Empty Particles from Genome Containing Vectors by Anion-Exchange Column Chromatography," *J. Virol. Methods* 140(1-2):183-192.
Ralston, G.B. (1993). "Introduction to Analytical Ultracentrifugation," Beckman Coulter Life Science, vol. 1, 94 pages.
Schmidt, B. et al. (1990). "A Fluorescence Detection System for The Analytical Ultracentrifuge and Its Application to Proteins, Nucleic Acids, Viroids and Viruses," Colloid Polym Sci 268(1):45-54.
Schuck, P. (Mar. 2000). "Size-Distribution Analysis of Macromolecules by Sedimentation Velocity Ultracentrifugation and Lamm Equation Modeling," *Biophys. J.* 78(3):1606-1619.
Segura, M.M. et al. (2011). "Overview of Current Scalable Methods for Purification of Viral Vectors," Methods Mol Biol. 737:89-116, 458 pages.
Segura, M.M. et al. (Apr. 2006, e-pub. Dec. 1, 2005). "Purification and Characterization of Retrovirus Vector Particles by Rate Zonal Ultracentrifugation," J. Viral Methods 133(1):82-91.
Segura, M.M. et al. (Jul. 2013, e-pub. E-pub. Apr. 16, 2013). "New Developments in Lentiviral Vector Design, Production and Purification," *Expert Opin Biol Ther*. 13(7):987-1011.
Sommer, J.M. et al. (Jan. 2003). "Quantification of Adeno-Associated Virus Particles and Empty Capsids by Optical Density Measurement," Mol Ther. 7(1):122-128.
Spies, E. et al. (Mar. 2020). "Assessing The Quality of Adeno-Associated Virus Gene Therapy Vectors by Sedimentation Velocity Analysis," Beckman Coulter Life Sciences, 2 pages.
Steinbach, S. et al. (1997). "Assembly of Adeno-Associated Virus Type 2 Capsids In Vitro," Journal of General Virology 78(6):1453-1462.
U.S. Appl. No. 18/506,853, filed Nov. 10, 2023 for O'Riordan et al. (Not submitted herewith pursuant to the waiver of 37 C.F.R. 1.98(a)(2)(iii) issued by the Office on Sep. 21, 2004).
Van Tricht, E. (Jul. 1, 2013). "Virus Particle Characterization Techniques to Quantify Virus Particle Aggregation and Integrity," Analytical Sciences, MSc Chemistry, Literature Thesis, University Van Amsterdam, 51 pages.
Virag, T. et al. (Aug. 2009). "Producing Recombinant Adeno-Associated Virus In Foster Cells: Overcoming Production Limitations Using a Baculovirus-Insect Cell Expression Strategy," Human Gene Therapy 28(8):807-817.
Wolf, M.W. et al. (Oct. 2011). "Downstream Processing of Cell Culture-Derived Virus Particles," Expert Rev Vaccines 10(10):1451-1475.
Wright, J.F. (Mar. 3, 2014). "Product-Related Impurities in Clinical-Grade Recombinant AAV Vectors: Characterization and Risk Assessment," *Biomedicines* 2(1):80-97.
Xiao, X. et al. (Mar. 1998). "Production of High-Titer Recombinant Adeno-Associated Virus Vectors in the Absence of Helper Adenovirus," *J. Virol.* 72(3):2224-2232.
Xiao-Yu, K. et al. (2008). "Local Lattice Structure Study of the Octahedral (CrO6) 9-Clusters for Cr3+ Ion Doping in a Variety of Oxide Crystals by Simulating the Corresponding EPR and Optical Spectra," The Journal of Physical Chemistry A 112(4):737-743.
Xie, Q. et al. (2002). "The Atomic Structure of Adeno-Associated Virus (AAV-2), a Vector for Human Gene Therapy," Proceedings of the National Academy of Sciences 99(16):10405-10410, 15 pages.
Yang, X. et al. (Feb. 1, 2008). Determination of Particle Heterogeneity and Stability of Recombinant Adenovirus by Analytical Ultracentrifugation in CsCI Gradients, *J. Pharm. Sci.* 97(2):746-763.
Zhao, H. et al. (Feb. 2013). "Overview of Current Methods In Sedimentation Velocity and Sedimentation Equilibrium Analytical Ultracentrifugation," Curr Protoc Protein Sci., 52 pages.

\* cited by examiner

Transgene

Rep ori & Amp

ANALYTICAL ULTRACENTRIFUGATION FOR CHARACTERIZATION OF RECOMBINANT VIRAL PARTICLES

CROSS-REFERENCE TO RELATED APPLICATIONS

This application is a continuation of U.S. patent application Ser. No. 18/188,176, filed Mar. 22, 2023, which is a continuation of U.S. patent application Ser. No. 16/547,144 (now U.S. Pat. No. 11,639,887), filed Aug. 21, 2019, which is a continuation of U.S. patent application Ser. No. 15/544,498 (now U.S. Pat. No. 10,429,288), which adopts the international filing date of Jan. 19, 2016, which is a National Phase application under 35 U.S.C. § 371 of International Application No. PCT/US2016/013947, filed Jan. 19, 2016, which claims priority to U.S. Provisional Application No. 62/105,714, filed Jan. 20, 2015, each of which is incorporated herein by reference in its entirety.

FIELD OF THE INVENTION

The present invention relates to methods to characterize recombinant viral vectors; e.g., recombinant adeno-associated viral (AAV) particles, recombinant adenoviral (rAd) particles, recombinant lentiviral particles and recombinant Herpes simplex viral (rHSV) particles using analytical ultracentrifugation.

BACKGROUND OF THE INVENTION

Recombinant viruses show great promise and utility as a vehicle to deliver therapeutic nucleic acids for gene therapy applications. A number of different recombinant viruses are used in these gene therapy applications based on a number of factors including the size of the nucleic acid to be delivered, the target cell or tissue to deliver the nucleic acid, the need for short or long term expression of the therapeutic nucleic acid, and integration of the therapeutic nucleic acid into the recipient's genome. Examples of viruses used in gene therapy applications include adeno-associated virus (AAV), adenovirus, lentivirus and herpes simplex virus (HSV).

The generation of recombinant viral vectors for the clinic requires an analytical method that monitors drug product quality with regard to homogeneity, purity and consistency of manufacturing, yet to date no method to support such a characterization has been established. Typically, the DNA content of recombinant viral DNA viral vectors is measured by Southern blot analysis using a sequence specific probe. Viral capsids or envelopes may be characterized by immunoassay using an antibody that binds specifically to a capsid or envelope protein of a particular recombinant virus. For example, Steinbach, S et al., (1997) J Gen. Virol., 78:1453-1462 provides an immunoassay for rAAV serotypes. What is needed is a generic assay to characterize recombinant viral preparations regardless of the nucleic acid sequence of the recombinant viral genome or the serotype of the capsid.

All references cited herein, including patent applications and publications, are incorporated by reference in their entirety.

BRIEF SUMMARY OF THE INVENTION

In some aspects, the invention provides methods of characterizing a preparation of recombinant viral particles comprising the steps of a) subjecting the preparation to analytical ultracentrifugation under boundary sedimentation velocity conditions wherein the sedimentation of recombinant viral particles is monitored at time intervals, b) plotting the differential sedimentation coefficient distribution value (C(s)) versus the sedimentation coefficient in Svedberg units (S), and c) integrating the area under each peak in the C(s) distribution to determine the relative concentration of each peak, wherein each peak represents a species of recombinant viral recombinant viral particle.

In some aspects, the invention provides methods to assess vector genome integrity of recombinant viral particles in a preparation of recombinant viral particles comprising a) subjecting the preparation to analytical ultracentrifugation under boundary sedimentation velocity conditions wherein the sedimentation of recombinant viral particles is monitored at time intervals, b) plotting the differential sedimentation coefficient distribution value C(s) versus the sedimentation coefficient in Svedberg units (S), and c) identifying species of recombinant viral particles in the preparation by presence of peaks on the plot corresponding to an S value, wherein the genome size of a particular species of recombinant viral recombinant viral particles is calculated by comparing the S value of the species to a standard curve generated by S values of recombinant viral particles comprising encapsidated viral genomes of known nucleotide sizes. In some embodiments, the methods further comprise integrating the area under each peak in the C(S) distribution to determine the relative concentration of each species of recombinant viral recombinant viral particles.

In some aspects, the invention provides methods to determine the presence of empty capsids or capsid particles comprising variant sized recombinant viral genomes in a preparation of recombinant viral particles comprising the steps of a) subjecting the preparation to analytical ultracentrifugation under boundary sedimentation velocity conditions wherein the sedimentation of recombinant viral particles is monitored at time intervals, and b) plotting the differential sedimentation coefficient distribution value (C(s)) versus the sedimentation coefficient in Svedberg units (S), wherein the presence of one or more peaks other than the peak for full capsid particles comprising intact recombinant viral genomes indicates that presence of capsid particles comprising variant sized genomes and/or empty capsids.

In some aspects, the invention provides, methods of measuring the relative amount empty capsids in a preparation of recombinant viral particles comprising the steps of a) subjecting the preparation to analytical ultracentrifugation under boundary sedimentation velocity conditions wherein the sedimentation of recombinant viral particles is monitored at time intervals, b) plotting the differential sedimentation coefficient distribution value (C(s)) versus the sedimentation coefficient in Svedberg units (S), c) integrating the area under each peak in the C(S) distribution to determine the relative concentration of each species of recombinant viral particles, and d) comparing the amount of recombinant viral particles having an S value corresponding to empty capsid particles to the amount of recombinant viral particles having an S value corresponding to recombinant viral particles comprising intact viral genomes or the total amount of recombinant viral particles in the preparation.

In some aspects, the invention provides methods of measuring the relative amount of capsid particles comprising variant recombinant viral genomes or empty viral capsid particles in a preparation of recombinant viral particles comprising the steps of a) subjecting the preparation to analytical ultracentrifugation under boundary sedimentation velocity conditions wherein the sedimentation of recombinant viral particles is monitored at time intervals, b) plotting the differential sedimentation coefficient distribution value (C(s)) versus the sedimentation coefficient in Svedberg units (S), c) integrating the area under each peak in the C(S) distribution to determine the relative concentration of each species of recombinant viral particles, d) comparing the amount of recombinant viral particles having an S values that do not correspond to recombinant viral particles comprising intact viral genomes to the amount of recombinant viral particles having an S value that corresponds to recombinant viral particles comprising intact viral genomes or to the total amount of recombinant viral particles in the preparation.

In some aspects, the invention provides methods of measuring the relative amount of capsid particles comprising variant recombinant viral genomes in a preparation of recombinant viral particles comprising the steps of a) subjecting the preparation to analytical ultracentrifugation under boundary sedimentation velocity conditions wherein the sedimentation of recombinant viral particles is monitored at time intervals, b) plotting the differential sedimentation coefficient distribution value (C(s)) versus the sedimentation coefficient in Svedberg units (S), c) integrating the area under each peak in the C(S) distribution to determine the relative concentration of each species of recombinant viral particles, d) comparing the amount of recombinant viral particles having an S values that do not correspond to recombinant viral particles comprising intact viral genomes or empty capsid particles to the total amount of recombinant viral particles in the preparation.

In some aspects, the invention provides methods of measuring the relative amount of recombinant viral particles comprising intact viral genomes in a preparation of recombinant viral particles comprising the steps of a) subjecting the preparation to analytical ultracentrifugation under boundary sedimentation velocity conditions wherein the sedimentation of recombinant viral particles is monitored at time intervals, b) plotting the differential sedimentation coefficient distribution value (C(s)) versus the sedimentation coefficient in Svedberg units (S), c) integrating the area under each peak in the C(S) distribution to determine the relative concentration of each species of recombinant viral particles, d) comparing the amount of recombinant viral particles having an S values corresponding to recombinant viral particles comprising intact viral genomes to the amount of recombinant viral particles having an S value corresponding to empty capsid particles, to capsid particles comprising variant recombinant viral genomes, and/or to the total amount of recombinant viral particles in the preparation.

In some aspects, the invention provides, methods of monitoring the removal of empty capsids and/or capsid particles comprising variant recombinant viral genomes during the purification of a preparation of recombinant viral particles, the method comprising removing a sample of the recombinant viral particles from the preparation following one or more steps in the purification process and analyzing the sample for the relative amount of empty capsids and/or capsid particles comprising variant recombinant viral genomes according to the method of any one of claims 5-8, wherein a decrease in the relative amount of empty capsids and/or capsids comprising variant genomes to full capsids indicates removal of empty capsids from the preparation of recombinant viral particles. In some embodiments, the presence of a peak that corresponds to the S value of empty capsid particles indicates the presence of empty capsid particles. In some embodiments, the presence of one or more peaks other than the peak for full capsid particles comprising intact recombinant viral genomes or empty capsid particles indicates that presence of capsid particles comprising variant sized genomes. In some embodiments, the capsid particles comprising variant sized genomes comprise truncated genomes, aggregates, recombinants and/or DNA impurities.

In some aspects, the invention provides methods of determining the heterogeneity of recombinant viral particles in a preparation of recombinant viral particles comprising the steps of a) subjecting the preparation to analytical ultracentrifugation under boundary sedimentation velocity conditions wherein the sedimentation of recombinant viral particles is monitored at time intervals, b) plotting the differential sedimentation coefficient distribution value (C(s)) versus the sedimentation coefficient in Svedberg units (S), wherein the presence of peaks in addition to the peak representing capsids comprising an intact viral genome indicates heterogeneity of recombinant particles in the preparation. In some embodiments, the presence of additional peaks indicates the presence of empty capsid particles and/or recombinant viral particles comprising variant genomes. In some embodiments, the variant genomes are truncated viral genomes, aggregates, recombinants and/or DNA impurities. In some embodiments, the methods further comprise integrating the area under each peak in the C(S) distribution to determine the relative concentration of each species of recombinant viral particles.

In some aspects, the invention provides methods of monitoring the homogeneity of recombinant viral particles during the purification of a preparation of recombinant viral particles, the method comprising removing a sample of the recombinant viral particles from the preparation following one or more steps in the purification process and determining the heterogeneity of recombinant viral particles according to the above method, wherein an increase in the relative amount of recombinant viral particles comprising intact viral genomes indicates an increase in the homogeneity of full viral particles in the preparation of recombinant viral particles.

In some embodiments of the above aspects, sedimentation of recombinant viral particles is monitored by absorbance. In some embodiments, the absorbance is at about 230 nm, 260 nm or 280 nm. In some embodiments, the absorbance is at about 260 nm. In some embodiments, sedimentation of recombinant viral particles is monitored by interference. In some embodiments, the interference is Rayleigh interference.

In some embodiments of the above aspects, the preparation is an aqueous solution. In further embodiments, the aqueous solution comprises a pharmaceutical formulation. In some embodiments, the aqueous solution comprises a buffer. In some embodiments, the buffer is at physiological pH. In some embodiments, the buffer is at physiological osmolality. In some embodiments, the pharmaceutical formulation comprises phosphate buffered saline (PBS). In some embodiments, the PBS has pH of about 7.2 and an osmolality of about 300 mOsm/L. In some embodiments, the monitoring further comprises comparison to a reference sample, wherein the reference sample comprises the aqueous solution without recombinant viral particles.

In some embodiments of the above aspects, the C(S) values are determined by an algorithm that comprises Lamm equation solutions. In some embodiments, the algorithm is the SEDFIT algorithm. In some embodiments, sedimentation is monitored until the recombinant viral particles with the lowest density sediments to the bottom of a sector of an ultracentrifuge; for example, the sector may be a portion of the ultracentrifuge comprising a detection system. In some embodiments, the ultracentrifugation utilizes an ultracentrifuge comprising an ultracentrifuge velocity cell. In some embodiments, sedimentation is monitored until recombinant viral particles sediment to the bottom of ultracentrifuge velocity cell. In some embodiments, sedimentation is monitored until the recombinant viral particles with the lowest density sediments and clears the optical window.

In some embodiments, the radial concentration is recorded for at least about any of 0.5 hours, 0.75 hours, 1.0 hours, 1.5 hours, 2.0 hours, 3.0 hours, 4.0 hours, or 5.0 hours. In some embodiments, the radial concentration is recorded for about 1.0 hour. In some embodiments, the radial concentration is recorded for about 1.2 hours. In some embodiments, the radial concentration is recorded from about 0.5 hours to about 2.0 hours. In some embodiments, the radial concentration is recorded from about 1.0 hours to about 2.0 hours.

In some embodiments of the above aspects, at least 30 scans are used to monitor sedimentation of recombinant viral particles. In some aspects, about 30 scans are used to monitor sedimentation of recombinant viral particles. In other embodiments, about 30 to about 75 scans are used to monitor sedimentation of recombinant viral particles. In other embodiments, about 30 to about 50 scans are used to monitor sedimentation of recombinant viral particles. In other embodiments, about 50 to about 75 scans are used to monitor sedimentation of recombinant viral particles.

In some embodiments of the above aspects, a regularization is applied to a fitting level with a confidence level of F statistic of at least about 0.68. In some embodiments, the regularization is a second derivative regularization. In some embodiments, the regularization is Max entropy regularization. In some embodiments, the regularization is applied to a fitting level with a confidence level of F statistic of about 0.68 to about 0.90. In some embodiments, the regularization is applied to a fitting level with a confidence level of F statistic of about 0.68 to about 0.99. In some embodiments, the regularization is applied to a fitting level with a confidence level of F statistic of about 0.68.

In some embodiments of the above aspects, the following C(S) parameters are held constant: resolution of about 200 S to about 5000 S, S min is about 1 S to about 100 S, S max is about 100 S to about 5000 S, and frictional ratio is about 1.0 or is left to float to a value determined by centrifugation software. In some embodiments, resolution is about 200 S to about 1000 S. In some embodiments, resolution is about 200 S. In some embodiments, S min is about 1. In some embodiments, Smax is about 100 S to about 1000 S. In other embodiments, Smax is about 200 S to about 5000 S. In other embodiments, Smax is about 200 S. In some embodiments, the frictional ratio is left to float to a value determined by centrifugation software. In some embodiments, the frictional ratio is about 1.0. In some embodiments, radial invariant (RI) and time invariant (TI) noise subtractions are applied.

In some embodiments of the above aspects, the sedimentation of recombinant viral particles is monitored about every 10-60 seconds. In some embodiments, sedimentation of recombinant viral particles is monitored (e.g., scanned) about every 10 seconds. In other embodiments, the sedimentation of recombinant viral particles is monitored about every 60 seconds. In some embodiments, the sedimentation velocity of recombinant viral during ultracentrifugation is determined by monitoring the sedimentation of recombinant viral particles once in more than about every 15 seconds, 30 seconds, 45 seconds, 1 minute (60 seconds), 2 minutes, 3 minutes, 4 minutes, 5 minutes, 6 minutes, 7 minutes, 8 minutes, 9 minutes, 10 minutes, 15 minutes, 20 minutes, 25 minutes.

In some embodiments of the above aspects, the boundary sedimentation velocity is performed at about 3,000 rpm to about 20,000 rpm. In some embodiments, the boundary sedimentation velocity is performed at about 3,000 rpm to about 10,000 rpm. In other embodiments, the boundary sedimentation velocity is performed at about 10,000 rpm to about 20,000 rpm. In other embodiments, the boundary sedimentation velocity is performed at about 15,000 rpm to about 20,000 rpm.

In some embodiments of the above aspects, the boundary sedimentation velocity is performed at about 4° C. to about 20° C. In some embodiments, the boundary sedimentation velocity is performed at about 4° C.

In some embodiments of the above aspects, the recombinant viral particle is a recombinant adeno-associated viral (AAV) particle, a recombinant adenovirus particle, a recombinant lentivirus particle or a recombinant herpes simplex viral (HSV) particle. In some embodiments, the recombinant viral particle comprises an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAVrh10 capsid, an AAV11 capsid, an AAV12 capsid, an AAV2R471A capsid, an AAV2/2-7m8 capsid, an AAV DJ capsid, an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, or a mouse AAV capsid rAAV2/HBoV1 (chimeric AAV/human bocavirus virus 1). In some embodiments, the recombinant viral particle comprises an AAV1 ITR, an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV10 ITR, an AAVrh10 ITR, an AAV11 ITR, or an AAV12 ITR. In some embodiments, the AAV capsid comprises a tyrosine mutation or a heparin binding mutation. In other embodiments, the recombinant viral particle is a recombinant adenoviral particle. In some embodiments, the recombinant adenoviral particle comprises an capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral particle comprises a variant of an adenovirus serotype 2 capsid or a variant of an adenoviral serotype 5 capsid. In other embodiments, the recombinant viral particle is a recombinant lentiviral particle. In some embodiments, the recombinant lentiviral particle is pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In other embodiments, the recombinant viral particle is a rHSV particle. In some embodiments, the HSV particle is an HSV-1 particle or an HSV-2 particle.

In some aspects, the invention provides methods for evaluating a process for the production of recombinant viral particles comprising the method of any one of claims 1 to 31, wherein an increase in the relative amount of recombinant viral particles comprising intact viral genomes compared to the relative amount of empty capsid particles and/or recombinant viral capsid particles with variant recombinant viral genomes compared to a reference preparation of recombinant viral particles indicates an improvement in the production of recombinant viral particles. In some embodiments, the recombinant viral particle is a recombinant adeno-associated viral (AAV) particle, a recombinant adenovirus particle, a recombinant lentivirus particle or a recombinant herpes simplex viral (HSV) particle. In some embodiments, the rAAV particles are produced from a producer cell line. In other embodiments, the rAAV particles are produced by triple transfection of i) nucleic acid encoding AAV rep and cap, ii) rAAV vector sequences, and iii) nucleic acid encoding adenovirus helper functions. In other embodiments, the recombinant viral particles are produced by an AAV/HSV hybrid. In other embodiments, the recombinant viral particles are produced from a baculovirus cell. In some embodiments, the recombinant viral particles are produced by transient transfection of nucleic acid encoding AAV vector sequences, AAV rep and cap coding regions, and AAV helper virus functions to a suitable host cell. In some embodiments, the recombinant viral particles are produced by introduction of one or more nucleic acids encoding AAV vector sequences, AAV rep and cap coding regions, and AAV helper virus functions to a suitable host cell, wherein the one or more nucleic acids are introduced to the cell using a recombinant helper virus. In some embodiments, the recombinant helper virus is an adenovirus or a herpes simplex virus. In some embodiments, the recombinant viral particles comprise a self-complementary AAV (scAAV) genome. In some embodiments, the method is used to detect the presence of recombinant viral particles comprising the monomeric form of a scAAV genome or the dimeric form of a scAAV genome.

In some embodiments of the above aspect, the recombinant viral particles are produced by transient transfection of nucleic acid encoding adenovirus vector sequences and adenovirus replication and packaging sequences to a suitable host cell. In other embodiments, the recombinant viral particles are produced by transient transfection of nucleic acid encoding lentivirus vector sequences and/or lentivirus replication and packaging sequences to a suitable host cell. In other embodiments, the recombinant viral particles are produced by transient transfection of nucleic acid encoding HSV vector sequences and/or HSV replication and packaging sequences to a suitable host cell.

In some aspects the invention provides methods for preparing recombinant viral particles with reduced empty capsids and/or recombinant viral particles comprising variant genomes, the method comprising a) culturing host cells under conditions suitable for recombinant viral production, wherein the cells comprise i) nucleic acid encoding a heterologous transgene flanked by at least one AAV ITR, ii) nucleic acid comprising AAV rep and cap coding regions, wherein the nucleic acid comprises a p5 promoter, and iii) nucleic acid encoding AAV helper virus functions; b) lysing the host cells to release recombinant viral particles; c) isolating the recombinant viral particles produced by the host cell; and d) analyzing the recombinant viral particles for the presence of empty capsids and/or recombinant viral particles with variant genomes by analytical ultracentrifugation by the above methods. In some aspects the invention provides methods for preparing recombinant viral particles with reduced empty capsids and/or recombinant viral particles comprising variant genomes, the method comprising a) culturing host cells under conditions suitable for recombinant viral production, wherein the cells comprise i) nucleic acid encoding a heterologous transgene flanked by at least one AAV ITR, ii) nucleic acid comprising AAV rep and cap coding regions, wherein the nucleic acid comprises a mutated p5 promoter wherein rep expression from the p5 promoter is reduced compared to a wild-type p5 promoter, and iii) nucleic acid encoding AAV helper virus functions; b) lysing the host cells to release recombinant viral particles; c) isolating the recombinant viral particles produced by the host cell; and d) analyzing the recombinant viral particles for the presence of empty capsids and/or recombinant viral particles with variant genomes by analytical ultracentrifugation by the above methods. In some embodiments, the p5 promoter is located 3' to the rep and/or cap coding region. In some embodiments, the AAV helper virus functions comprise adenovirus E1A function, adenovirus E1B function, adenovirus E2A function, adenovirus VA function and adenovirus E4 orf6 function.

In some embodiments, of any of the preceding embodiments, the recombinant viral particles have been purified using one or more purification steps.

BRIEF DESCRIPTION OF THE DRAWINGS

(FIG. 1A) A representative scanning profile of boundary sedimentation velocity depicting the absorbance (260 nm) versus the radius (cm) of an AAV2 mixture over a time interval (T) of 1.2 hours. The AAV2 mixture contained empty capsids ("Empty Cap") and full genome capsids ("Intact Vector"). (FIG. 1B) A plot of concentration in units of detection, C(S), versus sedimentation coefficient (Svedberg units, S) showing that AUC can be used to measure the concentration of empty capsids and full genome capsids from an 80%/20% mixture. Each peak is labeled with the particle species and its corresponding sedimentation coefficient (S) and relative abundance (%).

(FIG. 3A) A plot of differential sedimentation coefficient distribution value, c(s), vs sedimentation coefficient in Svedberg units (S), yields the distribution of sedimentation coefficients for a 1:1 mixture of empty and genome-containing capsids generated using interference optical detection. The sedimentation coefficient and relative abundance (%) for each species are labeled. (FIG. 3B) A plot of differential sedimentation coefficient distribution value, c(s), vs sedimentation coefficient in Svedberg units (S), yields the distribution of sedimentation coefficients for a 1:1 mixture of empty and genome-containing capsids generated using absorbance optical detection (260 nm). The sedimentation coefficient and relative abundance (%) for each species are labeled.

(FIG. 6A) A schematic of the AAV2-transgene 2 vector and its 3.4 kb genome. (FIG. 6B) A plot of differential sedimentation coefficient distribution value, c(s), vs sedimentation coefficient in Svedberg units (S), yields the distribution of sedimentation coefficients for a vector preparation produced by the producer cell line method. The sedimentation coefficient and relative abundance (%) for each species are labeled. (FIG. 6C) A plot of differential sedimentation coefficient distribution value, c(s), vs sedimentation coefficient in Svedberg units (S), yields the distribution of sedimentation coefficients for a vector preparation produced by the triple transfection method. The sedimentation coefficient and relative abundance (%) for each species are labeled.

(FIG. 7A) A plot showing the purification of full-genome AAV2-transgene 1 capsids from empty capsids using anion exchange chromatography. Peak fractions corresponding to each species are labeled. (FIG. 7B) A plot of differential sedimentation coefficient distribution value, c(s), vs sedimentation coefficient in Svedberg units (S), yields the distribution of sedimentation coefficients for a vector preparation after elution from the anion exchange column. The sedimentation coefficient and relative abundance (%) for each species are labeled. (FIG. 7C) A plot of differential sedimentation coefficient distribution value, c(s), vs sedimentation coefficient in Svedberg units (S), yields the distribution of sedimentation coefficients for a vector preparation before chromatography. The sedimentation coefficient and relative abundance (%) for each species are labeled.

(FIG. 9A) A plot of differential sedimentation coefficient distribution value, c(s), vs sedimentation coefficient in Svedberg units (S), yields the distribution of sedimentation coefficients for a scAAV9 EGFP vector preparation. Single stranded monomeric (82S) and double stranded dimeric (101S) species are labeled with the corresponding sedimentation coefficients and relative abundance values (%). A schematic of the vector is also provided. (FIG. 9B) Alkaline Southern blot analysis of the DNA from scAAV9 EGFP (lane 1) and single stranded AAV9 EGFP (lane 2) vector capsids. Corresponding bands are labeled as described in the blot legend. 4.2 and 2.4 kb size standards are provided as labeled. (FIG. 9C) A plot of differential sedimentation coefficient distribution value, c(s), vs sedimentation coefficient in Svedberg units (S), yields the distribution of sedimentation coefficients for a single stranded AAV9 EGFP vector preparation. 82S and 99S (full genome) peaks are labeled with the corresponding sedimentation coefficient and relative abundance values (%).

(FIG. 10A) A schematic of the self-complementary scAAV2 EGFP vector, with estimated sedimentation coefficients for the dimeric and monomeric genome species. (FIG. 10B) A plot of differential sedimentation coefficient distribution value, c(s), vs sedimentation coefficient in Svedberg units (S), yields the distribution of sedimentation coefficients for a scAAV2 EGFP vector preparation produced using a "wild-type" helper plasmid with the endogenous p5 promoter driving Rep 78/68 expression ("WT Rep"). Peaks for single stranded monomeric (80 S) and double stranded dimeric (100 S) species are labeled with the corresponding relative abundance values (%). (FIG. 10C) A plot of differential sedimentation coefficient distribution value, c(s), vs sedimentation coefficient in Svedberg units (S), yields the distribution of sedimentation coefficients for a scAAV2 EGFP vector preparation produced using a "wild-type" helper plasmid with the p5 promoter driving Rep 78/68 expression moved downstream of the cap2 sequence ("pHLP Rep"). Peaks for single stranded monomeric (82S) and double stranded dimeric (100 S) species are labeled with the corresponding relative abundance values (%).

(FIGS. 11A and 11B) Plots of differential sedimentation coefficient distribution value, c(s), vs sedimentation coefficient in Svedberg units (S), yield the distribution of sedimentation coefficients for the single stranded AAV5 Factor IX vector (AAV5 hFIX16) containing a cap5 sequence produced with a helper plasmid having an endogenous p5 promoter ("WT Rep," FIG. 11B) or a p5 promoter downstream of the cap5 sequence ("pHLP Rep," FIG. 11A). (FIGS. 11C-11D) Plots of differential sedimentation coefficient distribution value, c(s), vs sedimentation coefficient in Svedberg units (S), yield the distribution of sedimentation coefficients for the single stranded AAV5hSMN vector (AAV5SMN) containing a cap5 sequence produced with a helper plasmid having an endogenous p5 promoter ("WT Rep," FIG. 11D) or a p5 promoter downstream of the cap5 sequence ("pHLP Rep," FIG. 11C).

(FIG. 12A) Southern blot analysis of vector DNA from AAV5SMN preparations made with the pHLP helper plasmid (lane 2) or the WT Rep plasmid (lane 1). 4.6 and 2.4 kb size standards are provided as labeled. (FIG. 12B) Southern blot analysis of vector DNA from AAV5FIX preparations made with the pHLP helper plasmid (lane 1) or the WT Rep plasmid (lane 2). 4.3, 3.0, and 1.9 kb size standards are provided as labeled.

(FIG. 14A) Southern blot analysis using an hFIX transgene-specific probe comparing pHLP Rep (lane 1) and WT Rep (lane 2) vector genomes. (FIG. 14B) Southern blot analysis using a Rep ori/AmpR-specific probe comparing pHLP Rep (lane 1) and WT Rep (lane 2) vector genomes.

(FIG. 15A) Plot of concentration, C(S), versus sedimentation coefficient (S) generated by AUC for an AAV vector with an oversized genome. This genome contains a full-length chicken β-actin (CBA) promoter driving expression of β-phosphodiesterase (ssAAV2/5CBA-βPDE). Peaks for detected species are labeled by observed sedimentation coefficient (S) and relative abundance values (%). (FIG. 15B) Plot of concentration, C(S), versus sedimentation coefficient (S) generated by AUC for an AAV vector with a truncated genome. This genome contains a CBA promoter with a reduced-size intron driving expression of β-phosphodiesterase (AAV5 minCBAPDE6B). Peaks for detected species are labeled by observed sedimentation coefficient (S) and relative abundance values (%).

DETAILED DESCRIPTION

Figure 1A:
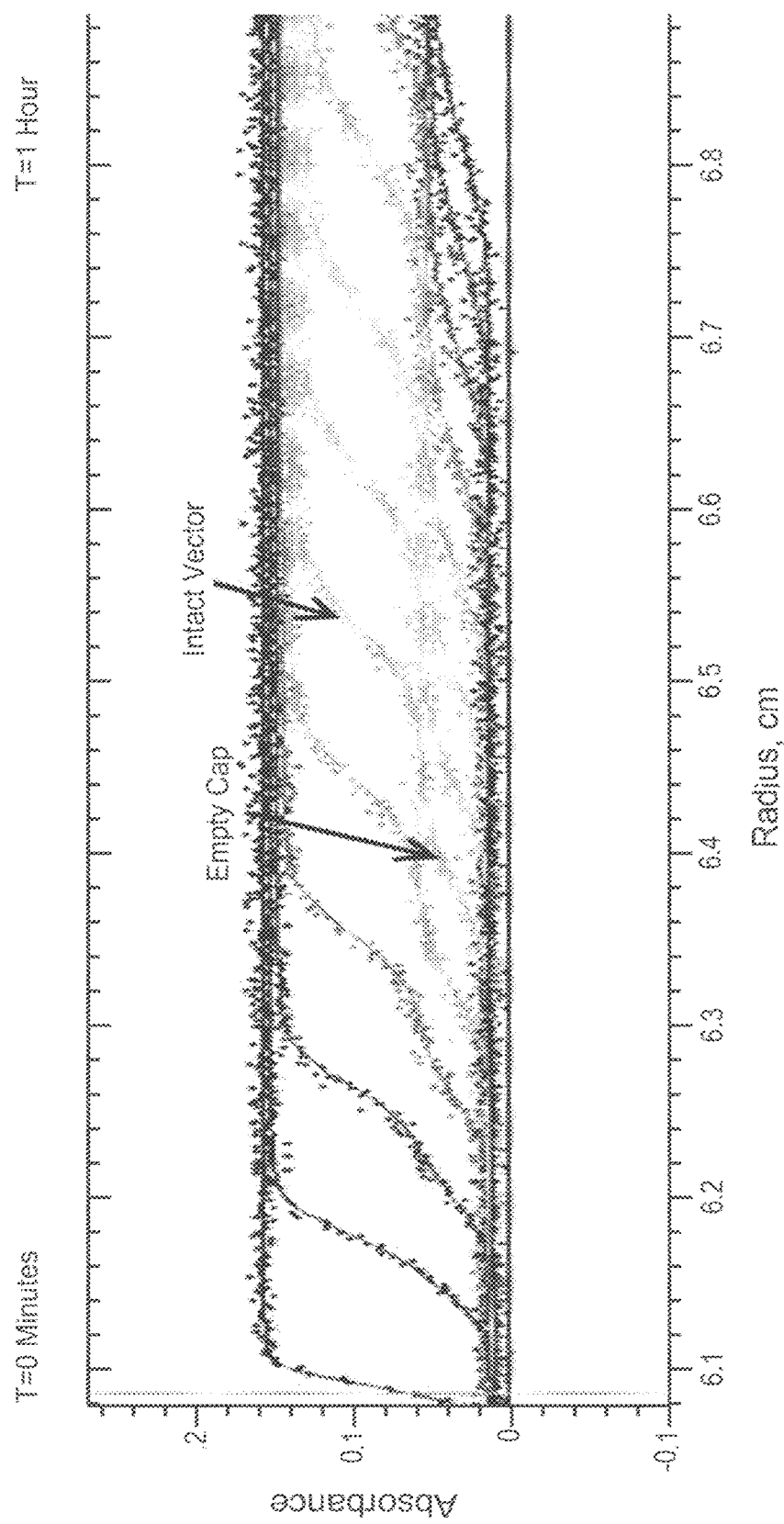
FIGS. 1A and 1B show that analytical ultracentrifugation (AUC) can be used to characterize recombinant viral vector particles.

The present invention provides methods of characterizing preparations of viral particles using analytical ultracentrifugation. By subjecting preparations to analytical ultracentrifugation (AUC) under boundary sedimentation velocity conditions, the sedimentation of viral particles can be monitored at time intervals (e.g., one or more times). The differential sedimentation coefficient distribution value (C(s)) versus the sedimentation coefficient in Svedberg units (S) is then plotted and the area under each peak in the C(s) distribution is integrated to determine the relative concentration of each peak. Each peak represents a species of viral particle reflective of its molecular weight. The species that can be detected by these methods include, but are not limited to, recombinant adeno-associated viral (rAAV) particles, recombinant adenoviral (rAd) particles, recombinant lentiviral particles, and recombinant herpes simplex viral (rHSV) particles. To use rAAV particles as an illustrative example, these methods allow the detection of rAAV species including rAAV capsid particles comprising intact rAAV genomes (e.g., full capsids), empty viral capsids wherein no rAAV genomes have been encapsidated into viral capsids, and rAAV particle variants in which variant rAAV genomes are encapsidated in viral capsids (e.g., particles containing AAV-encapsidated DNA impurities, truncated viral genomes, aggregates, and the like). These methods can be applied to preparations of viral particles regardless of nucleotide sequence of the viral genome or, in the case of recombinant viral particles, the serotype of the recombinant viral capsid. These methods can be applied to rAAV, rAd, recombinant lentivirus and rHSV viral particles.

In some aspects, the invention provides methods to assess vector genome integrity of recombinant viral particles in a preparation of recombinant viral particles by subjecting the preparation to analytical ultracentrifugation under boundary sedimentation velocity conditions wherein the sedimentation of recombinant viral particles is monitored at time intervals (e.g., one or more times). By plotting the differential sedimentation coefficient distribution value C(S) versus the sedimentation coefficient in Svedberg units (S), species of recombinant viral particles in the preparation can be identified by presence of peaks on the plot corresponding to an S value. The genome size of a particular species of recombinant viral particles can be calculated, for example, by comparing the S value of the species to a standard curve generated by S values of recombinant viral particles comprising encapsidated viral genomes of different known size. The vector genomes that can be assessed by these methods include, but are not limited to, recombinant viral capsid particles comprising intact recombinant viral genomes (e.g., full capsids), empty viral capsids wherein no recombinant viral genomes have been encapsidated into viral capsids, and recombinant viral particle variants in which variant recombinant viral genomes (e.g., particles containing AAV-encapsidated DNA impurities, truncated viral genomes, aggregates and the like) are encapsidated in viral capsids. In some embodiments, the viral particles are rAAV, rAd, recombinant lentivirus or rHSV viral particles.

In some embodiments the invention provides methods of determining the heterogeneity of recombinant viral particles (e.g., rAAV, rAd, lentivirus or rHSV particles) in a preparation of recombinant viral particles by AUC under boundary sedimentation velocity conditions wherein the presence of peaks in a plot of C(S) v. S, in addition to the peak representing capsids comprising an intact viral genome, indicates heterogeneity of recombinant viral particles in the preparation. In some embodiments, the relative amounts of each recombinant viral species in the preparation are calculated by integrating the area for each peak in the plot.

In some embodiments of the invention, AUC is used to determine the presence of empty capsids and/or recombinant viral particle variants in a preparation of recombinant viral particles (e.g., rAAV, rAd, lentivirus or rHSV particles), wherein the presence of peak that corresponds to the S value of empty capsid particles and/or recombinant viral particle variants in a plot of C(S) vs. S indicates the presence of empty capsid particles and/or recombinant viral particle variants. In some embodiments, the relative amount of empty capsids and/or recombinant viral particle variants in a preparation of recombinant viral particles is determined by integrating the area under each peak in a plot of C(S) versus S and comparing the amount of recombinant viral particles having an S value corresponding to empty capsid particles and/or recombinant viral particle variants to the amount of recombinant viral particles having an S value corresponding to recombinant viral particles comprising intact viral genomes. In some embodiments, the amount of recombinant viral particles having an S value corresponding to empty capsid particles and/or recombinant viral particle variants is compared to the total amount of all recombinant viral particles in the preparation by integrating and summing and the area under all the peaks of the plot.

In some embodiments, the invention provides methods of monitoring the removal of empty capsids and/or recombinant viral particle variants during the purification of a preparation of recombinant viral particles (e.g., rAAV, rAd, lentivirus or rHSV particles) by using AUC. Samples of the recombinant viral particles from the preparation following one or more steps in the purification process are analyzed for the relative amount of empty capsids and/or recombinant viral particle variants wherein a decrease in the relative amount of empty capsids and/or recombinant viral particle variants to full capsid particles indicates removal of empty capsids and/or recombinant viral particle variants from the preparation of recombinant viral particles.

In some embodiments, the invention provides methods of evaluating processes for the production of recombinant viral particles (e.g., rAAV, rAd, lentivirus or rHSV particles) by AUC. The preparation of recombinant viral particles is analyzed for the presence of intact full viral capsid particles, empty particles and/or recombinant viral particle variants. An increase in the relative amount of recombinant viral particles comprising intact viral genomes compared to the relative amount of empty capsid particles and/or recombinant viral particle variants (e.g., particles containing AAV-encapsidated DNA impurities, truncated viral genomes, aggregates, and the like) compared to a reference preparation of recombinant viral particles (e.g., a standard recombinant viral preparation process) indicates an improvement in the production of recombinant viral particles.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series Methods in Enzymology (Academic Press, Inc.); PCR 2: A Practical Approach (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one inverted terminal repeat sequence (ITR). In some embodiments, the recombinant nucleic acid is flanked by two inverted terminal repeat sequences (ITRs).

A "recombinant AAV vector (recombinant adeno-associated viral vector)" refers to a polynucleotide vector comprising one or more heterologous sequences (i.e., nucleic acid sequence not of AAV origin) that are flanked by at least one AAV inverted terminal repeat sequences (ITR). In some embodiments, the recombinant nucleic acid is flanked by two inverted terminal repeat sequences (ITRs). Such recombinant viral vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of AAV packaging functions and suitable helper functions. A recombinant viral vector can be in any of a number of forms, including, but not limited to, plasmids, linear artificial chromosomes, complexed with lipids, encapsulated within liposomes, and encapsidated in a viral particle, for example, an AAV particle. A recombinant viral vector can be packaged into an AAV virus capsid to generate a "recombinant adeno-associated viral particle (recombinant viral particle)".

An "rAAV virus" or "rAAV viral particle" refers to a viral particle composed of at least one AAV capsid protein and an encapsidated rAAV vector genome.

A "recombinant adenoviral vector" refers to a polynucleotide vector comprising one or more heterologous sequences (i.e., nucleic acid sequence not of adenovirus origin) that are flanked by at least one adenovirus inverted terminal repeat sequence (ITR). In some embodiments, the recombinant nucleic acid is flanked by two inverted terminal repeat sequences (ITRs). Such recombinant viral vectors can be replicated and packaged into infectious viral particles when present in a host cell that is expressing essential adenovirus genes deleted from the recombinant viral genome (e.g., E1 genes, E2 genes, E4 genes, etc.). When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of adenovirus packaging functions. A recombinant viral vector can be in any of a number of forms, including, but not limited to, plasmids, linear artificial chromosomes, complexed with lipids, encapsulated within liposomes, and encapsidated in a viral particle, for example, an adenovirus particle. A recombinant viral vector can be packaged into an adenovirus virus capsid to generate a "recombinant adenoviral particle."

A "recombinant lentivirus vector" refers to a polynucleotide vector comprising one or more heterologous sequences (i.e., nucleic acid sequence not of lentivirus origin) that are flanked by at least one lentivirus terminal repeat sequences (LTRs). In some embodiments, the recombinant nucleic acid is flanked by two lentiviral terminal repeat sequences (LTRs). Such recombinant viral vectors can be replicated and packaged into infectious viral particles when present in a host cell that has been infected with a suitable helper functions. A recombinant lentiviral vector can be packaged into a lentivirus capsid to generate a "recombinant lentiviral particle."

A "recombinant herpes simplex vector (recombinant HSV vector)" refers to a polynucleotide vector comprising one or more heterologous sequences (i.e., nucleic acid sequence not of HSV origin) that are flanked by HSV terminal repeat sequences. Such recombinant viral vectors can be replicated and packaged into infectious viral particles when present in a host cell that has been infected with a suitable helper functions. When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of HSV packaging functions. A recombinant viral vector can be in any of a number of forms, including, but not limited to, plasmids, linear artificial chromosomes, complexed with lipids, encapsulated within liposomes, and encapsidated in a viral particle, for example, an HSV particle. A recombinant viral vector can be packaged into an HSV capsid to generate a "recombinant herpes simplex viral particle."

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as siRNA.

The terms "genome particles (gp)," "genome equivalents," or "genome copies" as used in reference to a viral titer, refer to the number of virions containing the recombinant viral DNA genome or RNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The terms "infection unit (iu)," "infectious particle," or "replication unit," as used in reference to a viral titer, refer to the number of infectious and replication-competent recombinant viral vector particles as measured by the infectious center assay, also known as replication center assay, as described, for example with AAV, in McLaughlin et al. (1988) J. Virol., 62:1963-1973.

The term "transducing unit (tu)" as used in reference to a viral titer, refers to the number of infectious recombinant viral vector particles that result in the production of a functional transgene product as measured in functional assays such as described in Examples herein, or for example regarding AAV, in Xiao et al. (1997) Exp. Neurobiol., 144:113-124; or in Fisher et al. (1996) J. Virol., 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

"AAV helper functions" refer to functions that allow AAV to be replicated and packaged by a host cell. AAV helper functions can be provided in any of a number of forms, including, but not limited to, helper virus or helper virus genes which aid in AAV replication and packaging. Other AAV helper functions are known in the art such as genotoxic agents.

A "helper virus" for AAV refers to a virus that allows AAV (which is a defective parvovirus) to be replicated and packaged by a host cell. A helper virus provides "helper functions" which allow for the replication of AAV. A number of such helper viruses have been identified, including adenoviruses, herpesviruses, poxviruses such as vaccinia and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Examples of adenovirus helper functions for the replication of AAV include E1A functions, E1B functions, E2A functions, VA functions and E4orf6 functions. Baculoviruses available from depositories include *Autographa californica* nuclear polyhedrosis virus.

A preparation of rAAV is said to be "substantially free" of helper virus if the ratio of infectious AAV particles to infectious helper virus particles is at least about $10^2$:1; at least about $10^4$:1, at least about $10^6$:1; or at least about $10^8$:1 or more. In some embodiments, preparations are also free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

As used herein, "differential coefficient distribution value" or "C(S)" is a variant of the distribution of Lamm equation solutions to describe distributions of sedimenting particles; for example during ultracentrifugation.

As used herein, "Svedberg units" refers to a unit for sedimentation rate. The sedimentation rate for a particle of a given size and shape measures how fast the particle sediments. One Svedberg unit is equivalent to $10^{-13}$ seconds. For example, Svedberg units are often used to reflect the rate at which a molecule travels under the centrifugal force of a centrifuge.

As used herein, "sedimentation velocity conditions" or "boundary sedimentation velocity conditions" may refer to any experimental conditions under which a sample solution is subjected to sedimentation velocity analysis. Sedimentation velocity allows the study of particles over a wide range of pH and ionic strength conditions and at temperatures 4 to 40° C. The rate at which the sedimentation boundary moves is a measure of the sedimentation coefficient of the sedimenting species. The sedimentation coefficient depends on the molecular weight (larger particles sediment faster) and also on molecular shape. The minimum width of the sedimentation boundary is related to the diffusion coefficient of the molecule; the presence of multiple species with similar sedimentation coefficients will cause the boundary to be broader than expected on the basis of diffusion alone. Sedimentation velocity conditions may include without limitation any conditions related to the rotor speed, distance between sample and rotor center, temperature, solvent, sample, buffer, ultracentrifugation time, time interval for detection, sector and optical window characteristics, AUC instrumentation (including ultracentrifuge and detection apparatus), equilibrium dialysis of reference solvent, and data analysis algorithms.

As used herein, the term "analytical density gradient sedimentation equilibrium" relates to methods for measuring the buoyant density of a particle, or using differences in buoyant density to separate different species of particles. These methods may use, for example, AUC sedimentation equilibrium techniques. In these methods, a particle solution (e.g., without limitation, a solution of a polypeptide, polynucleotide, or viral capsids) may be subjected to ultracentrifugation in a gradient solvate, such as a cesium chloride or cesium sulfate gradient, until equilibrium with the solvate is attained. At equilibrium, the particle solution will concentrate, or band, at the position in the gradient where the density of the particle is equal to that of the solvate. The position of bands may be used to calculate particle density, or a band may be extracted to isolate a single species of particle.

As used herein, the "SEDFIT algorithm" is an algorithm that allows one to analyze hydrodynamic data such as sedimentation velocity (Schuck (2000) *Biophys. J.*, 78:1606-19). In the SEDFIT algorithm, a grid of sedimentation coefficients across an expected range is created. Sedimentation boundaries are simulated using solutions to the Lamm equation for each sedimentation coefficient, assuming constant particle shape and solvent frictional ratio.

As used herein, the term "F statistic" or "F ratio" refers to the confidence level. This parameter controls the amount of regularization used. It has a different meaning for different ranges: From 0 to 0.5, no regularization is used. Values from 0.5 to 0.999 correspond to probabilities P (confidence levels). From these P-values, the desired chi-square increase allowed for the parsimony constraint of the regularization is calculated with F-statistics. A value of 0.51 will cause very little regularization; values of 0.68 to 0.90 would correspond to commonly used confidence levels (usually, with 50 scans or more the chi-square increase corresponding to a probability of 0.7 is of the order of 0.1%), while values close to 0.99 would cause very high regularization. The relationship of these values with probabilities can be examined using the F-statistics calculator. If numbers >1 are entered, they are taken directly as chi-square ratios (as there are no probabilities >1). For example, a value of 1.1 will result in regularization with 10% chi-square increase.

To "reduce" is to decrease, reduce or arrest an activity, function, and/or amount as compared to a reference. In certain embodiments, by "reduce" is meant the ability to cause an overall decrease of 20% or greater. In another embodiment, by "reduce" is meant the ability to cause an overall decrease of 50% or greater. In yet another embodiment, by "reduce" is meant the ability to cause an overall decrease of 75%, 85%, 90%, 95%, or greater.

A "reference" as used herein, refers to any sample, standard, or level that is used for comparison purposes. For example, when measuring absorbance or refraction of AAV in an aqueous solution, the absorbance or refraction of the solution is compared to the absorbance or refraction of the aqueous solution without AAV (i.e. a reference solution). In other examples, a reference may refer to a standard procedure known in the art. For example, when analyzing a procedure for improved quality of AAV production (e.g., homogeneity), the AAV produced by the candidate procedure is compared to procedures known in the art (i.e. reference procedures).

An "isolated" molecule (e.g., nucleic acid or protein) or cell means it has been identified and separated and/or recovered from a component of its natural environment. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) present in a solution, or by infectivity, or it can be measured in relation to a second, potentially interfering substance present in the source mixture, such as contaminants, including production culture contaminants or in-process contaminants, including helper virus, media components, and the like, as defined below.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise. For example, the phrase "a rAAV particle" includes one or more rAAV particles.

It is understood that aspects and embodiments of the invention described herein include "comprising," "consisting," and/or "consisting essentially of" aspects and embodiments.

III. Analytical Ultracentrifugation

Analytical ultracentrifugation is a means to evaluate the molecular weight and the hydrodynamic and thermodynamic properties of a protein or other macromolecule.

Heterogeneity of a protein or macromolecule by sedimentation velocity over a range of conditions including concentration, temperature, ionic strength, and pH. For example, a protein may be analyzed in a clinically relevant formulation. Use of analytical ultracentrifugation to characterize adenovirus preparations is provided by Berkowitz, S A & Philo J S, (2007) *Anal. Biochem.,* 362:16-37.

In certain aspects, the present invention provides methods of characterizing preparations of viral particles using analytical ultracentrifugation (AUC). For example, in some embodiments, the invention provides methods to assess vector genome integrity of recombinant adeno-associated viral (rAAV) particles in preparations of rAAV particles using AUC to distinguish viral particles with full, intact genomes, empty viral capsids and viral particles with variant (e.g., truncated, aggregates, impurities and the like) viral genomes. In others embodiments, these methods may be applied in a similar way to analyze adenovirus, lentivirus, and herpes simplex virus (HSV) particles. AUC analysis refers to quantitative methods for characterizing the biophysical properties of particles (e.g., polypeptides, polynucleotides, and viral capsids) by measuring their migration through a solvent in a centrifugal field. AUC analysis has been well characterized over many decades and is highly versatile. Because AUC analysis relies upon first-principle hydrodynamic and thermodynamic information, AUC may be applied to determine the biophysical properties of many types of particles across a wide range of particle concentrations and sizes. AUC analysis typically encompasses two basic types of experiment: sedimentation velocity and sedimentation equilibrium. Sedimentation equilibrium analysis yields thermodynamic properties of particles that may be used to measure characteristics such as stoichiometry and association constants. Sedimentation velocity yields hydrodynamic properties of particles that may be used to measure characteristics such as size, shape, and concentration. A feature of AUC analysis of viral preparations is that the same assay conditions may be used to analyze different preparations of viral particles regardless of nucleotide sequence of the viral genome or serotype of the capsid.

Certain aspects of the present disclosure relate to the use of sedimentation velocity analysis to characterize viral capsid properties. In some embodiments, sedimentation velocity analysis uses an ultracentrifuge velocity cell with two sectors in dialysis equilibrium (one for an experimental sample and one for a solvent-only reference sample), each containing two optical windows that allow light to pass through the compartment. Ultracentrifugation applies an angular velocity to the cell and leads to rapid sedimentation of the solute particles towards the bottom of the sector. As sedimentation occurs, solute is depleted near the meniscus at the top of the cell, creating a sedimenting boundary between the depleted region and the sedimenting solute. The rate of movement or migration of the sedimenting boundary is measured by taking measurements that compare the properties of the sample and reference sectors at specific time intervals (for sedimentation velocity, these intervals are typically on the order of minutes). If multiple species of solute are present, this may lead to the formation of multiple sedimenting boundaries, each corresponding to a resolvable species.

Several methods for optically detecting a sedimenting boundary and measuring its rate of movement or migration are known in the art (for reference, see Cole et al. (2008) *Methods Cell Biol.,* 84:143-79). In some embodiments, the reference and sample sectors may be assayed using absorbance detection. In this detection method, the absorbance at a particular wavelength may be measured for the sample and reference sectors at different radial positions within each sector. Alternatively, the time course of absorbance at a single radial position may be measured. Beer's Law provides a mathematical relationship between absorbance and a solute's extinction coefficient.

In some embodiments, the reference and sample sectors may be assayed using interference detection (e.g., Rayleigh interference detection). In the Rayleigh interference detection method, the interference optical system contains two parallel slits. A single, coherent beam of light is split such that it passes through both windows, and then the two beams are re-merged. When these two light waves are merged, they form an interference pattern of alternating light and dark fringes. If the sample and reference samples were to have an identical refractive index, the resulting interference fringes would be perfectly straight. Increasing the concentration of solute increases the solution's refractive index, thereby retarding the sample light beam and causing a vertical fringe shift. By measuring this fringe shift, one may measure the concentration of solute in the sample. Unlike absorbance detection, which measures absolute values for the sample and reference, interference detection measures a relative difference between the sample and reference. However, interference detection yields integrated peaks that are directly proportional to concentration, and it may be used for types of samples that do not absorb significantly. For a reference on using Rayleigh interference optics with AUC, see Furst (1997) *Eur. Biophys. J.* 35:307-10.

Measurement of the rate at which the sedimentation boundary moves may be used to derive many physical properties of solute particles. The rate of the boundary movement determines the sedimentation coefficient, which is based on the mass and shape (frictional coefficient) of the particle. The sedimentation coefficient of a particle, s, refers to the ratio of its velocity to the acceleration applied to it by a centrifugal field. Sedimentation coefficients are expressed in Svedberg units, S (one Svedberg unit is equivalent to $10^{-13}$ seconds). The sedimentation coefficient of a particle or solution of particles depends upon its properties, for example molecular weight (corrected for buoyancy), and the properties of the solvent.

The change in the concentration boundary of a solute over time during ultracentrifugation may be determined using the Lamm equation (Schuck (2000) *Biophys. J.,* 78:1606-19). Briefly, the Lamm equation calculates the change in the concentration boundary of a solute over time in response to the competing forces of sedimentation (which concentrates the solute) and diffusion (which disperses the solute), taking into account the sector-shaped cell and the centrifugal field generated by the rotor. The Lamm equation may be expressed as:

$$\partial c/\partial t = D[(\partial^2 c/\partial r^2) + 1/r(\partial c/\partial r)] - s\omega^2[r(\partial c/\partial r) + 2c] \quad \text{Equation 1:}$$

where c is the solute concentration, D represents the solute diffusion constant, s represents the sedimentation coefficient, $\omega$ represents the angular velocity of the rotor, r is the radius, and t is time.

By fitting raw AUC data to solutions of the Lamm equation, it is possible to determine solute characteristics such as the sedimentation coefficient and the change in concentration distribution. For example, experimentally determined values for the rate of change of a sedimenting boundary may be modeled using the Lamm equation to derive the sedimentation coefficient, molecular mass, or concentration of the solute forming the boundary. Several programs known in the art, such as SEDFIT (Schuck (2000) *Biophys. J.*, 78:1606-19), may be used to model the Lamm equation to AUC data. These programs are also able to apply the Lamm equation to solutions containing multiple solutes or multiple sedimenting boundaries.

One example of a suitable program for the determination of solute characteristics is the SEDFIT algorithm. In some embodiments, the SEDFIT algorithm may be used to calculate a differential coefficient distribution value, or C(S), using AUC data from a solution containing a mixture of particle species (for reference, see Schuck (2000) *Biophys. J.*, 78:1606-19). In the SEDFIT algorithm, a grid of sedimentation coefficients across an expected range is created. Sedimentation boundaries are simulated using solutions to the Lamm equation for each sedimentation coefficient, assuming constant particle shape and solvent frictional ratio. Actual AUC data are then fit to these Lamm solutions to derive the differential coefficient distribution value, or C(S). Many other programs useful for analyzing AUC data may be found in Cole and Hansen (1999) *J. Biomol. Tech.* 10:163-76.

In some embodiments of the invention, recombinant viral particles are highly purified, suitably buffered, and concentrated. In some embodiments, the viral particles are concentrated to at least about any of $1\times10^7$ vg/mL, $2\times10^7$ vg/mL, $3\times10^7$ vg/mL, $4\times10^7$ vg/mL, $5\times10^7$ vg/mL, $6\times10^7$ vg/mL, $7\times10^7$ vg/mL, $8\times10^7$ vg/mL, $9\times10^7$ vg/mL, $1\times10^8$ vg/mL, $2\times10^8$ vg/mL, $3\times10^8$ vg/mL, $4\times10^8$ vg/mL, $5\times10^8$ vg/mL, $6\times10^8$ vg/mL, $7\times10^8$ vg/mL, $8\times10^8$ vg/mL, $9\times10^8$ vg/mL, $1\times10^9$ vg/mL, $2\times10^9$ vg/mL, $3\times10^9$ vg/mL, $4\times10^9$ vg/mL, $5\times10^9$ vg/mL, $6\times10^9$ vg/mL, $7\times10^9$ vg/mL, $8\times10^9$ vg/mL, $9\times10^9$ vg/mL, $1\times10^{10}$ vg/mL, $2\times10^{10}$ vg/mL, $3\times10^{10}$ vg/mL, $4\times10^{10}$ vg/mL, $5\times10^{10}$ vg/mL, $6\times10^{10}$ vg/mL, $7\times10^{10}$ vg/mL, $8\times10^{10}$ vg/mL, $9\times10^{10}$ vg/mL, $1\times10^{11}$ vg/mL, $2\times10^{11}$ vg/mL, $3\times10^{11}$ vg/mL, $4\times10^{11}$ vg/mL, $5\times10^{11}$ vg/mL, $6\times10^{11}$ vg/mL, $7\times10^{11}$ vg/mL, $8\times10^{11}$ vg/mL, $9\times10^{11}$ vg/mL, $1\times10^{12}$ vg/mL, $2\times10^{12}$ vg/mL, $3\times10^{12}$ vg/mL, $4\times10^{12}$ vg/mL, $5\times10^{12}$ vg/mL, $6\times10^{12}$ vg/mL, $7\times10^{12}$ vg/mL, $8\times10^{12}$ vg/mL, $9\times10^{12}$ vg/mL, $1\times10^{13}$ vg/mL, $2\times10^{13}$ vg/mL, $3\times10^{13}$ vg/mL, $4\times10^{13}$ vg/mL, $5\times10^{13}$ vg/mL, $6\times10^{13}$ vg/mL, $7\times10^{13}$ vg/mL, $8\times10^{13}$ vg/mL, $9\times10^{13}$ vg/mL. In some embodiments, the viral particles are concentrated to of about $1\times10^7$ vg/mL to about $1\times10^{13}$ vg/mL, about $1\times10^8$ vg/mL to about $1\times10^{13}$ vg/mL, about $1\times10^9$ vg/mL to about $1\times10^{13}$ vg/mL, about $1\times10^{10}$ vg/mL to about $1\times10^{13}$ vg/mL, about $1\times10^{11}$ vg/mL to about $1\times10^{13}$ vg/mL, about $1\times10^{12}$ vg/mL to about $1\times10^{13}$ vg/mL, about $1\times10^7$ vg/mL to about $1\times10^{12}$ vg/mL, about $1\times10^8$ vg/mL to about $1\times10^{12}$ vg/mL, about $1\times10^9$ vg/mL to about $1\times10^{12}$ vg/mL, about $1\times10^{10}$ vg/mL to about $1\times10^{12}$ vg/mL, about $1\times10^{11}$ vg/mL to about $1\times10^{12}$ vg/mL, about $1\times10^7$ vg/mL to about $1\times10^{11}$ vg/mL, about $1\times10^8$ vg/mL to about $1\times10^{11}$ vg/mL, about $1\times10^9$ vg/mL to about $1\times10^{11}$ vg/mL, about $1\times10^{10}$ vg/mL to about $1\times10^{11}$ vg/mL, about $1\times10^7$ vg/mL to about $1\times10^{10}$ vg/mL, about $1\times10^8$ vg/mL to about $1\times10^{10}$ vg/mL, about $1\times10^9$ vg/mL to about $1\times10^{10}$ vg/mL, about $1\times10^7$ vg/mL to about $1\times10^9$ vg/mL, about $1\times10^8$ vg/mL to about $1\times10^9$ vg/mL, or about $1\times10^7$ vg/mL to about $1\times10^8$ vg/mL.

In some embodiments, viral particles are generated in a suitable host cells and purified. In some embodiments, the viral particles are purified by affinity chromatography. Methods to purify viral particles (e.g., AAV particles, adenovirus particles, lentivirus particles, HSV particles) are known in the art. For example, by use of an antibody of a viral capsid protein or binding ligand of a viral capsid protein immobilized on a chromatography media. Examples of viral capsid affinity chromatographies include but are not limited to AVB affinity chromatography for AAV (GE Healthcare), metal affinity chromatography for adenovirus and HSV, and heparin affinity chromatography for AAV and lentivirus, and the like. Methods to purify adenovirus particles are found, for example, in Bo, H et al., (2014) *Eur. J. Pharm. Sci.* 67C: 119-125. Methods to purify lentivirus particles are found, for example, in Segura M M, et al., (2013) *Expert Opin Biol Ther.* 13(7):987-1011. Methods to purify HSV particles are found, for example, in Goins, W F et al., (2014) *Herpes Simplex Virus Methods in Molecular Biology* 1144:63-79.

In some embodiments, the recombinant viral particles are formulated in a pharmaceutical composition. In related embodiments, the pharmaceutical composition contains a buffer having physiological pH and/or physiological osmolality. A nonlimiting example of a pharmaceutical formulation is phosphate buffered saline (PBS) and in some embodiments, the PBS can be at physiological osmolality (e.g., about pH 7.2 and about 300 mOsm/L). In some embodiments, sample adjustments are made to target concentration by optical density measurement at 260 nm from 0.1 to 1.0. In some examples, this concentration results in reproducible and consistent AUC data. In some examples, concentration of viral particles is adjusted either by direct dilution with PBS or further concentration; for example, by using a centrifugal filter device.

In some embodiments of the invention, sedimentation velocity analytical ultracentrifugation (SV-AUC) analysis is performed using an analytical ultracentrifuge that is capable of characterizing a sample in its native state under biologically relevant solution conditions (e.g., ProteomeLab™ XL-I (Beckman Coulter)). When using the ProteomeLab™ XL-1, sample is loaded into the sample sector of a two sector velocity cell, a vehicle control (e.g., PBS without recombinant viral) is loaded into the corresponding reference sector. The sample is placed in the four-hole rotor and allowed to equilibrate in the instrument until a temperature of about 20° C. and full vacuum are maintained for about one hour. In an exemplary embodiment, sedimentation velocity centrifugation is performed at about 20,000 RPM, about 20° C., and about 0.003 cm radial step setting, with no delay and with no replicates. As noted below, different parameters may be used for centrifugation. In some embodiments, absorbance (260 nm) and/or interference optics (e.g., Rayleigh interference optics) are used to simultaneously record radial concentration as a function of time until the smallest sedimenting component clears the optical window. In some embodiments, the radial concentration is recorded until the sedimenting species with the lowest density clears the sector. In some embodiments, sedimentation is monitored until the recombinant viral particles with the lowest density sediments to the bottom of a sector of an ultracentrifuge. A sector may be a portion of an ultracentrifuge; for example an ultracentrifuge velocity cell. In some embodiments, a sector may be a portion of an ultracentrifuge where samples are detected. In some embodiments, the ultracentrifugation utilizes an ultracentrifuge comprising an ultracentrifuge velocity cell. In some embodiments, is monitored until recombinant viral particles sediment to the bottom of an ultracentrifuge velocity cell. In some embodiments, sedimentation is monitored until the recombinant viral particles with the lowest density sediments and clears the optical window. In some embodiments, the radial concentration is recorded for at least about any of 0.5 hours, 0.75 hours, 1.0 hours, 1.5 hours, 2.0 hours, 3.0 hours, 4.0 hours, or 5.0 hours. In some embodiments, the radial concentration is recorded for between any of about 0.5 hours to about 0.75 hours, about 0.75 hours to about 1.0 hours, about 1.0 hours to about 1.5 hours, about 1.5 hours to about 2.0 hours, about 2 hours to about 3 hours, about 3 hours to about 4 hours, about 4 hours to about 5 hours. In some embodiments, the radial concentration is recorded for about 1.2 hours. Optimizing runs conditions may include, for example, continuing the run until all of the sedimenting species are fully sedimented to the bottom of the sector, with the temperature held constant at 20° C. and a speed between 18,000 rpm and 20,000 rpm. As noted below, other temperatures and speeds may be used.

The percent full capsid is determined by analyzing a multiple of scans (e.g., 75) from each detection method using the SEDFIT continuous size C(S) distribution model. Second ($2^{nd}$) derivative regularization is applied to the fitting. In some embodiments, the confidence level of F statistic is about 0.68. In some embodiments, the confidence level of F statistic is more than about any of 0.68, 0.70, 0.75, 0.80, 0.85, 0.90, 0.95 or 0.99. In some embodiments, the confidence level of F statistic is about 0.68 to about 0.90. In some embodiments, the confidence level of F statistic is about 0.68 to about 0.99. In some embodiments, the following C(S) parameters are held constant: resolution of about 200 S to about 5000 S, S min is about 1 S to about 100 S, S max is about 100 S to about 5000 S, and frictional ratio is about 1.0 or is left to float to a value determined by centrifugation software. In some embodiments, the resolution is about any of 200 S, 300 S, 400 S, 500 S, 600 S, 700 S, 800 S, 900 S, or 1000 S. In some embodiments, the resolution is between any of about 200 S to about 1000 S, 200 S to about 900 S, 200 S to about 800 S, 200 S to about 700 S, 200 S to about 600 S, 200 S to about 500 S, 200 S to about 400 S, 200 S to about 300 S, 300 S to about 1000 S, 300 S to about 900 S, 300 S to about 800 S, 300 S to about 700 S, 300 S to about 600 S, 300 S to about 500 S, 300 S to about 400 S, 400 S to about 1000 S, 400 S to about 900 S, 400 S to about 800 S, 400 S to about 700 S, 400 S to about 600 S, 400 S to about 500 S, 500 S to about 1000 S, 500 S to about 900 S, 500 S to about 800 S, 500 S to about 700 S, 500 S to about 600 S, 600 S to about 1000 S, 600 S to about 900 S, 600 S to about 800 S, 600 S to about 700 S, 700 S to about 1000 S, 700 S to about 900 S, 700 S to about 800 S, 800 S to about 1000 S, 800 S to about 900 S, or 900 S to about 1000 S. In some embodiments, the resolution is about 200 S. In some embodiments, the Smax is about any of 100 S, 200 S, 300 S, 400 S, 500 S, 600 S, 700 S, 800 S, 900 S, or 1000 S. In some embodiments, the Smax is between any of about 100 S to about 1000 S, 100 S to about 900 S, 100 S to about 800 S, 100 S to about 700 S, 100 S to about 600 S, 100 S to about 500 S, 100 S to about 400 S, 100 S to about 300 S, 100 S to about 200 S, 200 S to about 1000 S, 200 S to about 900 S, 200 S to about 800 S, 200 S to about 700 S, 200 S to about 600 S, 200 S to about 500 S, 200 S to about 400 S, 200 S to about 300 S, 300 S to about 1000 S, 300 S to about 900 S, 300 S to about 800 S, 300 S to about 700 S, 300 S to about 600 S, 300 S to about 500 S, 300 S to about 400 S, 400 S to about 1000 S, 400 S to about 900 S, 400 S to about 800 S, 400 S to about 700 S, 400 S to about 600 S, 400 S to about 500 S, 500 S to about 1000 S, 500 S to about 900 S, 500 S to about 800 S, 500 S to about 700 S, 500 S to about 600 S, 600 S to about 1000 S, 600 S to about 900 S, 600 S to about 800 S, 600 S to about 700 S, 700 S to about 1000 S, 700 S to about 900 S, 700 S to about 800 S, 800 S to about 1000 S, 800 S to about 900 S, or 900 S to about 1000 S. In some embodiments, Smax is about 200 S to about 5000 S. In some embodiments, wherein Smax is about 200 S. In some embodiments, the frictional ratio is left to float to a value determined by centrifugation software. In some embodiments, the frictional ratio is about 1.0. In some embodiments, radial invariant (RI) and time invariant (TI) noise subtractions are applied. In some embodiments, the meniscus position is allowed to float, letting the software choose the optimal position. In some embodiments, the frictional ratio is allowed to float, letting the software choose the optimal position. The model fits the data to the Lamm equation, and the resulting size distribution is a "distribution of sedimentation coefficients" that looks like a chromatogram with the area under each peak proportional to concentration in units of Fringes or $OD_{260}$ units. The sedimentation coefficient (in Svedberg units) and the relative concentration (in OD units) are determined for each component in the distribution. In some embodiments, multiple AUC runs are independent assays, and each analysis the following attributes are monitored to ensure quality of results: goodness of fit (rmsd), the ratio of $OD_{260\ nm}$/interference signal in fringes (A260/IF ratio) for each peak, consistency of sedimentation coefficients for each species between runs, and overall quality of the scans.

In some embodiments of the invention, extinction coefficients are used to calculate molar concentration and the actual percent value of the intact vector peak from absorbance data. Molar absorbance extinction coefficients for both empty capsids ($\mathcal{E}_{260}/_{capsid}$=3.72e6) and intact vector ($\mathcal{E}_{260}/_{vector}$=3.00e7) can be calculated based on published formulae (Sommer et al. (2003) *Mol Ther.*, 7:122-8). Extinction coefficients are available for empty capsid and intact vector peaks. The C(S) values can be determined using the SEDFIT algorithm described by Schuck (2000) *Biophys. J.*, 78:1606-19. Molar concentration of both intact vector and empty capsid can be calculated using Beer's Law and the percentage of full capsid are calculated from these values. In some embodiments, values are reported in terms of the percentage of full capsid.

In some embodiments, it is not possible to determine empirically the extinction coefficient of particular species of recombinant viral particles (e.g., viral particles with fragmented genomes of unknown size and sequence). A relationship between S value and genome size may be established by analyzing recombinant viral vector preps with encapsidated viral genomes of known nucleotide size and a corresponding S value are determined as described herein. The calculated S values can be plotted to generate a standard curve to which recombinant viral species of unknown molecular weight or genome size can be compared to determine the molecular weight of the unknown species.

In some aspects, the invention provides methods of characterizing a preparation of recombinant viral particles (e.g., rAAV, rAd, lentiviral, or rHSV particles) comprising the steps of a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value (C(s)) versus the sedimentation coefficient in Svedberg units (S), c) integrating the area under each peak in the C(s) distribution to determine the relative concentration of each peak, wherein each peak represents a species of recombinant viral particle. In some embodiments, the species of recombinant viral particle identified by the methods of the invention include, but are not limited to; full recombinant viral particles comprising intact recombinant viral genomes, empty recombinant viral capsid particles, and recombinant viral particles comprising variant recombinant viral genomes. In some embodiments the variant genomes are smaller than the intact recombinant viral genome (e.g., truncated genomes). In some embodiments, the variant genomes are larger than the intact recombinant viral genome (e.g., aggregates, recombinants, etc.). In some embodiments, the invention provides methods to assess vector genome integrity of recombinant viral particles in a preparation of recombinant viral particles comprising a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value C(s) versus the sedimentation coefficient in Svedberg units (S), c) identifying species of recombinant viral particles in the preparation by presence of peaks on the plot corresponding to an S value, wherein the genome size of a particular species of recombinant viral particles is calculated by comparing the S value of the species to a standard curve generated by S values of recombinant viral particles comprising encapsidated viral genomes of different known size. In some embodiments, the methods further comprise integrating the area under each peak in the C(S) distribution to determine the relative concentration of each species of recombinant viral particles. In some embodiments, the sedimentation of recombinant viral particles is monitored at one time interval. In some embodiments, the sedimentation of recombinant viral particles is monitored at more than one time interval.

In some embodiments of the invention, the sedimentation of recombinant viral particles (e.g., rAAV, rAd, lentiviral, or rHSV particles) is monitored by measuring optical density or absorbance at about 260 nm. Means of measuring absorbance are known in the art. In some embodiments, an ultracentrifuge used for AUC is equipped with means for measuring absorbance. In other embodiments, the sedimentation of recombinant viral particles is monitored by interference. In some embodiments, the sedimentation of recombinant viral particles is monitored by Rayleigh interference. Means of measuring interference are known in the art (Furst (1997) *Eur. Biophys. J.* 35:307-10). In some embodiments, an ultracentrifuge used for AUC is equipped with means for measuring interference. In some embodiments, the sedimentation of recombinant viral particles is monitored by both absorbance and interference. In some embodiments, the absorbance and/or interference are measured using a reference standard. In some embodiments, the reference standard matches the solution of the recombinant viral preparation with the exception that the recombinant viral is not present. For example, the recombinant viral preparation may comprise recombinant viral in a buffer such as phosphate buffered saline. In this example, the reference standard may be phosphate buffered saline without recombinant viral particles.

In some embodiments of the invention, the preparation of viral particles is in a pharmaceutical formulation. Such formulations are well known in the art (see, e.g., Remington's Pharmaceutical Sciences, 15th Edition, pp. 1035-1038 and 1570-1580). Such pharmaceutical formulations can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical formulation may further comprise additional ingredients, for example preservatives, buffers, tonicity agents, antioxidants and stabilizers, nonionic wetting or clarifying agents, viscosity-increasing agents, and the like. In some embodiments of the invention the pharmaceutical formulation comprises phosphate buffered saline.

In some embodiments of the invention, the sedimentation velocity of viral particles during ultracentrifugation is determined by monitoring the sedimentation of viral particles continuously during ultracentrifugation. It is within the purview of the skilled artisan to optimize the parameters of AUC for different types of viral particles. Without wishing to be bound to theory, a range of AUC settings that allows the analysis of both AAV and adenovirus particles should enable the analysis of other viral particles including lentivirus and HSV since the size of HSV and lentiviral particles is between that of AAV and adenovirus particles. In some embodiments, data acquisition for rAAV, rHSV, lentiviral, and/or rAd particles is performed with an AUC speed of between about 3,000 and about 20,000 rpm. In some embodiments, data analysis for rAAV, HSV, lentiviral, and/or adenoviral particles is performed with an $S_{min}$ of about 1 S and an $S_{max}$ of about 1000 S. In some embodiments, data analysis for rAAV, rHSV, lentiviral, and/or rAd particles is performed with a resolution of about 200 S to about 1,000 S. In some embodiments, the resolution is about any of 200 S, 300 S, 400 S, 500 S, 600 S, 700 S, 800 S, 900 S, or 1000 S. In some embodiments, the resolution is between any of about 200 S to about 1000 S, 200 S to about 900 S, 200 S to about 800 S, 200 S to about 700 S, 200 S to about 600 S, 200 S to about 500 S, 200 S to about 400 S, 200 S to about 300 S, 300 S to about 1000 S, 300 S to about 900 S, 300 S to about 800 S, 300 S to about 700 S, 300 S to about 600 S, 300 S to about 500 S, 300 S to about 400 S, 400 S to about 1000 S, 400 S to about 900 S, 400 S to about 800 S, 400 S to about 700 S, 400 S to about 600 S, 400 S to about 500 S, 500 S to about 1000 S, 500 S to about 900 S, 500 S to about 800 S, 500 S to about 700 S, 500 S to about 600 S, 600 S to about 1000 S, 600 S to about 900 S, 600 S to about 800 S, 600 S to about 700 S, 700 S to about 1000 S, 700 S to about 900 S, 700 S to about 800 S, 800 S to about 1000 S, 800 S to about 900 S, or 900 S to about 1000 S. In some embodiments, the resolution is about 200 S. data analysis for rAAV, rHSV, lentiviral, and/or rAd particles is performed with an Smax of about any of 100 S, 200 S, 300 S, 400 S, 500 S, 600 S, 700 S, 800 S, 900 S, or 1000 S. In some embodiments, the Smax is between any of about 100 S to about 1000 S, 100 S to about 900 S, 100 S to about 800 S, 100 S to about 700 S, 100 S to about 600 S, 100 S to about 500 S, 100 S to about 400 S, 100 S to about 300 S, 100 S to about 200 S, 200 S to about 1000 S, 200 S to about 900 S, 200 S to about 800 S, 200 S to about 700 S, 200 S to about 600 S, 200 S to about 500 S, 200 S to about 400 S, 200 S to about 300 S, 300 S to about 1000 S, 300 S to about 900 S, 300 S to about 800 S, 300 S to about 700 S, 300 S to about 600 S, 300 S to about 500 S, 300 S to about 400 S, 400 S to about 1000 S, 400 S to about 900 S, 400 S to about 800 S, 400 S to about 700 S, 400 S to about 600 S, 400 S to about 500 S, 500 S to about 1000 S, 500 S to about 900 S, 500 S to about 800 S, 500 S to about 700 S, 500 S to about 600 S, 600 S to about 1000 S, 600 S to about 900 S, 600 S to about 800 S, 600 S to about 700 S, 700 S to about 1000 S, 700 S to about 900 S, 700 S to about 800 S, 800 S to about 1000 S, 800 S to about 900 S, or 900 S to about 1000 S. In some embodiments, Smax is about 200 S to about 5000 S. In some embodiments, wherein Smax is about 200 S. In some embodiments, radial invariant (RI) and time invariant (TI) noise subtractions are applied. In some embodiments, the meniscus position is allowed to float, letting the software choose the optimal position. In some embodiments, the frictional ratio is allowed to float, letting the software choose the optimal position. In some embodiments, data analysis for rAAV and/or adenoviral particles is held constant at 1. In some embodiments, data analysis for rAAV, HSV, lentiviral, and/or adenoviral particles is allowed to float by using the FIT command with a value optimized using non-linear regression.

With respect to recombinant viral particles (e.g., rAAV, rAd, lentiviral, or rHSV particles), in some embodiments, the sedimentation velocity of recombinant viral during ultracentrifugation is determined by monitoring (e.g., scanning) the sedimentation of recombinant viral particles once in more than about every 15 seconds, 30 seconds, 45 seconds, 1 minute (60 seconds), 2 minutes, 3 minutes, 4 minutes, 5 minutes, 6 minutes, 7 minutes, 8 minutes, 9 minutes, 10 minutes, 15 minutes, 20 minutes, 25 minutes. Scans may be continuously acquired without delay as quickly as the optical systems allow. Interference scans are rapid, and a single scan is complete in ~10-15 seconds, while absorbance scans require ~60 seconds. When dual detection is used the speed of scan acquisition for both are determined by the absorbance system. In some embodiments of the invention, more than about 5, 10, 15, 20, 25, 30, 35, 40, 45, 50, 55, 60, 65, 70, 75, 80, 85, 90, 95, or 100 scans are used to monitor sedimentation of recombinant viral particles during ultracentrifugation. In some embodiments, a minimum of 30 scans is required for analysis, and scans are collected until the sedimentation process is complete. In some embodiments, the sedimentation process may typically be described by between 40 and 75 scans. In some embodiments, the sedimentation velocity of recombinant viral particles is determined based on about 75 scans. In some embodiments, the sedimentation velocity of recombinant viral particles is determined based on about 55 scans to about 75 scans. In some embodiments, the sedimentation velocity of recombinant viral particles is determined based on about 55 scans to about 60 scans. In some embodiments, the sedimentation velocity of recombinant viral particles is determined based on about 60 scans to about 75 scans. In some embodiments, the sedimentation velocity of recombinant viral particles is determined based on about 60 scans to about 70 scans. In some embodiments, the sedimentation velocity of recombinant viral particles is determined based on multiple ultracentrifugations (runs). In some embodiments, the sedimentation velocity of recombinant viral particles is determined based on any of 1, 2, 3, 4, 5, 6, 7, 8, 9, 10 or more ultracentrifugation runs. In some embodiments, the sedimentation velocities are used to determine C(S) values using the SEDFIT algorithm. In some embodiments, a second derivative regularization is applied to a fitting level with a confidence level of F statistic of about 0.68. In some embodiments, the following C(S) parameters are held constant: resolution 100 S to about 200 S, S min is about 1, S max is about 200 S to 300 S, and frictional ratio is about 1.0 to 1.2 S. In some embodiments, radial invariant (RI) and time invariant (TI) noise subtractions are applied.

In some embodiments of the invention, the boundary sedimentation velocity of recombinant viral particles (e.g., rAAV, rAd, lentiviral, or rHSV particles) in a preparation of recombinant viral particles by ultracentrifuging the preparation of recombinant viral particles at more than about any of 5,000 rpm; 10,000 rpm; 15,000 rpm; 20,000 rpm; 25,000 rpm; 30,000 rpm; 35,000 rpm; 40,000 rpm; 45,000 rpm; or 50,000 rpm. In some embodiments, the ultracentrifugation is run at between any of about 5,000 rpm and about 50,000 rpm; about 10,000 rpm and about 50,000 rpm; about 15,000 rpm and about 50,000 rpm; about 20,000 rpm and about 50,000 rpm; about 25,000 rpm and about 50,000 rpm; about 30,000 rpm and about 50,000 rpm; about 35,000 rpm and about 50,000 rpm; about 40,000 rpm and about 50,000 rpm; about 45,000 rpm and about 50,000 rpm; about 5,000 rpm and about 45,000 rpm; about 10,000 rpm and about 45,000 rpm; about 15,000 rpm and about 45,000 rpm; about 20,000 rpm and about 45,000 rpm; about 25,000 rpm and about 45,000 rpm; about 30,000 rpm and about 45,000 rpm; about 40,000 rpm and about 45,000 rpm; about 5,000 rpm and about 40,000 rpm; about 10,000 rpm and about 40,000 rpm; about 15,000 rpm and about 40,000 rpm; about 20,000 rpm and about 40,000 rpm; about 25,000 rpm and about 40,000 rpm; about 30,000 rpm and about 40,000 rpm; about 35,000 rpm and about 40,000 rpm; about 5,000 rpm and about 35,000 rpm; about 10,000 rpm and about 35,000 rpm; about 15,000 rpm and about 35,000 rpm; about 20,000 rpm and about 35,000 rpm; about 25,000 rpm and about 35,000 rpm; about 30,000 rpm and about 35,000 rpm; about 5,000 rpm and about 30,000 rpm; about 10,000 rpm and about 30,000 rpm; about 15,000 rpm and about 30,000 rpm; about 20,000 rpm and about 30,000 rpm; about 25,000 rpm and about 30,000 rpm; about 5,000 rpm and about 25,000 rpm; about 10,000 rpm and about 25,000 rpm; about 20,000 rpm and about 25,000 rpm; about 5,000 rpm and about 20,000 rpm; about 10,000 rpm and about 20,000 rpm; about 15,000 rpm and about 20,000 rpm; about 5,000 rpm and about 15,000 rpm; about 10,000 rpm and about 15,000 rpm; or about 5,000 rpm and about 10,000 rpm. In some embodiments of the invention, the boundary sedimentation velocity of recombinant viral particles in a preparation of recombinant viral particles by ultracentrifuging the preparation of recombinant viral particles at about 20,000 rpm. In some embodiments of the invention, the boundary sedimentation velocity of recombinant viral particles in a preparation of recombinant viral particles by ultracentrifuging the preparation of recombinant viral particles at about 15,000 rpm to about 20,000 rpm.

In some embodiments of the invention, the boundary sedimentation velocity of recombinant viral particles in a preparation of recombinant viral particles (e.g., rAAV, rAd, lentiviral, or rHSV particles) by ultracentrifuging the preparation of recombinant viral particles at about or more than 4° C., 10° C., 15° C., 20° C., 25° C., or 30° C. In some embodiments, the ultracentrifugation is run as between any of about 4° C. and about 30° C., about 4° C. and about 25° C., about 4° C. and about 20° C., about 4° C. and about 15° C., about 4° C. and about 10° C., about 10° C. and about 30° C., about 10° C. and about 25° C., about 10° C. and about 20° C., about 10° C. and about 15° C., about 15° C. and about 30° C., about 15° C. and about 25° C., about 15° C. and about 20° C., about 20° C. and about 30° C., or about 20° C. and about 25° C. In some embodiments, the boundary sedimentation velocity of recombinant viral particles in a preparation of recombinant viral particles by ultracentrifuging the preparation of recombinant viral particles at about 20° C. In some embodiments, the boundary sedimentation velocity of recombinant viral particles in a preparation of recombinant viral particles by ultracentrifuging the preparation of recombinant viral particles at about 15° C. to about 20° C.

As disclosed herein, numerous types of recombinant viral particles may be analyzed by the methods of the present disclosure (e.g., AAV, adenoviral, lentiviral, and/or HSV particles). Suitable ultracentrifugation conditions, analysis algorithms, and other parameters may be determined empirically through methods known in the art. Exemplary parameters for AAV, adenoviral, lentiviral, and HSV particles, along with guidance for the selection of specific parameter options, are provided without limitation in Table 1 below.

TABLE 1

Exemplary parameters for AAV, adenoviral, lentiviral, and HSV particles.

| | AAV | Ad | Lentivirus | HSV |
|---|---|---|---|---|
| Exemplary buffers | Phosphate based buffer at physiologic pH, and physiologic osmolality ~300 mOsM/L | Phosphate based buffer at physiologic pH, and physiologic osmolality ~300 mOsM/L L | Phosphate based buffer at physiologic pH, and physiologic osmolality ~300 mOsM/L | Phosphate based buffer at physiologic pH, and physiologic osmolality ~300 mOsM/L |
| Exemplary algorithms for determining C(S) | Any algorithm using Lamm equation solutions; e.g., SEDFIT C(S) | Any algorithm using Lamm equation solutions; e.g., SEDFIT C(S) | Any algorithm using Lamm equation solutions; e.g., SEDFIT C(S) | Any algorithm using Lamm equation solutions; e.g., SEDFIT C(S) |
| Exemplary number of scans (minimum, maximum, ranges) | 30-999 *excess scans can always be collected and then excluded from analysis (such as skip every other scan)-scans that occur after complete sedimentation of virus can be excluded | 30-999 | 30-999 | 30-999 |
| Exemplary confidence level of the F statistic | F = 0.68 | F = 0.68 | F = 0.68 | F = 0.68 |
| Exemplary ranges for Smin | 1-100S | 1-100S | 1-100S | 1-100S |
| Exemplary ranges for Smax | 100-1000S | 100-5000S | 100-5000S | 100-5000S |
| Exemplary ranges for resolution | *Resolution depends on S Max 200S-1000S | 200-5000S | 200-5000S | 200-5000S |
| Exemplary frictional ratio | Use the FIT command to determine frictional ratio. Since AAV is ~spherical, in embodiments, 1 may be used as the frictional ratio. | Use FIT command to determine frictional ratio or set at 1. | Use FIT command to determine frictional ratio | Use FIT command to determine frictional ratio |
| Exemplary ranges for AUC speed | 10,000-20,000 rpm | 3,000-10,000 rpm | 3,000-10,000 rpm | 3,000-10,000 rpm |
| Exemplary absorbances for monitoring sedimentation of viral particles | 260 nm 280 nm 230 nm | 260 nm 280 nm 230 nm | 260 nm 280 nm 230 nm | 260 nm 280 nm 230 nm |
| Exemplary methods for monitoring sedimentation of viral particles | IF Absorbance | IF Absorbance | IF Absorbance | IF Absorbance |
| Radial invariant (RI) and time invariant (TI) noise subtractions, alternative subtractions/calculations | Ti and RI noise correction required for interference detection. May or may not be used with absorbance detection | Ti and RI noise correction required for interference detection. May or may not be used with absorbance detection | Ti and RI noise correction required for interference detection. May or may not be used with absorbance detection | Ti and RI noise correction required for interference detection. May or may not be used with absorbance detection |

TABLE 1-continued

Exemplary parameters for AAV, adenoviral, lentiviral, and HSV particles.

| | AAV | Ad | Lentivirus | HSV |
|---|---|---|---|---|
| Scanning frequency | *when using absorbance detection system, limited by speed of absorbance scan (~60 Seconds)-scan as fast as system allows with no delay IF only: collect every 10-60 seconds (10-60 second delay) | Scan with no delay through scan with 60 second delay | Scan with no delay through scan with 60 second delay | Scan with no delay through scan with 60 second delay |
| Temperature ranges | 4° C.-20° C. | 4° C.-20° C. | 4° C. -20° C. | 4° C.-20° C. |

In some aspects, the invention provides methods to determine the presence of empty capsids in a preparation of recombinant viral particles (e.g., rAAV, rAd, lentiviral, or rHSV particles) comprising the steps of a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value (C(s)) versus the sedimentation coefficient in Svedberg units (S), wherein the presence of peak that corresponds to the S value of empty capsid particles indicates that presence of empty capsid particles. In some embodiments, the invention provides methods of measuring the relative amount empty capsids in a preparation of recombinant viral particles comprising the steps of a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value (C(s)) versus the sedimentation coefficient in Svedberg units (S), c) integrating the area under each peak in the C(S) distribution to determine the relative concentration of each species of recombinant viral particles, d) comparing the amount of recombinant viral particles having an S value corresponding to empty capsid particles to the amount of recombinant viral particles having an S value corresponding to recombinant viral particles comprising intact viral genomes. In some embodiments, the amount of recombinant viral particles having an S value corresponding to empty capsid particles is compared to the total amount of all recombinant viral particles in the preparation by integrating all peaks on the plot of C(S) vs. S.

In some aspects, the invention provides methods to determine the presence of recombinant viral particle variants in a preparation of recombinant viral particles (e.g., rAAV, rAd, lentiviral, or rHSV particles) comprising the steps of a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value (C(s)) versus the sedimentation coefficient in Svedberg units (S), wherein the presence of peak that corresponds to the S value that differs from the S value of recombinant viral capsid particles comprising a full intact recombinant viral genome indicates that presence of recombinant viral particle variants. In some embodiments, the invention provides methods of measuring the relative amount recombinant viral particle variants in a preparation of recombinant viral particles comprising the steps of a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value (C(s)) versus the sedimentation coefficient in Svedberg units (S), c) integrating the area under each peak in the C(S) distribution to determine the relative concentration of each species of recombinant viral particles, d) comparing the amount of recombinant viral particles having an S value corresponding to empty capsid particles to the amount of recombinant viral particles having an S value corresponding to recombinant viral particles comprising intact viral genomes. In some embodiments, the amount of recombinant viral particles having an S value that differs from the S value of recombinant viral capsid particles comprising a full intact recombinant viral genome is compared to the total amount of all recombinant viral particles in the preparation by integrating all peaks on the plot of C(S) vs. S. In some embodiments, the recombinant viral particle variants comprise recombinant viral genomes that are smaller (e.g., truncated) or larger than the full length intact viral genome. Other viral-encapsidated DNA impurities can also be detected.

In some embodiments, the invention provides methods of monitoring the removal of empty capsids and/or recombinant viral particles with variant genomes during the purification of a preparation of recombinant viral particles (e.g., rAAV, rAd, lentiviral, or rHSV particles) the method comprising removing a sample of the recombinant viral particles from the preparation following one or more steps in the purification process and analyzing the sample for the relative amount of empty capsids using AUC as described herein. A decrease in the relative amount of empty capsids and/or recombinant viral particles comprising variant genomes to full capsids indicates removal of empty capsids from the preparation of recombinant viral particles.

In some embodiments, the invention provides methods of determining the heterogeneity of recombinant viral particles in a preparation of recombinant viral particles (e.g., rAAV, rAd, lentiviral, or rHSV particles) comprising the steps of a) subjecting the preparation to analytical ultracentrifugation under boundary sedimentation velocity conditions wherein the sedimentation of recombinant viral particles is monitored at time intervals (e.g., one or more times), b) plotting the differential sedimentation coefficient distribution value (C(s)) versus the sedimentation coefficient in Svedberg units (S), wherein the presence of peaks in addition to the peak representing capsids comprising an intact viral genome indicates heterogeneity of recombinant viral particles in the preparation. In some embodiments, the species of recombinant viral particle identified by the methods of the invention include, but are not limited to full recombinant viral particles comprising intact recombinant viral genomes, empty recombinant viral capsid particles, and recombinant viral particles comprising variant recombinant viral genomes. In some embodiments the variant genomes are smaller than the intact recombinant viral genome (e.g., truncated genomes). In some embodiments, the variant genomes are larger than the intact recombinant viral genome (e.g., aggregates, recombinants, etc.). In some embodiments the variant genomes include genomes that are smaller and larger than the intact recombinant viral genome.

In some embodiments, the invention provides methods of monitoring the heterogeneity of recombinant viral particles during the purification of a preparation of recombinant viral particles (e.g., rAAV, rAd, lentiviral, or rHSV particles) the method comprising removing a sample of the recombinant viral particles from the preparation following one or more steps in the purification process and determining the relative amount of full capsids comprising an intact recombinant viral genome, empty capsids and/or recombinant viral particles with variant genomes using AUC as described herein, wherein an increase in the relative amount of recombinant viral particles comprising intact viral genomes indicates an increase in the homogeneity of full viral particles in the preparation of recombinant viral particles.

In embodiments of the embodiments described above, the recombinant viral particles have been purified using one or more purification steps. Examples of purification steps include but are not limited to equilibrium centrifugation, anion exchange filtration, tangential flow filtration (TFF), apatite chromatography, heat inactivation of helper virus, hydrophobic interaction chromatography, immunoaffinity chromatography, size exclusion chromatography (SEC), nanofiltration, cation exchange chromatography, and anion exchange chromatography.

In embodiments of the embodiments described above, the recombinant viral particles comprise a self-complementary AAV (scAAV) genome. In some embodiments, the recombinant AAV genome comprises a first heterologous polynucleotide sequence (e.g., a therapeutic transgene coding strand) and a second heterologous polynucleotide sequence (e.g., the noncoding or antisense strand of the therapeutic transgene) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR. In some embodiments, the scAAV viral particles comprise a monomeric form of an scAAV genome. In some embodiments, the scAAV viral particles comprise the dimeric form of and scAAV genome. In some embodiments, AUC as described herein is used to detect the presence of rAAV particles comprising the monomeric form of an scAAV genome. In some embodiments, AUC as described herein is used to detect the presence of rAAV particles comprising the dimeric form of an scAAV genome. In some embodiments, the packaging of scAAV genomes into capsid is monitored by AUC described herein.

In embodiments of the embodiments described above, the rAAV particles comprise an AAV1 capsid, an AAV2 capsid, an AAV3 capsid, an AAV4 capsid, an AAV5 capsid, an AAV6 capsid (e.g., a wild-type AAV6 capsid, or a variant AAV6 capsid such as ShH10, as described in U.S. PG Pub. 2012/0164106), an AAV7 capsid, an AAV8 capsid, an AAVrh8 capsid, an AAVrh8R, an AAV9 capsid (e.g., a wild-type AAV9 capsid, or a modified AAV9 capsid as described in U.S. PG Pub. 2013/0323226), an AAV10 capsid, an AAVrh10 capsid, an AAV11 capsid, an AAV12 capsid, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, a mouse AAV capsid, or an AAV capsid described in U.S. Pat. No. 8,283,151 or International Publication No. WO/2003/042397. In embodiments of the above embodiments described above, the rAAV particles comprise at least one AAV1 ITR, AAV2 ITR, AAV3 ITR, AAV4 ITR, AAV5 ITR, AAV6 ITR, AAV7 ITR, AAV8 ITR, AAVrh8 ITR, AAV9 ITR, AAV10 ITR, AAVrh10 ITR, AAV11 ITR, AAV12 ITR, AAV DJ ITR, goat AAV ITR, bovine AAV ITR, or mouse AAV ITR. In some embodiments, the rAAV particles comprise ITRs from one AAV serotype and AAV capsid from another serotype. For example, the rAAV particles may comprise a therapeutic transgene flanked by at least one AAV2 ITR encapsidated into an AAV9 capsid. Such combinations may be referred to as pseudotyped rAAV particles.

IV. Viral Particles

The methods disclosed herein may find use, inter alia, in characterizing species of interest in a variety of viral particles (e.g., viral particles with a full genome, as compared to viral particles with truncated genomes and/or viral particles comprising DNA impurities).

In some embodiments, the viral particle is a recombinant AAV particle comprising a nucleic acid comprising a transgene flanked by one or two ITRs. The nucleic acid is encapsidated in the AAV particle. The AAV particle also comprises capsid proteins. In some embodiments, the nucleic acid comprises the protein coding sequence(s) of interest (e.g., a therapeutic transgene) operatively linked components in the direction of transcription, control sequences including transcription initiation and termination sequences, thereby forming an expression cassette. The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., *PNAS,* 2000, 97(7) 3428-32; Passini et al., *J. Virol.,* 2003, 77(12):7034-40; and Pechan et al., *Gene Ther.,* 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.,* 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS,* 2002, 99(18): 11854-6; Gao et al., *PNAS,* 2003, 100(10): 6081-6; and Bossis et al., *J. Virol.,* 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AAV6, AAV7, AAV8, AAV9, AAVrh.8, AAVrh.10, AAV11, AAV12, a tyrosine capsid mutant, a heparin binding capsid mutant, an AAV2R471A capsid, an AAVAAV2/2-7m8 capsid, an AAV DJ capsid, an AAV2 N587A capsid, an AAV2 E548A capsid, an AAV2 N708A capsid, an AAV V708K capsid, a goat AAV capsid, an AAV1/AAV2 chimeric capsid, a bovine AAV capsid, or a mouse AAV capsid, or the like. In some embodiments, the nucleic acid in the AAV comprises an ITR of AAV1, AAV2, AAV3, AAV4, AAV5, AAV6, AAV7, AAV8, AAV9, AAVrh.8, AAVrh10, AAV11, AAV12 or the like. In further embodiments, the rAAV particle comprises capsid proteins of AAV1, AAV2, AAV3, AAV4, AAV5, AAV6, AAV7, AAV8, AAV9, AAVrh.8, AAVrh.10, AAV11, AAV12 or the like. In further embodiments, the rAAV particle comprises capsid proteins of an AAV serotype from Clades A-F (Gao, et al. *J. Virol.* 2004, 78(12):6381).

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, a rAAV particle can comprise AAV9 capsid proteins and at least one AAV2 ITR or it can comprise AAV2 capsid proteins and at least one AAV9 ITR. In yet another example, a rAAV particle can comprise capsid proteins from both AAV9 and AAV2, and further comprise at least one AAV2 ITR. Any combination of AAV serotypes for production of a rAAV particle is provided herein as if each combination had been expressly stated herein.

In some embodiments, the AAV comprises at least one AAV1 ITR and capsid protein from any of AAV2, AAV3, AAV4, AAV5, AAV6, AAV7, AAV8, AAV9, AAVrh.8, AAVrh10, AAV11, and/or AAV12. In some embodiments, the AAV comprises at least one AAV2 ITR and capsid protein from any of AAV1, AAV3, AAV4, AAV5, AAV6, AAV7, AAV8, AAV9, AAVrh.8, AAVrh10, AAV11, and/or AAV12. In some embodiments, the AAV comprises at least one AAV3 ITR and capsid protein from any of AAV1, AAV2, AAV4, AAV5, AAV6, AAV7, AAV8, AAV9, AAVrh.8, AAVrh10, AAV11, and/or AAV12. In some embodiments, the AAV comprises at least one AAV4 ITR and capsid protein from any of AAV1, AAV2, AAV3, AAV5, AAV6, AAV7, AAV8, AAV9, AAVrh.8, AAVrh10, AAV11, and/or AAV12. In some embodiments, the AAV comprises at least one AAV5 ITR and capsid protein from any of AAV1, AAV2, AAV3, AAV4, AAV6, AAV7, AAV8, AAV9, AAVrh.8, AAVrh10, AAV11, and/or AAV12. In some embodiments, the AAV comprises at least one AAV6 ITR and capsid protein from any of AAV1, AAV2, AAV3, AAV4, AAV5, AAV7, AAV8, AAV9, AAVrh.8, AAVrh10, AAV11, and/or AAV12. In some embodiments, the AAV comprises at least one AAV7 ITR and capsid protein from any of AAV1, AAV2, AAV3, AAV4, AAV5, AAV6, AAV8, AAV9, AAVrh.8, AAVrh10, AAV11, and/or AAV12. In some embodiments, the AAV comprises at least one AAV8 ITR and capsid protein from any of AAV1, AAV2, AAV3, AAV4, AAV5, AAV6, AAV7, AAV9, AAVrh.8, AAVrh10, AAV11, and/or AAV12. In some embodiments, the AAV comprises at least one AAV9 ITR and capsid protein from any of AAV1, AAV2, AAV3, AAV4, AAV5, AAV6, AAV7, AAV8, AAVrh.8, AAVrh10, AAV11, and/or AAV12. In some embodiments, the AAV comprises at least one AAVrh8 ITR and capsid protein from any of AAV1, AAV2, AAV3, AAV4, AAV5, AAV6, AAV8, AAV9, AAVrh10, AAV11, and/or AAV12. In some embodiments, the AAV comprises at least one AAVrh10 ITR and capsid protein from any of AAV1, AAV2, AAV3, AAV4, AAV5, AAV6, AAV7, AAV8, AAV9, AAV11, and/or AAV12. In some embodiments, the AAV comprises at least one AAV11 ITR and capsid protein from any of AAV1, AAV2, AAV3, AAV4, AAV5, AAV6, AAV7, AAV8, AAVrh8, AAV9, AAVrh10, and/or AAV12. In some embodiments, the AAV comprises at least one AAV12 ITR and capsid protein from any of AAV1, AAV2, AAV3, AAV4, AAV5, AAV6, AAV7, AAV8, AAV rh8, AAV9, AAVrh10, and/or AAV11.

Self-Complementary AAV Viral Genomes

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,765,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., a therapeutic transgene coding strand) and a second heterologous polynucleotide sequence (e.g., the non-coding or antisense strand of the therapeutic transgene) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR (e.g., the right ITR). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

In some embodiments, the viral particle is an adenoviral particle. In some embodiments, the adenoviral particle is a recombinant adenoviral particle, e.g., a polynucleotide vector comprising one or more heterologous sequences (i.e., nucleic acid sequence not of adenoviral origin) between two ITRs. In some embodiments, the adenoviral particle lacks or contains a defective copy of one or more E1 genes, which renders the adenovirus replication-defective. Adenoviruses include a linear, double-stranded DNA genome within a large (~950 Å), non-enveloped icosahedral capsid. Adenoviruses have a large genome that can incorporate more than 30 kb of heterologous sequence (e.g., in place of the E1 and/or E3 region), making them uniquely suited for use with larger heterologous genes. They are also known to infect dividing and non-dividing cells and do not naturally integrate into the host genome (although hybrid variants may possess this ability). In some embodiments, the adenoviral vector may be a first generation adenoviral vector with a heterologous sequence in place of E1. In some embodiments, the adenoviral vector may be a second generation adenoviral vector with additional mutations or deletions in E2A, E2B, and/or E4. In some embodiments, the adenoviral vector may be a third generation or gutted adenoviral vector that lacks all viral coding genes, retaining only the ITRs and packaging signal and requiring a helper adenovirus in trans for replication, and packaging. Adenoviral particles have been investigated for use as vectors for transient transfection of mammalian cells as well as gene therapy vectors. For further description, see, e.g., Danthinne, X. and Imperiale, M. J. (2000) Gene Ther. 7:1707-14 and Tatsis, N. and Ertl, H. C. (2004) Mol. Ther. 10:616-29.

In some embodiments, the viral particle is a recombinant adenoviral particle comprising a nucleic acid comprising a transgene. Use of any adenovirus serotype is considered within the scope of the present invention. In some embodiments, the recombinant adenoviral vector is a vector derived from an adenovirus serotype, including without limitation, AdHu2, AdHu3, AdHu4, AdHu5, AdHu7, AdHu11, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, and porcine Ad type 3. The adenoviral particle also comprises capsid proteins. In some embodiments, the recombinant viral particles comprise an adenoviral particle in combination with one or more foreign viral capsid proteins. Such combinations may be referred to as pseudotyped recombinant adenoviral particles. In some embodiments, foreign viral capsid proteins used in pseudotyped recombinant adenoviral particles are derived from a foreign virus or from another adenovirus serotype. In some embodiments, the foreign viral capsid proteins are derived from, including without limitation, reovirus type 3. Examples of vector and capsid protein combinations used in pseudotyped adenovirus particles can be found in the following references (Tatsis, N. et al. (2004) Mol. Ther. 10(4):616-629 and Ahi, Y. et al. (2011) Curr. Gene Ther. 11(4):307-320). Different adenovirus serotypes can be used to optimize transduction of particular target cells or to target specific cell types within a particular target tissue (e.g., a diseased tissue). Tissues or cells targeted by specific adenovirus serotypes, include without limitation, lung (e.g. HuAd3), spleen and liver (e.g. HuAd37), smooth muscle, synoviocytes, dendritic cells, cardiovascular cells, tumor cell lines (e.g. HuAd11), and dendritic cells (e.g. HuAd5 pseudotyped with reovirus type 3, HuAd30, or HuAd35). For further description, see Ahi, Y. et al. (2011) Curr. Gene Ther. 11(4):307-320, Kay, M. et al. (2001) Nat. Med. 7(1):33-40, and Tatsis, N. et al. (2004) Mol. Ther. 10(4):616-629.

In some embodiments, the viral particle is a lentiviral particle. In some embodiments, the lentiviral particle is a recombinant lentiviral particle, e.g., a polynucleotide vector comprising one or more heterologous sequences (i.e., nucleic acid sequence not of lentiviral origin) between two LTRs. Lentiviruses are positive-sense, ssRNA retroviruses with a genome of approximately 10 kb. Lentiviruses are known to integrate into the genome of dividing and non-dividing cells. Lentiviral particles may be produced, for example, by transfecting multiple plasmids (typically the lentiviral genome and the genes required for replication and/or packaging are separated to prevent viral replication) into a packaging cell line, which packages the modified lentiviral genome into lentiviral particles. In some embodiments, a lentiviral particle may refer to a first generation vector that lacks the envelope protein. In some embodiments, a lentiviral particle may refer to a second generation vector that lacks all genes except the gag/pol and tat/rev regions. In some embodiments, a lentiviral particle may refer to a third generation vector that only contains the endogenous rev, gag, and pol genes and has a chimeric LTR for transduction without the tat gene (see Dull, T. et al. (1998) J. Virol. 72:8463-71). For further description, see Durand, S. and Cimarelli, A. (2011) Viruses 3:132-59.

In some embodiments, the viral particle is a recombinant lentiviral particle comprising a nucleic acid comprising a transgene. Use of any lentiviral vector is considered within the scope of the present invention. In some embodiments, the lentiviral vector is derived from a lentivirus including, without limitation, human immunodeficiency virus-1 (HIV-1), human immunodeficiency virus-2 (HIV-2), simian immunodeficiency virus (SIV), feline immunodeficiency virus (Hy), equine infectious anemia virus (EIAV), bovine immunodeficiency virus (BIV), Jembrana disease virus (JDV), visna virus (VV), and caprine arthritis encephalitis virus (CAEV). The lentiviral particle also comprises capsid proteins. In some embodiments, the recombinant viral particles comprise a lentivirus vector in combination with one or more foreign viral capsid proteins. Such combinations may be referred to as pseudotyped recombinant lentiviral particles. In some embodiments, foreign viral capsid proteins used in pseudotyped recombinant lentiviral particles are derived from a foreign virus. In some embodiments, the foreign viral capsid protein used in pseudotyped recombinant lentiviral particles is Vesicular stomatitis virus glycoprotein (VSV-GP). VSV-GP interacts with a ubiquitous cell receptor, providing broad tissue tropism to pseudotyped recombinant lentiviral particles. In addition, VSV-GP is thought to provide higher stability to pseudotyped recombinant lentiviral particles. In other embodiments, the foreign viral capsid proteins are derived from, including without limitation, Chandipura virus, Rabies virus, Mokola virus, Lymphocytic choriomeningitis virus (LCMV), Ross River virus (RRV), Sindbis virus, Semliki Forest virus (SFV), Venezuelan equine encephalitis virus, Ebola virus Reston, Ebola virus Zaire, Marburg virus, Lassa virus, Avian leukosis virus (ALV), Jaagsiekte sheep retrovirus (JSRV), Moloney Murine leukemia virus (MLV), Gibbon ape leukemia virus (GALV), Feline endogenous retrovirus (RD114), Human T-lymphotropic virus 1 (HTLV-1), Human foamy virus, Maedi-visna virus (MVV), SARS-CoV, Sendai virus, Respiratory syncytia virus (RSV), Human parainfluenza virus type 3, Hepatitis C virus (HCV), Influenza virus, Fowl plague virus (FPV), or *Autographa californica* multiple nucleopolyhedro virus (AcMNPV). Examples of vector and capsid protein combinations used in pseudotyped Lentivirus particles can be found, for example, in Cronin, J. et al. (2005). Curr. Gene Ther. 5(4):387-398. Different pseudotyped recombinant lentiviral particles can be used to optimize transduction of particular target cells or to target specific cell types within a particular target tissue (e.g., a diseased tissue). For example, tissues targeted by specific pseudotyped recombinant lentiviral particles, include without limitation, liver (e.g. pseudotyped with a VSV-G, LCMV, RRV, or SeV F protein), lung (e.g. pseudotyped with an Ebola, Marburg, SeV F and HN, or JSRV protein), pancreatic islet cells (e.g. pseudotyped with an LCMV protein), central nervous system (e.g. pseudotyped with a VSV-G, LCMV, Rabies, or Mokola protein), retina (e.g. pseudotyped with a VSV-G or Mokola protein), monocytes or muscle (e.g. pseudotyped with a Mokola or Ebola protein), hematopoietic system (e.g. pseudotyped with an RD114 or GALV protein), or cancer cells (e.g. pseudotyped with a GALV or LCMV protein). For further description, see Cronin, J. et al. (2005). Curr. Gene Ther. 5(4):387-398 and Kay, M. et al. (2001) Nat. Med. 7(1):33-40.

In some embodiments, the viral particle is a herpes simplex virus (HSV) particle. In some embodiments, the HSV particle is a rHSV particle, e.g., a polynucleotide vector comprising one or more heterologous sequences (i.e., nucleic acid sequence not of lentiviral origin) between two TRs. HSV is an enveloped, double-stranded DNA virus with a genome of approximately 152 kb. Advantageously, approximately half of its genes are nonessential and may be deleted to accommodate heterologous sequence. HSV particles infect non-dividing cells. In addition, they naturally establish latency in neurons, travel by retrograde transport, and can be transferred across synapses, making them advantageous for transfection of neurons and/or gene therapy approaches involving the nervous system. In some embodiments, the HSV particle may be replication-defective or replication-competent (e.g., competent for a single replication cycle through inactivation of one or more late genes). For further description, see Manservigi, R. et al. (2010) Open Virol. J. 4:123-56.

In some embodiments, the viral particle is a rHSV particle comprising a nucleic acid comprising a transgene. Use of any HSV vector is considered within the scope of the present invention. In some embodiments, the HSV vector is derived from a HSV serotype, including without limitation, HSV-1 and HSV-2. The HSV particle also comprises capsid proteins. In some embodiments, the recombinant viral particles comprise a HSV vector in combination with one or more foreign viral capsid proteins. Such combinations may be referred to as pseudotyped rHSV particles. In some embodiments, foreign viral capsid proteins used in pseudotyped rHSV particles are derived from a foreign virus or from another HSV serotype. In some embodiments, the foreign viral capsid protein used in a pseudotyped rHSV particle is a Vesicular stomatitis virus glycoprotein (VSV-GP). VSV-GP interacts with a ubiquitous cell receptor, providing broad tissue tropism to pseudotyped rHSV particles. In addition, VSV-GP is thought to provide higher stability to pseudotyped rHSV particles. In other embodiments, the foreign viral capsid protein may be from a different HSV serotype. For example, an HSV-1 vector may contain one or more HSV-2 capsid proteins. Different HSV serotypes can be used to optimize transduction of particular target cells or to target specific cell types within a particular target tissue (e.g., a diseased tissue). Tissues or cells targeted by specific adenovirus serotypes include without limitation, central nervous system and neurons (e.g. HSV-1). For further description, see Manservigi, R. et al. (2010) Open Virol J 4:123-156, Kay, M. et al. (2001) Nat. Med. 7(1):33-40, and Meignier, B. et al. (1987) J Infect. Dis. 155(5):921-930.

V. Production of Viral Vectors

Numerous methods are known in the art for production of rAAV vectors, including transfection, stable cell line production, and infectious hybrid virus production systems which include adenovirus-AAV hybrids, herpesvirus-AAV hybrids (Conway, J E et al., (1997) J. Virology 71(11):8780-8789) and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a transgene (such as a therapeutic transgene) flanked by at least one AAV ITR sequences; and 5) suitable media and media components to support rAAV production. In some embodiments, the AAV rep and cap gene products may be from any AAV serotype. In general, but not obligatory, the AAV rep gene product is of the same serotype as the ITRs of the rAAV vector genome as long as the rep gene products may function to replicated and package the rAAV genome. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors. In some embodiments, the AAV helper functions are provided by adenovirus or HSV. In some embodiments, the AAV helper functions are provided by baculovirus and the host cell is an insect cell (e.g., Spodoptera frugiperda (Sf9) cells).

Suitable rAAV production culture media of the present invention may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

In some aspects, the invention provides methods for preparing rAAV particles with reduced empty capsids comprising a) culturing host cells under conditions suitable for rAAV production, wherein the cells comprise i) nucleic acid encoding a heterologous transgene flanked by at least one AAV ITR, ii) nucleic acid comprising AAV rep and cap coding regions, wherein the nucleic acid comprises a mutated p5 promoter wherein expression from the p5 promoter is reduced compared to a wild-type p5 promoter, and iii) nucleic acid encoding AAV helper virus functions; b) lysing the host cells to release rAAV particles; c) isolating the rAAV particles produced by the host cell; and d) analyzing the rAAV particles for the presence of empty capsids and/or rAAV particles with variant genomes by analytical ultracentrifugation as described above. In some embodiments, the p5 promoter of the nucleic acid encoding AAV rep and cap regions is located 3' to the rep and/or cap coding region. In some embodiments, the nucleic acid encoding AAV rep and cap coding regions is plasmid pHLP, pHLP19, or pHLP09 (see U.S. Pat. Nos. 5,622,856; 6,001,650; 6,027, 931; 6,365,403; 6,376,237; and 7,037,713; the content of each is incorporated herein in its entirety). In some embodiments, the AAV helper virus functions comprise adenovirus E1A function, adenovirus E1B function, adenovirus E2A function, adenovirus VA function and adenovirus E4 orf6 function.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles of the invention may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

Numerous methods are known in the art for production of adenoviral vector particles. For example, for a gutted adenoviral vector, the adenoviral vector genome and a helper adenovirus genome may be transfected into a packaging cell line (e.g., a 293 cell line). In some embodiments, the helper adenovirus genome may contain recombination sites flanking its packaging signal, and both genomes may be transfected into a packaging cell line that expresses a recombinase (e.g., the Cre/loxP system may be used), such that the adenoviral vector of interest is packaged more efficiently than the helper adenovirus (see, e.g., Alba, R. et al. (2005) *Gene Ther.* 12 Suppl 1:S18-27). Adenoviral vectors may be harvested and purified using standard methods, such as those described herein.

Numerous methods are known in the art for production of lentiviral vector particles. For example, for a third-generation lentiviral vector, a vector containing the lentiviral genome of interest with gag and pol genes may be co-transfected into a packaging cell line (e.g., a 293 cell line) along with a vector containing a rev gene. The lentiviral genome of interest also contains a chimeric LTR that promotes transcription in the absence of Tat (see Dull, T. et al. (1998) *J Virol.* 72:8463-71). Lentiviral vectors may be harvested and purified using methods (e.g., Segura M M, et al., (2013) *Expert Opin Biol Ther.* 13(7):987-1011) described herein.

Numerous methods are known in the art for production of HSV particles. HSV vectors may be harvested and purified using standard methods, such as those described herein. For example, for a replication-defective HSV vector, an HSV genome of interest that lacks all of the immediate early (IE) genes may be transfected into a complementing cell line that provides genes required for virus production, such as ICP4, ICP27, and ICP0 (see, e.g., Samaniego, L. A. et al. (1998) *J. Virol.* 72:3307-20). HSV vectors may be harvested and purified using methods described (e.g., Goins, W F et al., (2014) *Herpes Simplex Virus Methods in Molecular Biology* 1144:63-79).

VI. Purification of rAAV Vectors

At harvest, rAAV production cultures of the present invention may contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins. In addition, rAAV production cultures further include rAAV particles having an AAV capsid serotype selected from the group consisting of AAV1, AAV2, AAV3, AAV4, AAV5, AAV6, AAV7, AAV8, AAVrh8, AAV9, AAV10, AAVrh10, AAV11, or AAV12. In some embodiments, the rAAV production cultures further comprise empty AAV capsids (e.g., a rAAV particle comprising capsid proteins but no rAAV genome). In some embodiments, the rAAV production cultures further comprise rAAV particles comprising variant rAAV genomes (e.g., a rAAV particle comprising a rAAV genome that differs from an intact full-length rAAV genome). In some embodiments, the rAAV production cultures further comprise rAAV particles comprising truncated rAAV genomes. In some embodiments, the rAAV production cultures further comprise rAAV particles comprising AAV-encapsidated DNA impurities.

In some embodiments, the rAAV production culture harvest is clarified to remove host cell debris. In some embodiments, the production culture harvest is clarified by filtration through a series of depth filters including, for example, a grade DOHC Millipore Millistak+HC Pod Filter, a grade A1HC Millipore Millistak+HC Pod Filter, and a 0.2 μm Filter Opticap XL1O Millipore Express SHC Hydrophilic Membrane filter. Clarification can also be achieved by a variety of other standard techniques known in the art, such as, centrifugation or filtration through any cellulose acetate filter of 0.2 μm or greater pore size known in the art.

In some embodiments, the rAAV production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C. for a period of 30 minutes to several hours.

rAAV particles may be isolated or purified using one or more of the following purification steps: equilibrium centrifugation; flow-through anionic exchange filtration; tangential flow filtration (TFF) for concentrating the rAAV particles; rAAV capture by apatite chromatography; heat inactivation of helper virus; rAAV capture by hydrophobic interaction chromatography; buffer exchange by size exclusion chromatography (SEC); nanofiltration; and rAAV capture by anionic exchange chromatography, cationic exchange chromatography, or affinity chromatography. These steps may be used alone, in various combinations, or in different orders. In some embodiments, the method comprises all the steps in the order as described below. Methods to purify rAAV particles are found, for example, in Xiao et al., (1998) *Journal of Virology* 72:2224-2232; U.S. Pat. Nos. 6,989,264 and 8,137,948 and WO 2010/148143. Methods to purify adenovirus particles are found, for example, in Bo, H et al., (2014) *Eur. J Pharm. Sci.* 67C: 119-125. Methods to purify lentivirus particles are found, for example, in Segura M M, et al., (2013) *Expert Opin Biol Ther.* 13(7):987-1011.

Methods to purify HSV particles are found, for example, in Goins, W F et al., (2014) *Herpes Simplex Virus Methods in Molecular Biology* 1144:63-79.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Characterization of Recombinant Adeno-Associated Viral Vector Preparations by Analytical Ultracentrifugation Adeno-associated viruses (AAV) have features that make them attractive as vectors for gene therapy. Wild-type AAV consists of two open reading frames (rep and cap) which code for all structural and regulatory elements required for assembly, replication and infection. The rep ORF codes for Rep 78 and 68 proteins which have genome replication functions as well as Rep 52 and 40 proteins which are involved in single strand replication and packaging. The cap ORF codes for the three structural capsid proteins: VP1, VP2 and VP3. Recombinant AAV vector is typically produced by the triple transfection method using the "gutless" vector approach (Xiao, X, et al., 1998, *J. Virol.* 3:2224-2232). The rep and cap genes are replaced with the therapeutic gene and its regulatory elements sandwiched between a 5' and 3' inverted terminal repeat (ITR), the rep and cap genes are provided in trans on a separate plasmid and a third plasmid contributes required adenoviral helper genes. It is postulated that the viral capsids are fully assembled and the ITR flanked vector genome is then inserted into the capsid via a capsid pore (Myers, M W & Carter, B J, 1980, *Virology*, 102:71-82). The resulting population of capsids contains both non-genome containing capsids (empty capsids) as well as genome containing capsids. In addition, capsids may contain incomplete portions of the recombinant viral genome. The vector prep may then purified by affinity chromatography to isolate the capsids from the cellular debris and can be further processed to enrich for intact vector by anion exchange chromatography.

Based on their recent approval for use in gene therapy, adeno-associated viral (AAV) vectors have emerged as an important class of novel biopharmaceutical drug products. The generation of AAV vector products requires an analytical method that monitors product quality with regard to homogeneity, purity, and consistency of manufacturing, yet to date no method to support AAV vector characterization has been established. To meet this demand, the potential use of analytical ultracentrifugation (AUC) as a technique to characterize the homogeneity of AAV vectors was investigated.

Methods
Sample Preparation

In order to support accurate AUC assessment, vector product (AAV2-transgene 2) was highly purified, suitably buffered, and concentrated to greater than $5 \times 10^{11}$ vg/mL. To achieve this, cell supernatants runs were purified using AVB affinity chromatography (GE Healthcare) and buffer-exchanged into PBS, pH 7.2 using a 10K MWCO Slide-a-Lyzer (Thermo Scientific). Product concentration was determined by optical density measurement at 260 nm ($OD_{260}$) by spectrophotometric methods. To generate reproducible and consistent AUC data, sample adjustments were made to target concentration by optical density measurement at 260 nm from 0.1 to 1.0, either by direct dilution with PBS or further concentration using Amicon Ultra-0.5/30K MWCO Centrifugal Filter Device.

Sedimentation Velocity AUC Data Acquisition

Sedimentation velocity analytical ultracentrifugation (SV-AUC) analysis was performed using a ProteomeLab™ XL-I (Beckman Coulter). 400 μL sample was loaded into the sample sector of a two sector velocity cell, and 400 μL PBS was loaded into the corresponding reference sector. The sample was placed in the four-hole rotor and allowed to equilibrate in the instrument until a temperature of 20° C. and full vacuum were maintained for one hour. Sedimentation velocity centrifugation was performed at 20,000 RPM, 20° C., 0.003 cm radial step setting, with no delay and with no replicates. Absorbance (260 nm) and Raleigh interference optics were used to simultaneously record radial concentration as a function of time until the smallest sedimenting component cleared the optical window (1.2 hour). Assay throughput was limited to a single sample per run based on absorbance scan collection times of greater than one minute, as well as the large size and rapid sedimentation of AAV.

AUC Data Analysis

The percent full capsid was determined by analyzing approximately 75 scans from each detection method using the SEDFIT (NIH/see worldwide web at analyticalultracentrifugation.com) continuous size C(S) distribution model. Second ($2^{nd}$) derivative regularization was applied to the fitting with a confidence level of F statistic=0.68. The following C(S) parameters were held constant: resolution=200 S, S min=1, S max=200 and frictional ratio=1.0. RI and TI noise subtractions were applied, and the meniscus position was allowed to float, letting the software choose the optimal position. This model fit the data to the Lamm equation, and the resulting size distribution was a "distribution of sedimentation coefficients" that looked like a chromatogram with the area under each peak proportional to concentration in units of Fringes or $OD_{260}$ units. The sedimentation coefficient (in Svedberg units) and the relative concentration (in OD units) were determined for each component in the distribution. Each AUC run was an independent assay, and each analysis was monitored for the following attributes to ensure quality of results: goodness of fit (rmsd), the ratio of $OD_{260\ nm}$/interference signal in fringes (A260/IF ratio) for each peak, consistency of sedimentation coefficients for each species between runs, and overall quality of the scans.

Absorbance Optics (260 nm)

Extinction coefficients were used to calculate molar concentration and the actual percent value of the intact vector peak from absorbance data. Molar absorbance extinction coefficients for both empty capsids ($\varepsilon_{260}/_{capsid}$=3.72e6) and intact vector ($\varepsilon_{260}/_{vector}$=3.00e7) were calculated based on published formulae (Sommer et al. (2003) *Mol Ther.*, 7:122-8). Extinction coefficients were available for empty capsid and intact vector peaks. The C(S) values were determined using the SEDFIT algorithm described by Schuck (2000) *Biophys. J.* 78:1606-19. Molar concentration of both intact vector and empty capsid were calculated using Beer's Law, and the percentage of full capsid was calculated from these values. Values were reported in terms of the percentage of full capsid.

Generation of an AUC Standard Curve

Because it is not possible to determine empirically the extinction coefficient of fragmented genomes of unknown size and sequence, a relationship between S value and genome size was established. To achieve this, rAAV vector preps with encapsidated viral genomes of known nucleotide size were analyzed by AUC, and a corresponding S value was determined as described above.

Production of rAAV by Transient Transfection

Recombinant AAV vector was produced by the triple transfection method using the "gutless" vector approach (Xiao et al. (1998) *J. Virol.*, 3:2224-32). In this approach, the rep and cap genes were replaced with the therapeutic gene and its regulatory elements, both sandwiched between a 5' and 3' inverted terminal repeat (ITR). The rep and cap genes were provided in trans on a separate plasmid, and a third plasmid contributed the required adenoviral helper genes. Without wishing to be bound to theory, it is postulated that the viral capsids are fully assembled, and the ITR flanked vector genome is then inserted into the capsid via a capsid pore (Myers & Carter (1980) *Virology*, 102:71-82). The resulting population of capsids contained both non-genome-containing capsids (empty capsids) and genome-containing capsids.

Production of rAAV by Producer Cell Platform

The AAV producer cell line is an alternative production platform used to generate clinical rAAV vectors. With this method, a HeLa S3 cell, adapted to growth in suspension, was engineered to have integrated copies of the AAV rep and cap genes required for vector replication and packaging, in addition to vector sequences and the selectable marker (see, e.g., Puro: Thorne et al. (2009) *Hum. Gene Ther.*, 20:707-14). Once infected with WT Adenovirus, which provides the helper functions required for replication, the cell produced recombinant AAV vector as well as adenovirus, which was subsequently removed during the purification process using ion-exchange chromatography.

Other Methods

Synthetic transgenes were cloned into a plasmid that contained a promoter of choice and bovine growth hormone polyadenylation signal sequence (polyA). The entire transgene expression cassette was then cloned into previral plasmid vector pAAVDC64 containing AAV2 inverted terminal repeats. The total size of the resulting AAV genomes in the respective expression plasmids (including the region flanked by ITRs) was 4-4.6 kb. The recombinant vectors were produced by triple transfection of 293 cells using helper plasmids expressing rep2/cap sequences and Adenovirus helper functions, pAd Helper (Stratagene, La Jolla, CA USA) The rep/cap helper expressed rep from AAV serotype 2, while the cap sequence encoded one of the following sequences: AAV cap 1, 2, 5, 9, or rh8R. Vectors were purified by affinity chromatography and in some cases were further purified to remove empty particles (see, e.g., Qu et al. (2007) *J. Virol. Methods.* 140:183-92).

Results

Analytical ultracentrifugation (AUC) using classical boundary sedimentation velocity was used to reveal the particle heterogeneities of recombinant adeno-associated virus (rAAV) vector preps. A mixture containing 20% rAAV2 particles with the full genome and 80% empty capsids was created by mixing together purified empty capsids and purified genome-containing capsids at defined ratios. The empty and full capsids were generated by $CsCl_2$ gradient purification of a mixture of empty and full capsids following triple transfection production. To monitor the movement of rAAV2 particles in response to a centrifugal force, this mixture of rAAV2 capsids was scanned at an absorbance of 260 nm along a centrifugal field at defined time intervals. FIG. 1A shows a representative scanning profile following centrifugation of the AAV2 mixture at 20,000 rpm for 1.2 hrs (until the smallest sedimenting species cleared the optical window). Scans represented the acquisition of concentration data as a function of radius r, at times t, to yield a series of concentration scans that revealed the complete migration pattern of constituent vector particles in the rAAV2 vector prep. In these sigmoidal curves or boundaries, the leading edge of the curve represented the faster sedimenting species (i.e., the genome-containing rAAV2 capsid), and the trailing edge of the curve represented the slower sedimenting species (i.e., the "empty" rAAV2 capsids) (FIG. 1A).

Figure 1B:
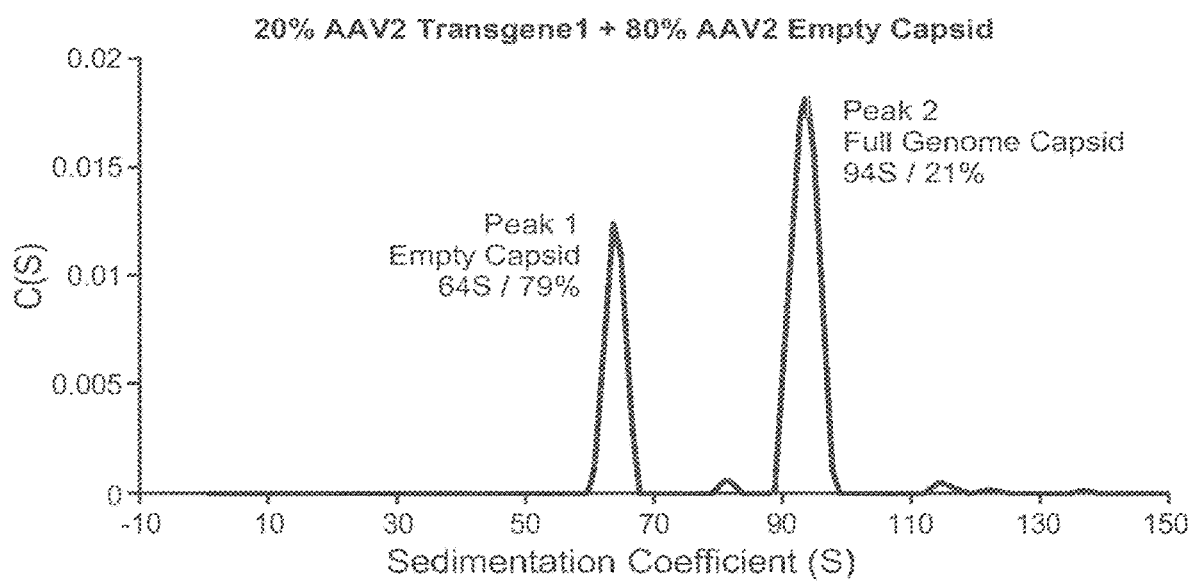

Plotting the differential sedimentation coefficient distribution value, C(S), versus the sedimentation coefficient (in Svedberg units, S) yielded distinct peaks with unique sedimentation coefficients for both the empty and genome-containing capsid species (FIG. 1B). The C(S) values were determined using the SEDFIT algorithm described by Schuck (2000) *Biophys.* 1, 78:1606-19. In order to calculate molar concentrations and percent value for each capsid species from the absorbance data, extinction coefficients were used according to Table 2.

TABLE 2

Extinction coefficients and molar concentrations for capsid species

| Species | Signal ($Abs_{260\ nm}$) | $\varepsilon_{260\ nm}$ | Molar concentration (M) | Relative abundance (%) |
|---|---|---|---|---|
| Peak 1 | 0.0479 | 3.73E+06 | 1.28E−08 | 79 |
| Peak 2 | 0.0909 | 2.59E+07 | 3.51E−09 | 21 |
| Sum | | | 1.63E−08 | |

Molar absorbance extinction coefficients for both the empty capsid ($\varepsilon_{260}/_{capsid}$-3.72e6) and genome containing capsid ($\varepsilon_{260}/_{capsid}$=3e7) were calculated using genome size and published formulae (Sommer et al., 2003). Molar concentrations of both genome-containing and empty capsids were then calculated using Beer's Law. The molar concentration of each species was used to calculate its relative abundance, expressed as a percentage of total capsids (FIG. 1). These results demonstrated that AUC may be used to accurately distinguish and quantify empty capsids and genome-containing capsids from a heterogeneous vector preparation.

Figure 2A:
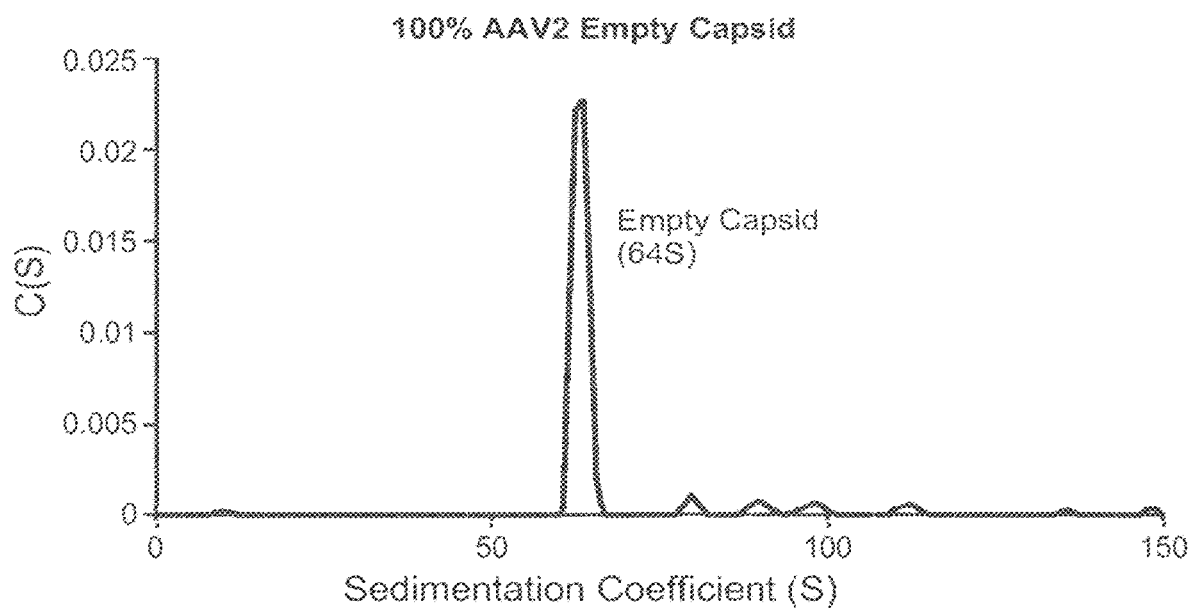
FIGS. 2A and 2B show the AUC profiles of pure populations of empty AAV2 capsids (FIG. 2A) and genome-containing AAV2-transgene 1 capsids (FIG. 2B). Each peak is labeled with the capsid species and its sedimentation coefficient (S).
Figure 2B:
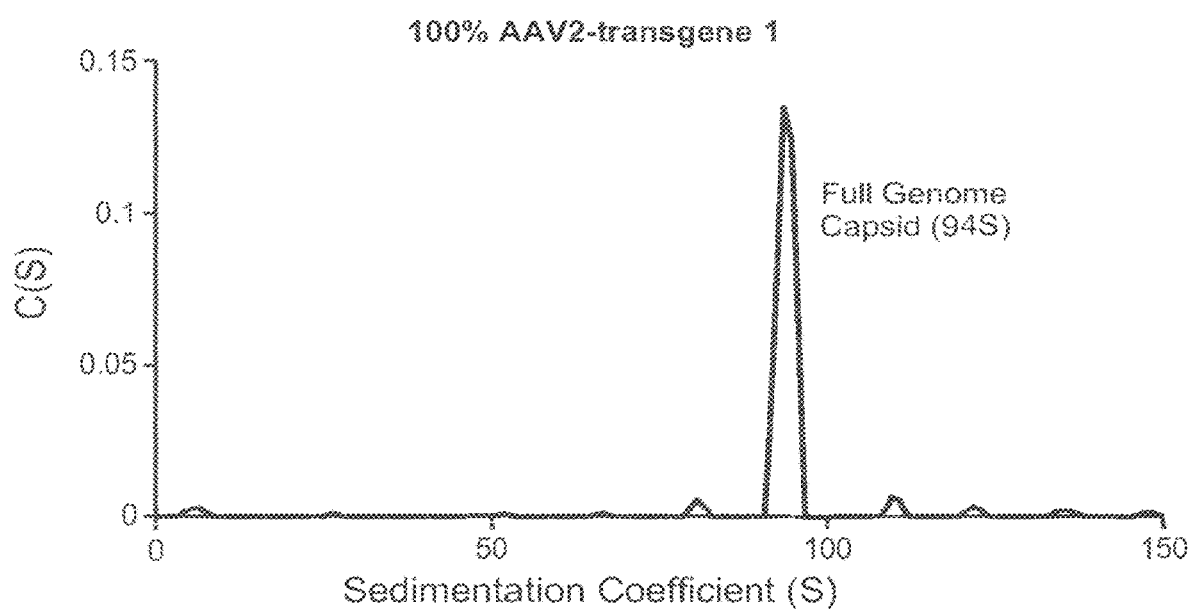

For the rAAV2 vector prep shown in FIG. 1, capsids containing a full genome were represented by the peak sedimenting at 94 S and accounted for 21% of the vector prep. Empty capsids sedimented with an S value of 64 S and accounted for 79% of the vector prep. These sedimentation coefficient values were confirmed by AUC analysis of pure populations of empty (FIG. 2A) or genome containing particles (FIG. 2B). The AUC profile of a pure population of rAAV2 empty capsids revealed a single peak with a sedimentation coefficient of 64 S, whereas the AUC profile of a pure population of rAAV2AUC genome-containing capsids revealed a single peak with a higher sedimentation coefficient of 94 S. These results agreed with the values generated from a heterogeneous preparation and further confirmed that AUC methods may be used to quantify genome-containing and empty AAV capsids from a heterogeneous preparation containing both species.

The AUC method was further assessed for reproducibility by performing five independent AUC runs of the same vector sample (scAAV2/9 LP2), as shown in Table 3. The sedimentation coefficients for both genome-containing and empty AAV2 capsids were highly reproducible, yielding coefficients of variation from 0.5-0.6%. Similarly, the relative abundance (expressed as a percentage of the total) of genome-containing capsids was determined with a coefficient of variation of approximately 2%. These results indicated that the AUC method for quantifying genome-containing and empty AAV2 capsids yields highly reproducible and consistent values.

TABLE 3

Five independent assays on scAAV2/9 LP2 sample.

| AUC Run | Empty Capsid, Peak 1 (S) | % Full Capsids | Full Capsid, Peak 3 S |
|---|---|---|---|
| 20110927A | 64.3 | 34.1 | 84.0 |
| 20111003A | 64.6 | 34.2 | 84.6 |
| 20111005A | 65.1 | 35.0 | 84.5 |
| 20111005B | 64.2 | 35.2 | 83.8 |
| 20111011A | 64.1 | 33.5 | 84.5 |
| Mean | 64.5 | 34.4 | 84.3 |
| Standard Deviation | 0.4 | 0.7 | 0.4 |
| % CV | 0.6 | 2.1 | 0.5 |

Example 2: Comparison of Interference and Absorbance Detection Methods for AUC

An alternative optical detection method for AUC, Rayleigh Interference Optics, was also evaluated. This detection method measures the sample concentration based on refractive index differences between a reference solution and the AAV containing sample. Like absorbance detection, interference detection can be applied to any rAAV regardless of the sequence of the genome. Unlike absorbance detection, which requires an extinction coefficient, interference detection yields integrated peaks that are directly proportional to concentration.

Figure 3A:
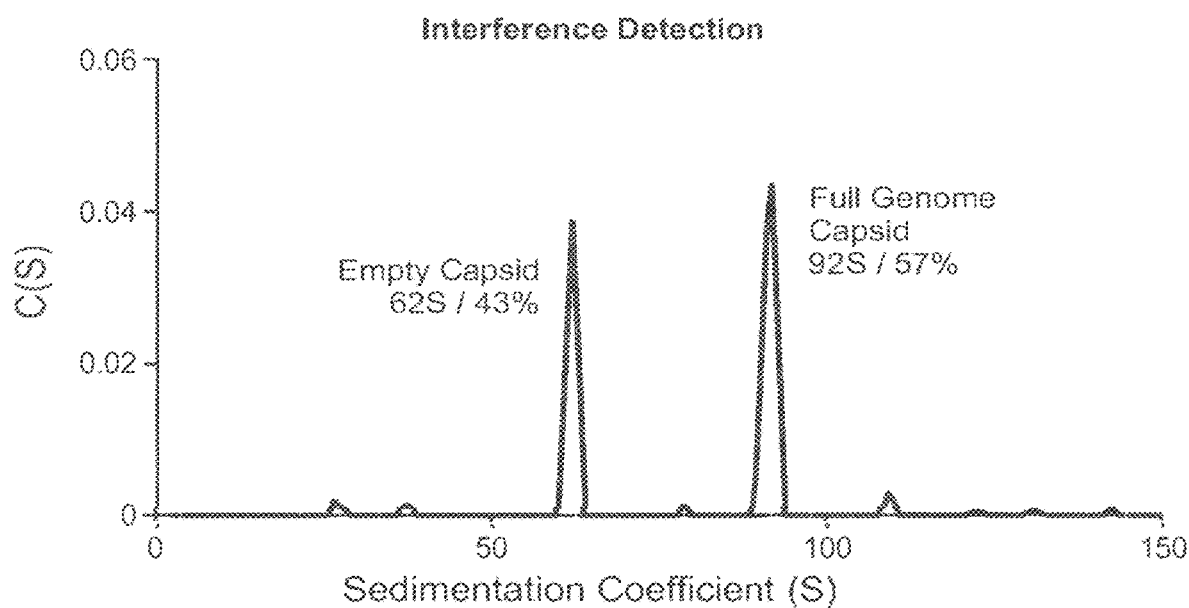
FIGS. 3A and 3B show a comparison between interference and absorbance detection methods by AUC.
Figure 3B:
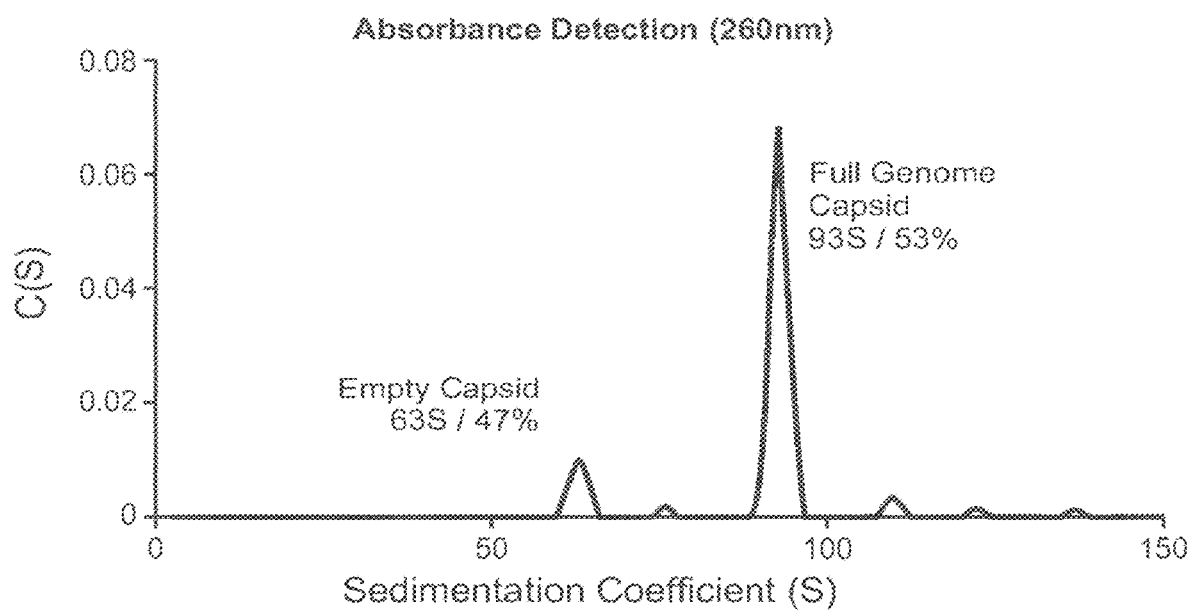

Pure populations of empty and genome-containing AAV2 capsids were mixed at a 1:1 ratio and analyzed by AUC using both interference (FIG. 3A) and absorbance detection methods (FIG. 3B). Interference detection revealed two populations of AAV capsids at the approximate expected ratios of 43% empty and 57% genome-containing (FIG. 3A). Both detection methods yielded similar abundance ratios. However, comparing the peak sizes generated by both methods illustrates the disconnect between peak height and concentration with absorbance detection (compare size of "empty capsid" peaks in FIGS. 3A and 3B). The data generated by both methods are compared in Table 4. The ratio of absorbance signal to interference signal ($A_{260nm}$/IF) can be used in a fashion analogous to the 260/280 ratio of absorbance data, and this assisted in identifying peaks in the C(S) distribution.

TABLE 4

S values and relative abundance generated by absorbance and interference detection.

| | Absorbance (260 nm) | | Interference | | | |
|---|---|---|---|---|---|---|
| Peak | Sedimentation coefficient (S) | Relative abundance (%) | Sedimentation coefficient (S) | Signal (fringes) | Relative abundance (%) | $A_{260nm}$/IF |
| Peak 1 | 63 | 47 | 62 | 0.080 | 43 | 0.41 |
| Peak 2 | 93 | 53 | 92 | 0.104 | 57 | 2.38 |
| Sum | | | | 0.184 | | |

Although interference optics offers precision and resolution, it may require a high concentration of sample. Moreover, interference optics may be affected by a mismatch between the reference and AAV sample buffer. AAV samples, however, typically contain a low protein concentration, and it may be necessary to completely match the AAV sample and reference buffers.

Example 3: Influence of Production Method on AAV Vector Heterogeneity

The previous examples demonstrated that the AUC method is a highly accurate and reproducible way to resolve and quantify empty and genome-containing AAV capsids from a heterogeneous mixture. This capability could be advantageous for a variety of applications to evaluate the quality of AAV vector preparations. For example, a major problem in producing pure AAV vector preparations is the presence of capsids with partial or fragmented genomes. To illustrate the utility of the AUC method for resolving these species, AAV vectors generated by two different methods, termed the "triple transfection" and "producer cell line" methods, were analyzed by AUC.

Figure 4:
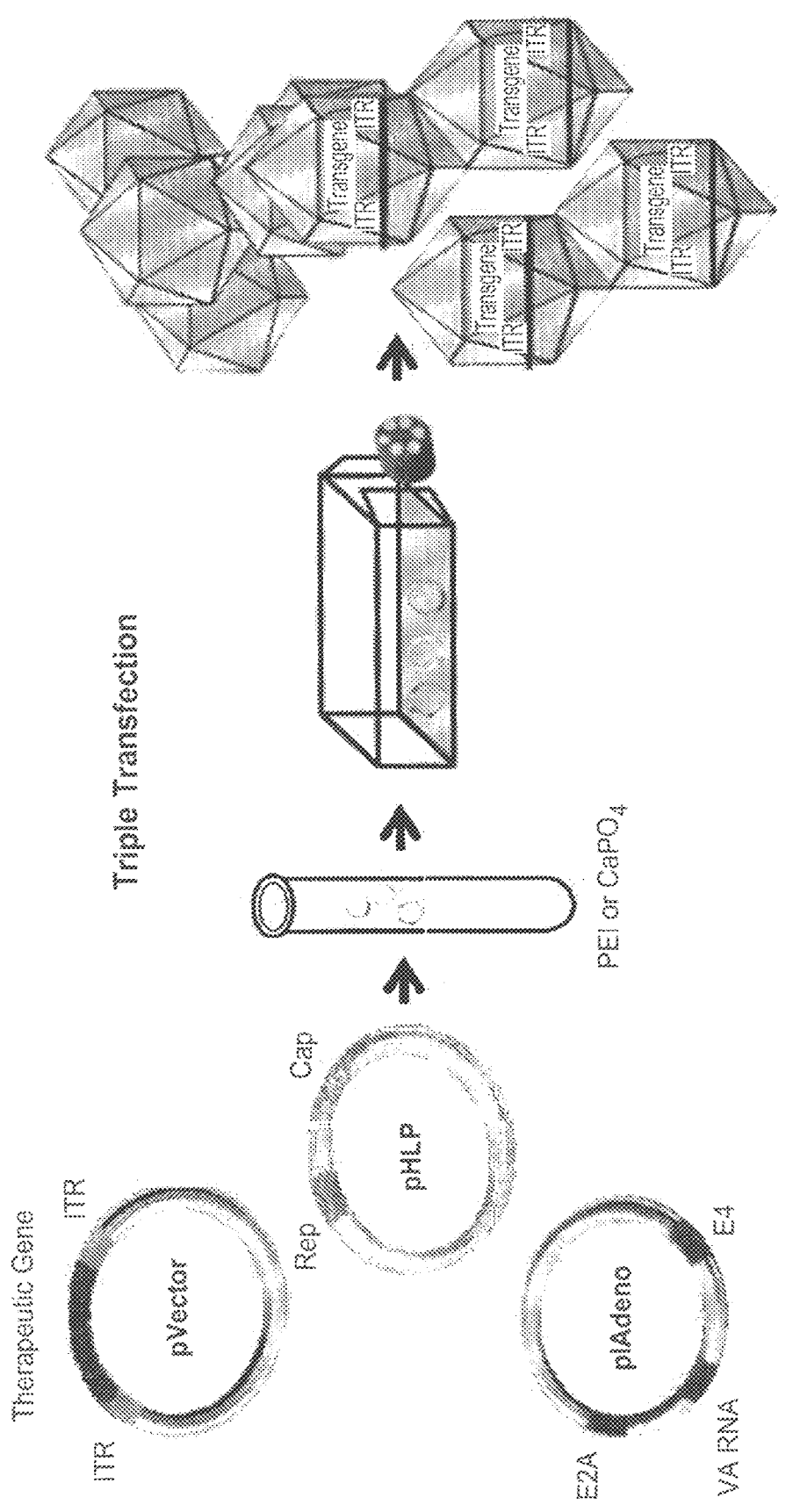
FIG. 4 illustrates the triple transfection method for AAV vector production. The three vectors, containing the gene of interest ("pVector"), AAV Rep and Cap genes ("pHLP"), and adenoviral components ("pIAdeno") are labeled. Note that both genome-containing (labeled with the "ITR-Transgene-ITR" graphic) and empty capsids (blank) are produced.
Figure 5:
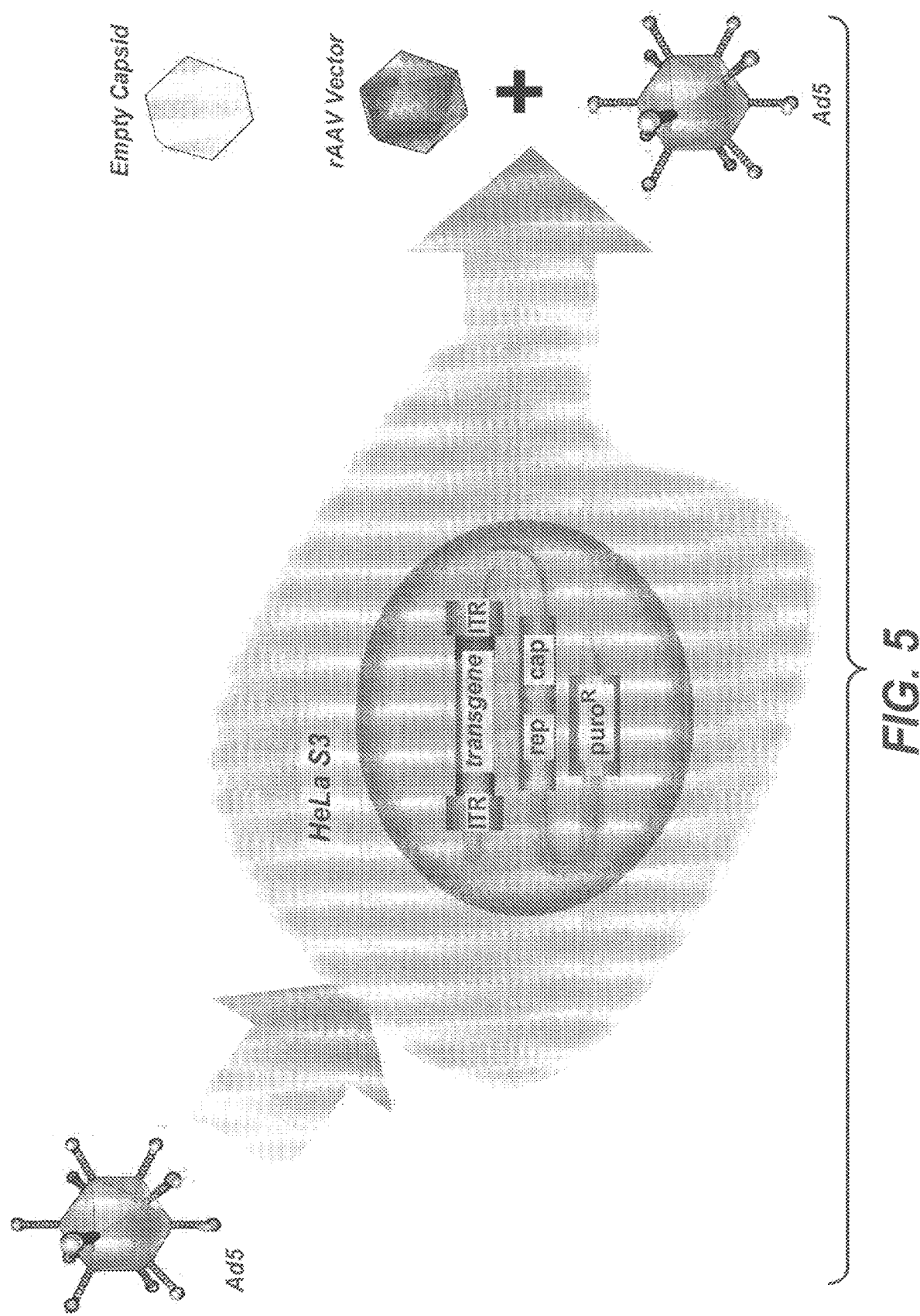
FIG. 5 illustrates the producer cell line method for AAV vector production. As labeled, the HeLa S3 cell line contains integrated Rep, Cap, and Puromycin resistance genes, along with an ITR-flanked transgene of interest. This cell line is infected with adenovirus ("Ad5") to stimulate recombinant viral production. Note that both genome-containing (labeled "recombinant viral Vector") and empty capsids are produced, in addition to adenovirus particles.
Figure 6A:
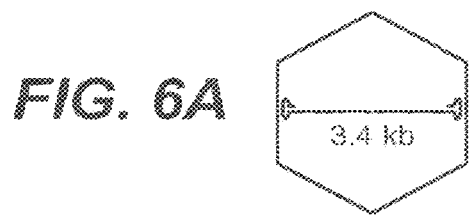
FIGS. 6A, 6B and 6C shows that vector production by the producer cell line and triple transfection methods yields different vector preparations, as revealed by AUC analysis.

An AAV2 vector harboring the transgene 2 was produced using either the triple transfection method (FIG. 4) or the producer cell line method (FIG. 5). For a description of these methods, see Example 1. Following chromatographic purification, both vector preps were analyzed by AUC. FIG. 6A shows a schematic of this AAV2 vector genome.

Figure 6B:
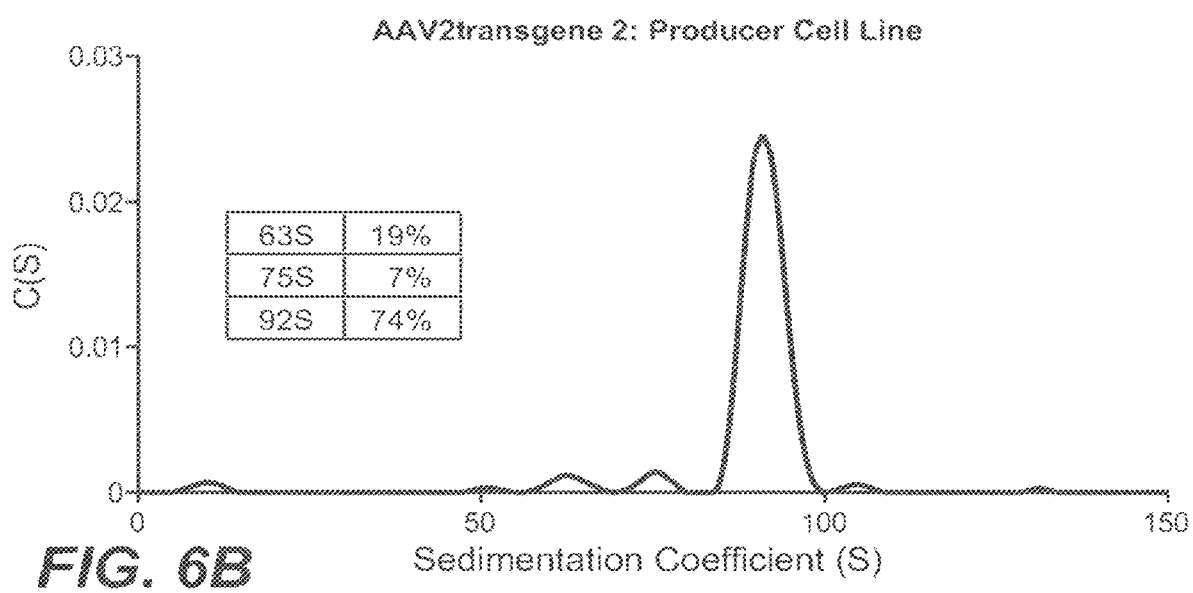
Figure 6C:
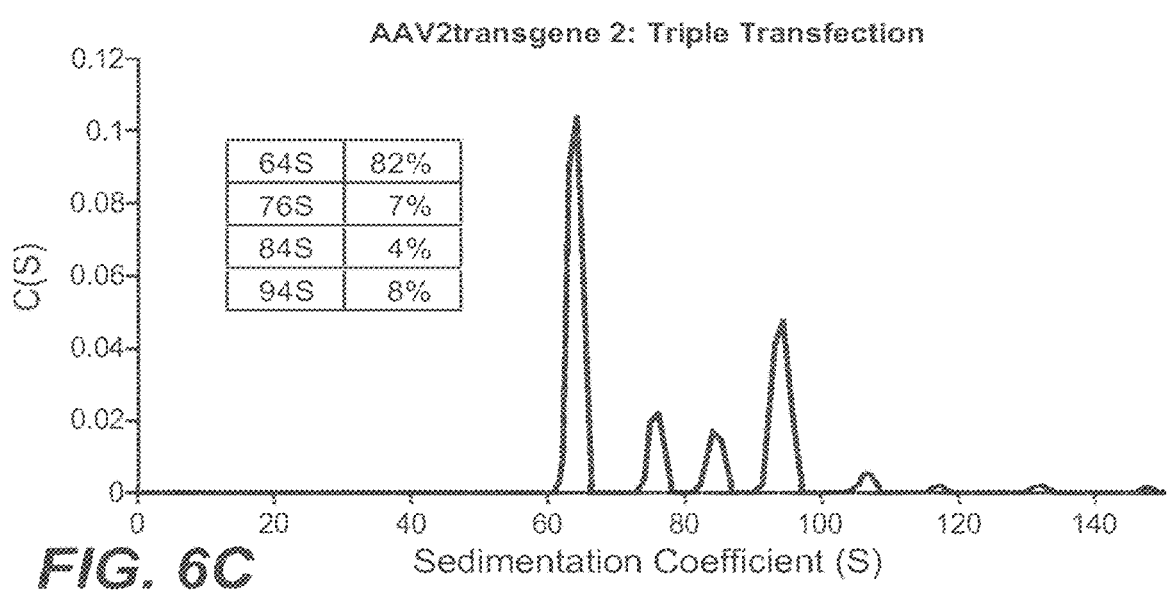

The AUC profiles of vector preps produced by these methods were remarkably different. Using the producer cell line method, 74% of capsids contained a full genome, represented by the 92 S species (FIG. 6B). 19% were empty capsids, with the remainder containing a fragmented genome (75 S species, 7%). In contrast, 82% of the capsids produced by the triple transfection method were empty, 64 S species (FIG. 6C), with 11% of capsids containing a fragmented genome (76 S and 84 S species) and only 8% of capsids having a full genome (94S).

These results demonstrate that vector preparations generated using the producer cell line technology may have high quality, containing predominantly capsids with a full genome. The vast majority of capsids produced by the triple transfection method are empty, with a greater proportion of capsids having a fragmented genome. These results also highlight the ability of the AUC method to resolve capsids with fragmented genomes, in addition to full genome-containing and empty capsids. Moreover, they illustrate the power of the AUC method in evaluating the quality and homogeneity of vector preparations.

Example 4: Use of AUC to Assess Removal of Empty Capsids from Vector Preps

Figure 7A:
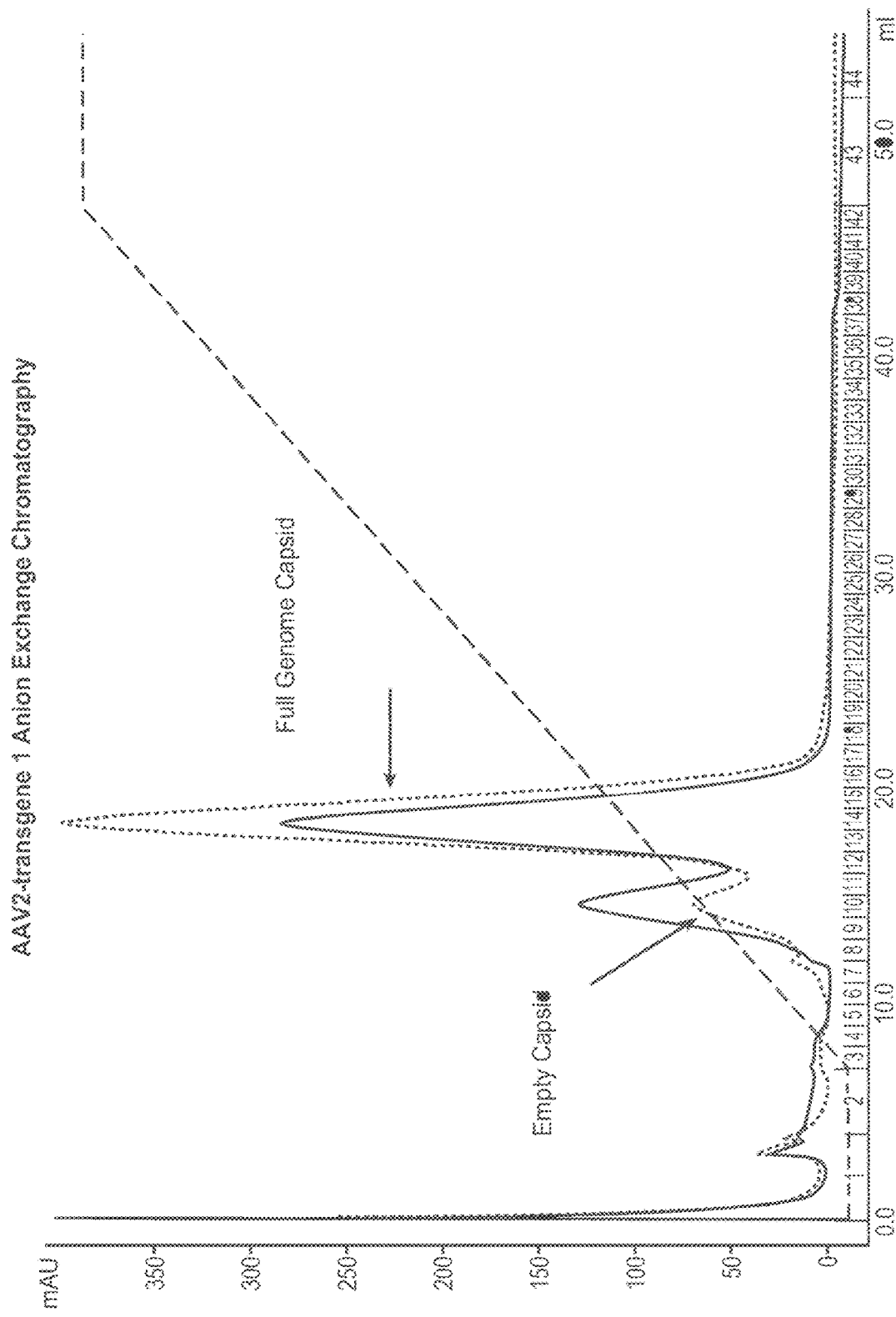
FIGS. 7A, 7B and 7C show that the AUC method may be used to monitor the quality and efficacy of vector purification.

The AUC method was evaluated as a tool to monitor removal of empty capsids using chromatographic methods (for methods, see Qu et al. (2007) *J. Virol. Methods*, 140: 183-92). Separation of empty and genome-containing capsids was performed using anion exchange chromatography (FIG. 7A). AUC was performed on the resolved peaks to demonstrate that the genome-containing rAAV2 particles were enriched in the later fractions eluted from the resin ("Full Genome Capsid" in FIG. 7A).

Figure 7B:
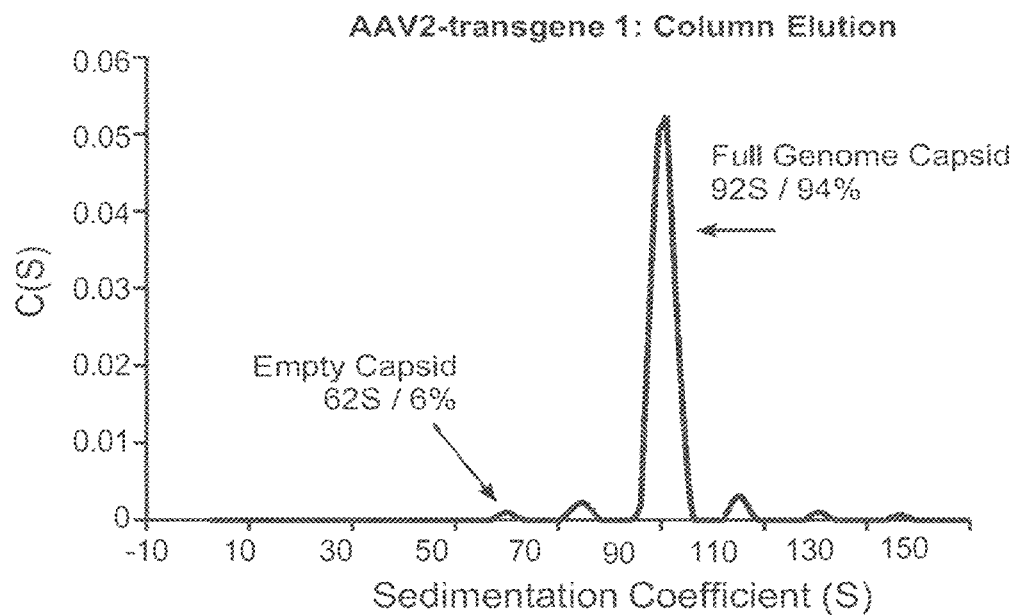
Figure 7C:
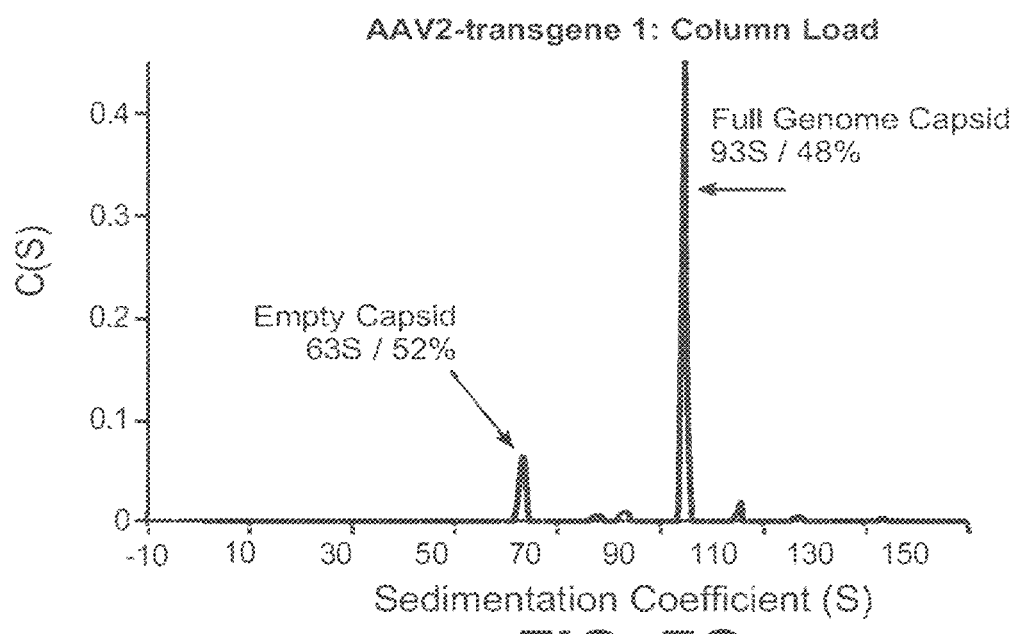

As shown in FIG. 7B, AUC analysis revealed that genome-containing capsids represented 94% of the vector prep upon elution from the column. This later fraction yielded a single peak with a sedimentation coefficient of 92 S. In contrast, the rAAV2 vector prep prior to the chromatographic step (FIG. 7C) had a substantial level of empty capsids. AUC analysis revealed two peaks with S values of 63 and 93, with the 63 S peak (empty capsid) representing 52% of the total capsid population. These results show that chromatographic methods are highly effective in removing empty capsids from AAV vector preparations. Importantly, they demonstrate the utility of applying the AUC method to evaluate vector quality upon purification. The AUC method is a useful tool for evaluating different vector purification protocols or techniques.

Example 5: Assessment of Viral Genome Integrity by the AUC Method

As illustrated in Example 3, AAV vector preparations may contain capsids packaged with fragmented genomes, in addition to full genome and empty species. A major problem in generating homogeneous AAV preparations for therapeutic or research applications is the presence of capsids with fragmented genomes, which may result in aberrant or absent expression of transgenes of interest. Indeed, heterogeneity associated with AAV vector preps has been reported to result from packaging of fragmented genomes or AAV-encapsidated DNA impurities. (Kapranov et al. (2012) *Hum. Gene Ther.*, 23:46-55). Therefore, AUC was evaluated as a tool to quantify the aberrant packaging of fragmented genomes in rAAV vector preps.

Figure 8:
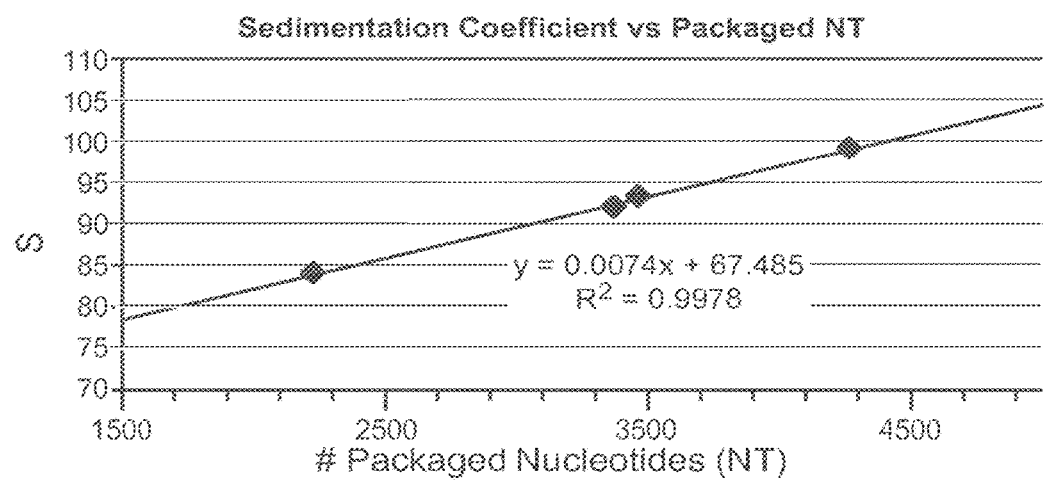
FIG. 8 shows the linear relationship between sedimentation coefficient and vector genome size. A standard curve plotting sedimentation coefficient (S) versus genome size is depicted, along with a line of best fit, its formula, and its associated $R^2$ value.

Because it is not possible to determine empirically the extinction coefficient of fragmented genomes of unknown size and sequence, a relationship between S value and genome size was established. To achieve this, rAAV vector preps with encapsidated viral genomes of known size were analyzed by AUC, and their corresponding S values were determined, as shown in Table 5. A standard curve was then generated to correlate genome size and S value (FIG. 8). This demonstrated a highly linear relationship ($R^2$=0.9978) between sedimentation coefficient and genome size.

TABLE 5

S values for rAAV vectors with known genome size.

| Predicted Trend Line | | Calculated values | |
| --- | --- | --- | --- |
| Sedimentation coefficient (S) (y) | Genome size (# NT) (x) | MW | Extinction coefficient (260 nm) |
| Empty capsid | N/A | | 3.72E+06 |
| 74 | 880 | 2.7E+05 | 9.17E+06 |
| 78 | 1421 | 4.4E+05 | 1.25E+07 |
| 82 | 1961 | 6.1E+05 | 1.59E+07 |
| 84 | 2232 | 6.9E+05 | 1.75E+07 |
| 88 | 2772 | 8.6E+05 | 2.09E+07 |
| 92 | 3313 | 1.0E+06 | 2.42E+07 |
| 96 | 3853 | 1.2E+06 | 2.76E+07 |
| 100 | 4394 | 1.4E+06 | 3.09E+07 |
| 104 | 4934 | 1.5E+06 | 3.43E+07 |
| 108 | 5475 | 1.7E+06 | 3.76E+07 |

Figure 9A:
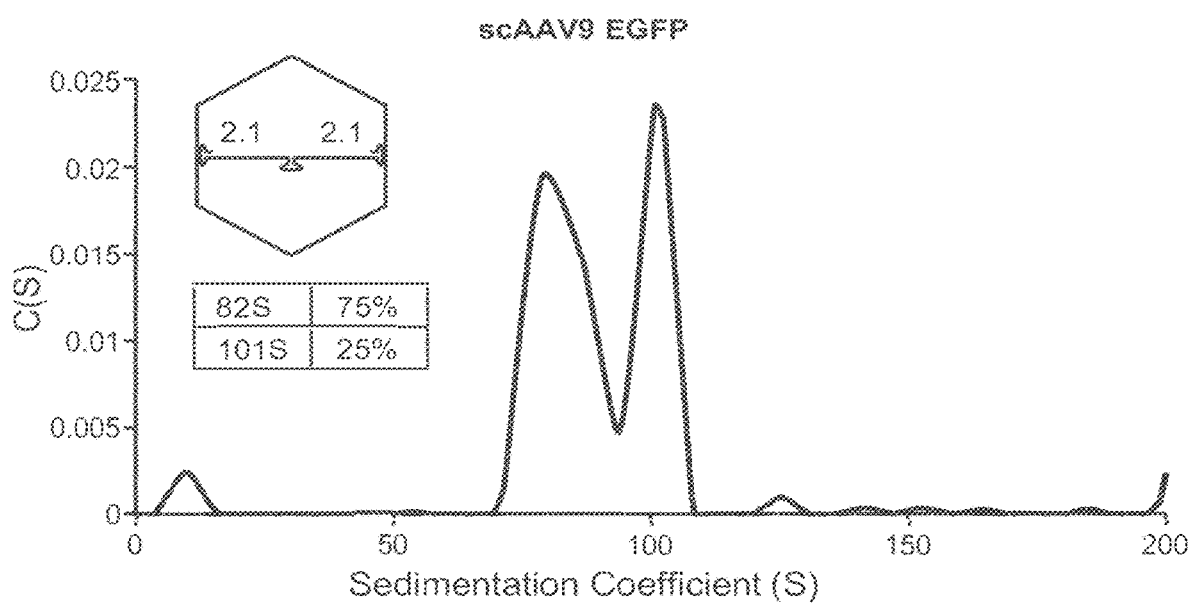
FIGS. 9A, 9B and 9C show that assessment of capsid genome size using AUC data correlates with assessment of genome size by Southern blot.

To demonstrate the utility of AUC to detect genome fragments, a self-complementary vector comprising AAV2 ITRS, a minimal CBA promoter, and an EGFP transgene was packaged into an AAV9 capsid (AAV2/9minCBAE-GFP; see schematic in FIG. 9A). The vector particles were purified to eliminate empty capsids and analyzed by AUC. The standard curve was then used to assign genome size to each of the resolved genome containing capsids. Approximately 25% of the vector prep sedimented as a 101 S species, representing an encapsidated genome of ~4.3 kb (FIG. 9A). This 101 S peak represented the double stranded dimeric vector genome, which has a predicted size of ~4.3 kb. However, the majority of the vector prep (75%), sedimented with an S value of 82, which corresponds to a vector genome size of ~2 kb (FIG. 9A), consistent with packaging of the single stranded monomer. The packaging of monomeric genomes with self-complementary vectors is well documented and is often a result of inadvertent terminal resolution at spurious "trs like" sequences despite the presence of an ITR with a mutated D sequence (McCarty et al. (2001) *Gene Ther.*, 8:1248-54).

Figure 9B:
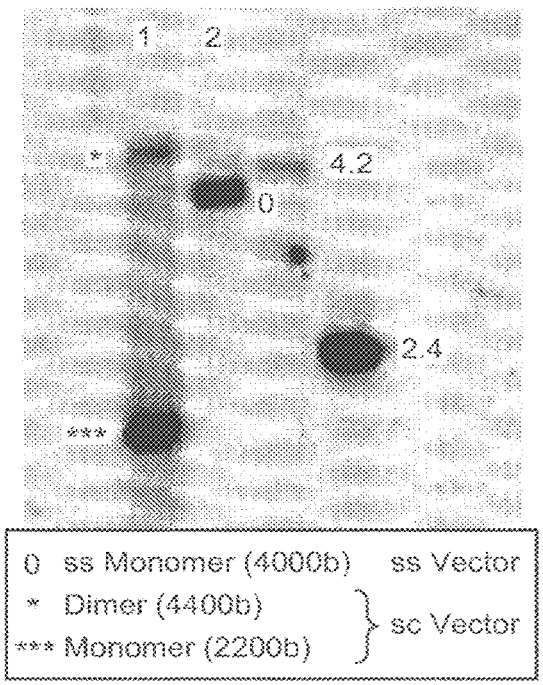
Figure 9C:
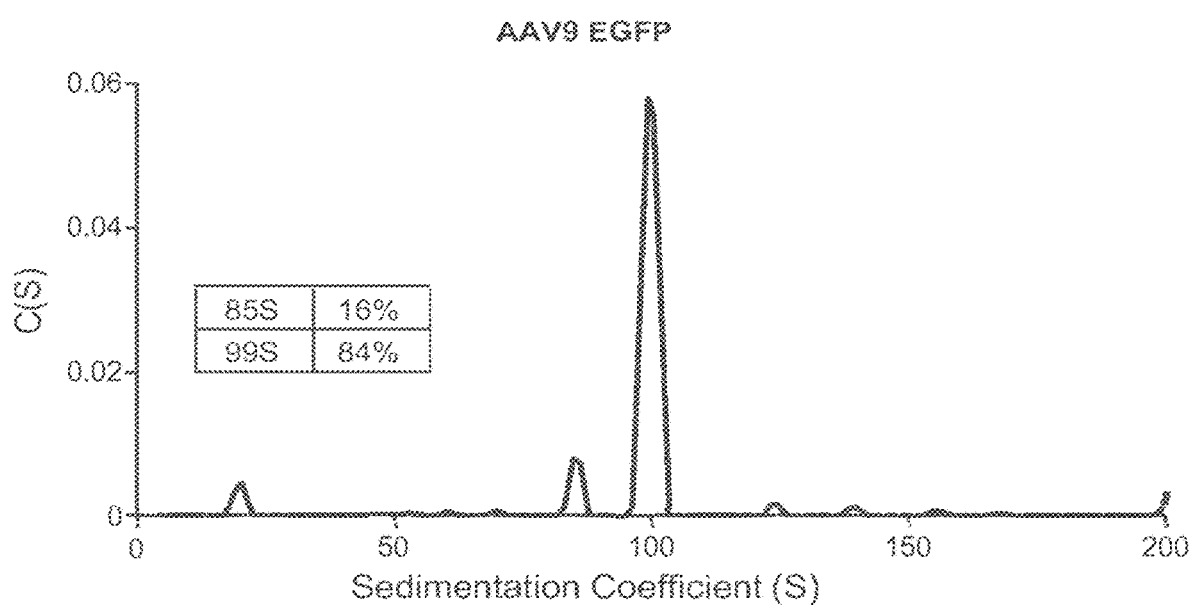

FIG. 9B shows an alkaline Southern blot of the same vector, scAAV9 EGFP, which revealed two vector populations with genomes 4.3 kb and ~2 kb in size, corroborating the AUC data in FIG. 9A. The Southern blot also confirmed that the monomeric viral genome was preferentially packaged over the dimeric genome. Interestingly, AUC analysis of a single stranded AAV9 EGFP vector (~4 kb) revealed a single predominant peak with a measured S value of 99 S, corresponding to approximately 4.1 kb by the standard curve and 84% of capsid abundance (FIG. 9C). These results suggest that single stranded AAV vectors may be packaged in a more homogeneous manner than double stranded vectors. Again, in agreement with the AUC method, Southern blot analysis of this vector prep revealed homogeneous encapsidation of a viral genome of the predicted size of ~4 kb (lane 2, FIG. 9B). These results demonstrate that the AUC method may be used to measure the size of AAV vector genomes, yielding genome size data in agreement with the standard Southern blotting technique. Using the AUC method, single stranded AAV vectors were found to produce more homogeneous vector preparations than double stranded ones. These results show that the AUC method is a powerful tool to identify and quantify capsid species with incomplete genomes from vector preparations.

Example 6: Use of AUC to Assess Factors that Influence Packaging of Vector Genomes The AUC method was next used as a tool to identify factors that influence the packaging of intact AAV vector genomes.

Figure 10A:
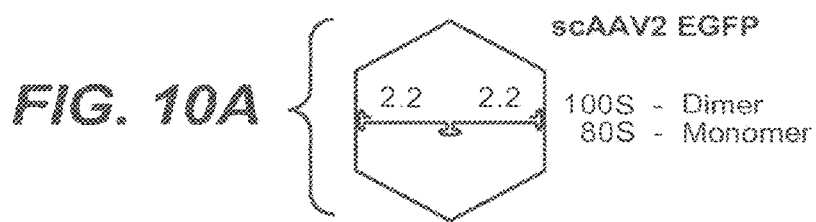
FIGS. 10A, 10B and 10C show that the Rep/Cap promoter position affects genome packaging in recombinant viral vectors produced by the triple transfection method.

As discussed in Example 3, the production of rAAV vectors by transient transfection methods requires the use of three plasmids including a rep/cap helper, an ITR vector plasmid, and a pAd helper (see FIG. 4). AUC was used to assess the effect of the rep/cap helper on vector genome packaging for both single stranded and self-complementary AAV vectors. First, a self-complementary AAV vector harboring an EGFP transgene (FIG. 10A) was produced using one of two methods. In the first method (FIG. 10B), a helper plasmid was used in which rep 78/68 expression was driven by the endogenous p5 promoter ("WT Rep" construct). In the second method (FIG. 10C), the helper was modified such that 78/68 expression was reduced by moving the p5 promoter downstream of the cap2 sequence as well as mutating the TATA box ("pHLP Rep" construct). The full scAAV2 EFGP capsid was predicted to have a sedimentation coefficient of 100 S in dimeric genome form and 80 S in monomeric genome form (FIG. 10A).

Figure 10B:
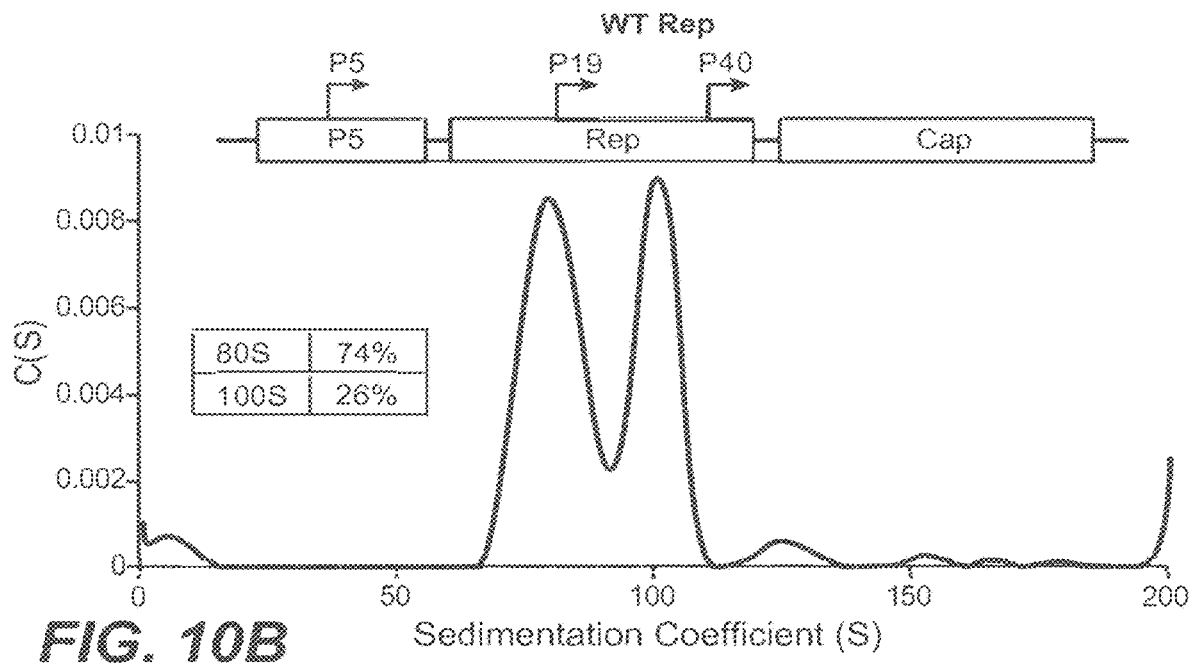
Figure 10C:
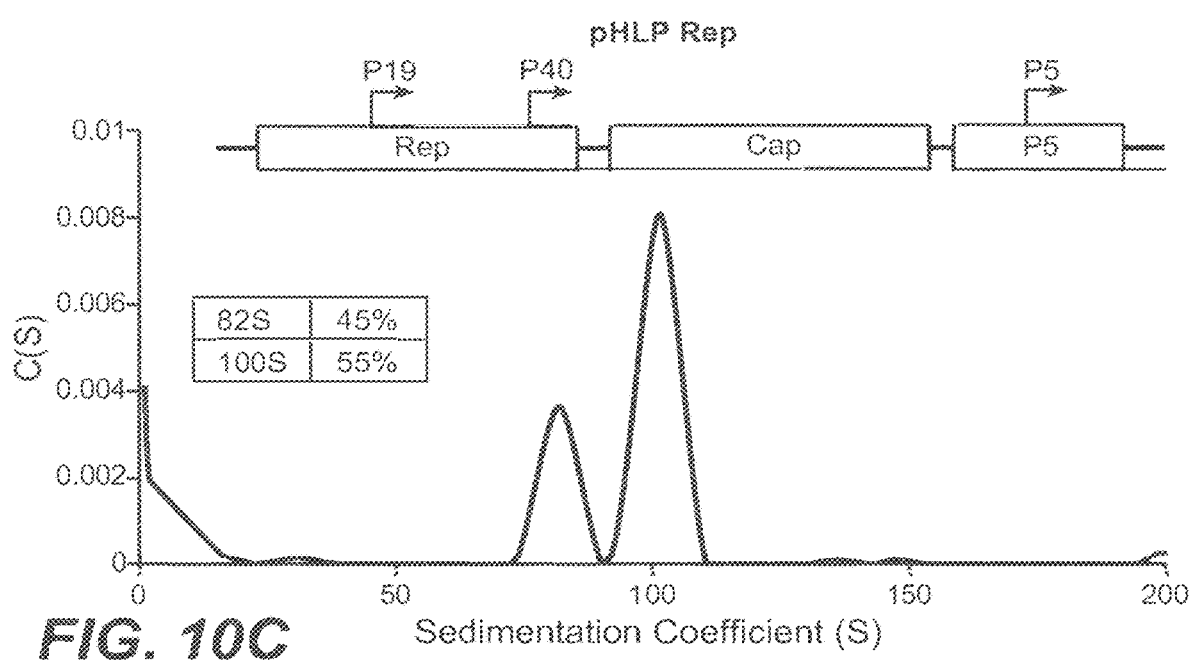

AUC analysis of these scAAV2EGFP vector preps revealed a significant difference in vector genome packaging. In the presence of reduced rep78/68 (pHLP), more than half (55%) of the vector prep contained dimeric genomes, represented by the 100 S species (FIG. 10C). This was the expected sedimentation coefficient for a capsid containing a dimeric genome of 4.4 kb. In contrast, the scAAV2EGFP prep generated with the full complement of rep78/68 had significantly less packaged dimeric genomes (26%), with the majority of the capsids containing monomeric genomes and sedimenting at 80 S (FIG. 10B). These results uncovered a significant difference in genome packaging induced by shifting the P5 promoter of the helper plasmid, leading to reduced rep 78/68 protein levels.

Figure 11A:
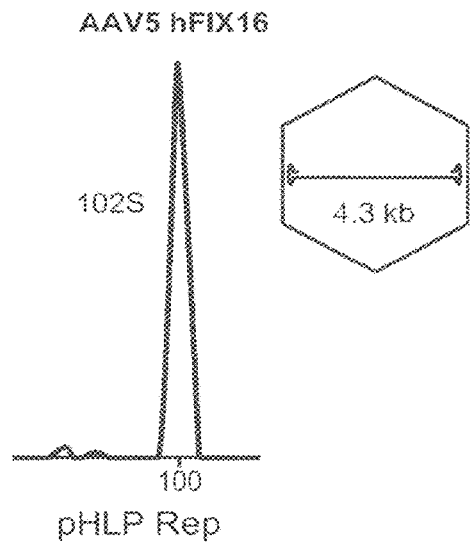
FIGS. 11A, 11B, 11C and 11D show that the Rep/Cap promoter position affects genome packaging in two additional AAV vectors.
Figure 11B:
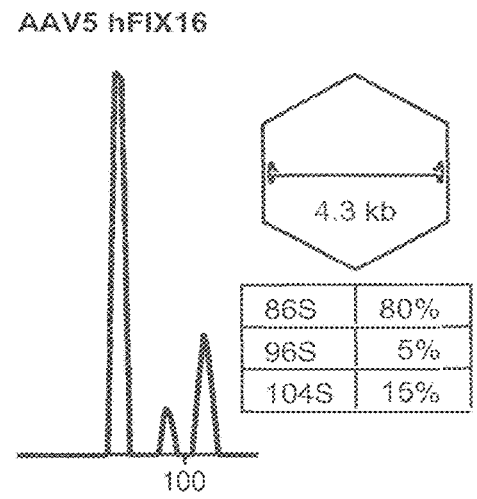

A single stranded AAV5 Factor IX vector, AAV5FIX, (FIGS. 11A-B) and a single stranded AAV5hSMN vector (FIG. 11C-D) were generated using rep/cap helpers that differed in rep expression as described above, but cap sequences of AAV2 were replaced by cap sequences of AAV5. Based on the nucleotide size of the FIX expression cassette (4.3 kb), the predicted sedimentation coefficient for the AAV5 FIX vector capsid was approximately 101 S. AUC analysis of AAV2/5FIX made in the presence of reduced rep78/68 ("pHLP19 Rep") revealed a homogenous profile with the majority of the vector (90%) sedimenting with an S value of the expected size, ~101 S (FIG. 11A). In contrast, AAV5 FIX vector generated using a rep/cap5 helper expressing wild-type levels of rep 78/68 proteins ("WT Rep") generated a strikingly different AUC profile (FIG. 11B). Instead of a predominant peak at 101 S, this profile revealed more capsid heterogeneity, with the majority of the AAV5 FIX (80%) sedimenting at a lower S value of 86 S, likely representing packaging of a fragmented genome. Moreover, in this vector sample only 15% of the AAV5 FIX vector capsids sedimented at the correct S value of ~104 S (FIG. 11B).

Figure 11C:
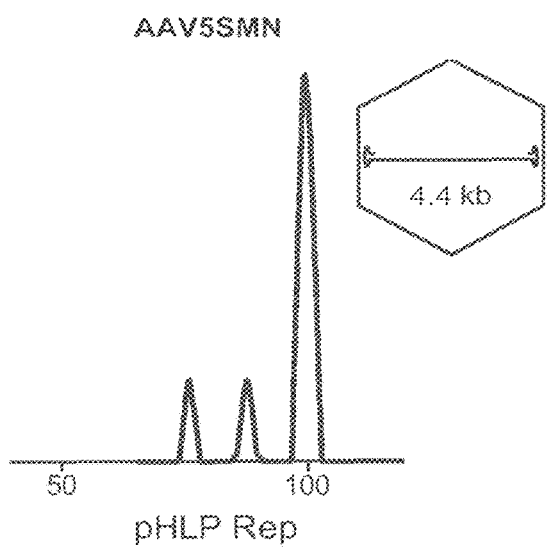
Figure 11D:
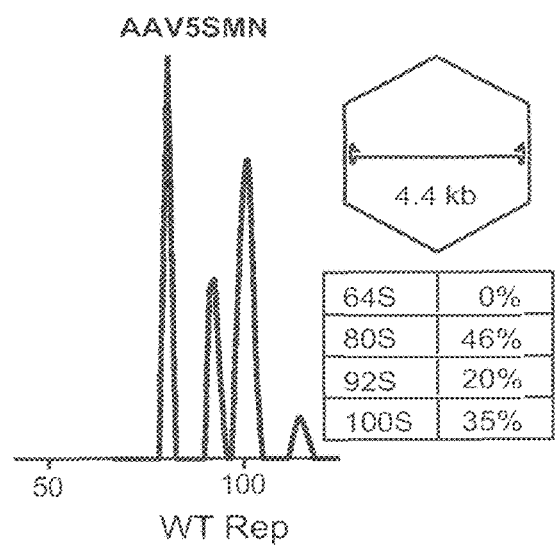

AAV5 SMN vectors made using these same wild-type and mutated p5 rep/cap helpers also had strikingly different AUC profiles. As seen with the single stranded AAV5FIX vectors, AAV5 SMN vectors generated in the presence of reduced rep78/68 showed less heterogeneity by AUC analysis, with a single capsid species sedimenting at the S value of 101 S, consistent with packaging of a genome of the predicted size of ~4.4 kb (FIG. 11C). In contrast, the AUC profile for the same vector genome packaged using "wild-type" levels of rep78/68 protein revealed three distinct AAV vector species, with sedimentation coefficients of 100 S (predicted S value for the full vector genome of 4400 nt), 92 S (representing a fragmented genome of approximately 3300 nt) and 80 S (representing a fragmented genome of 2000 nucleotides) (FIG. 11D). These results confirm a significant difference in genome packaging induced by shifting the P5 promoter of the helper plasmid using two additional AAV vectors.

Figure 12A:
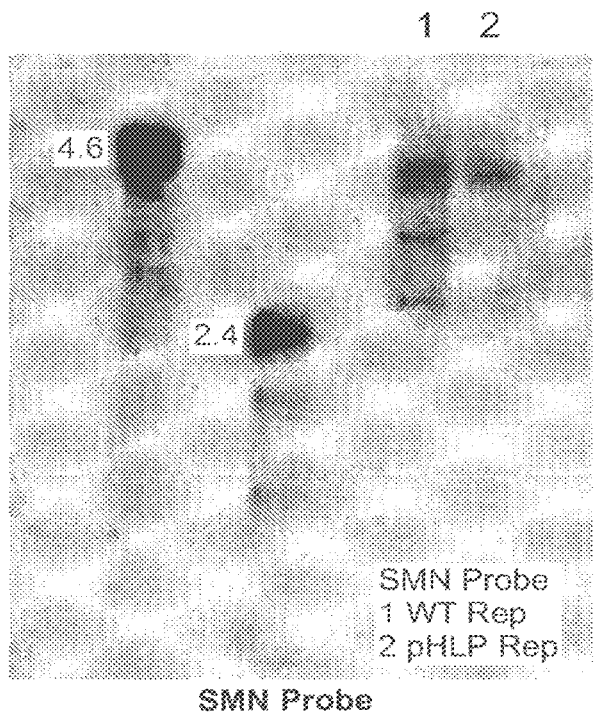
FIGS. 12A and 12B reveal that Southern blot analysis correlates with AUC analysis but misses some fragmented genomes detectable by AUC.
Figure 12B:
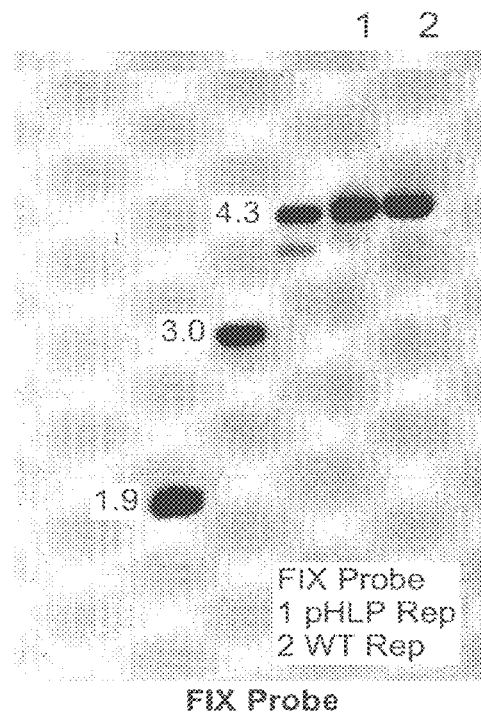

Further analysis of the AAV5SMN and AAV5FIX vector preps was performed by Southern blot analysis of vector DNA. In agreement with the AUC method, Southern blot analysis of AAV5SMN generated with wild-type rep78/68 protein levels revealed packaging of full length (4.4 kb) and fragmented (less than 4.4 kb) SMN genomes (FIG. 12A, lane 1). In contrast, the AAV5SMN vector generated in the presence of reduced rep78/68 protein contained largely capsids with a full length SMN genome (FIG. 12A, lane 2). Interestingly, a comparison of the two AAV5FIX vector preps by Southern analysis revealed the presence of a FIX full length genome even when vector was produced in the presence of wild-type levels of rep 78/68 (FIG. 12B, lane 2). However, AUC analysis of this AAV5FIX vector (FIG. 11B) showed that 80% of the capsids contained a fragmented genome (~3000 nucleotides), which were undetected by the FIX probe.

Figure 13:
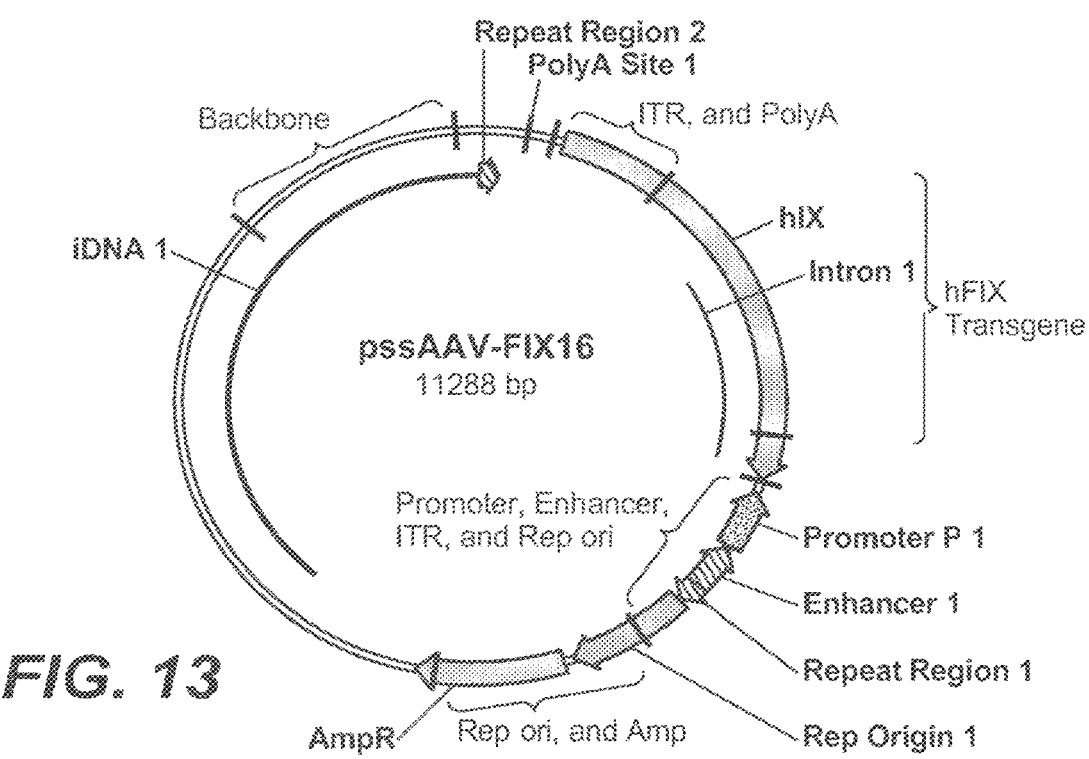
FIG. 13 provides a map of the AAV5 Factor IX vector indicating the positions of the hFIX transgene, ITR, Rep origin, and AmpR marker gene, among other features. Note that the AmpR marker is upstream of the ITR, enhancer, and promoter region.
Figure 14A:
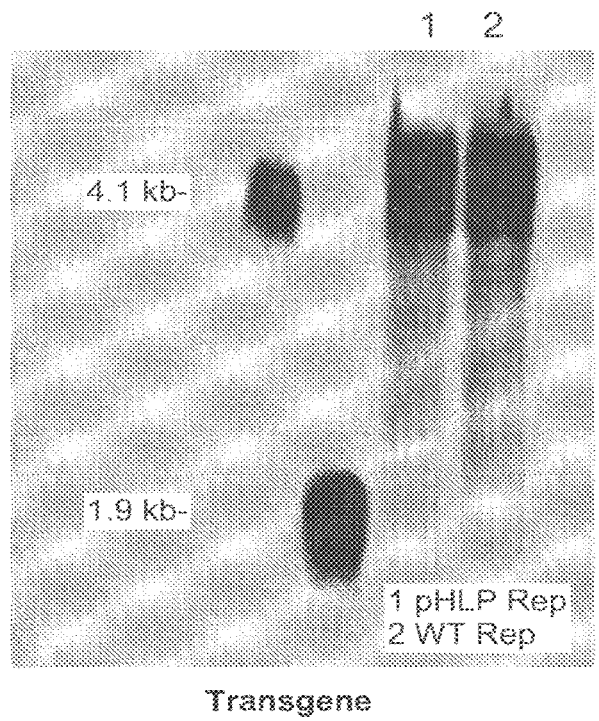
FIGS. 14A and 14B show that WT Rep vector genomes, unlike pHLP Rep vector genomes, package sequences upstream of the 5' ITR in the AAV5 Factor IX vector.
Figure 14B:
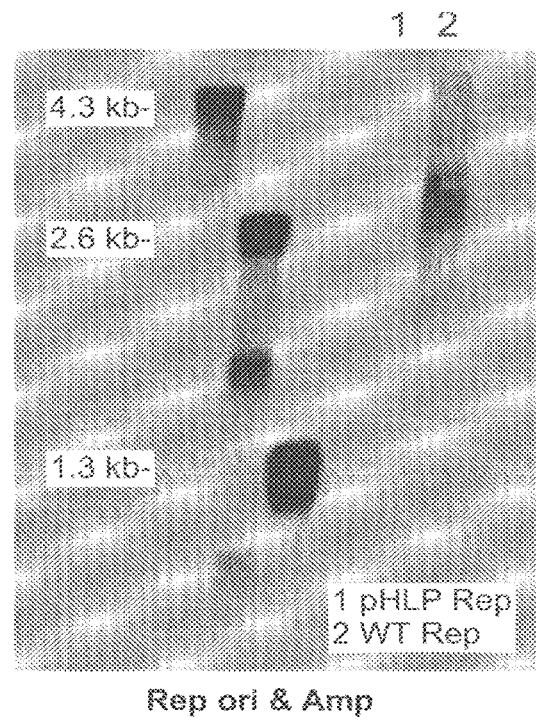

Further analysis of the FIX vector preps generated under the two experimental conditions was performed by generating probes to discrete regions of the vector plasmid, including regions of the backbone. A map of this vector is provided in FIG. 13. FIG. 14 shows Southern blotting analyses using these probes to compare these FIX vector preps generated under different conditions. As shown in FIG. 14A, both vector preparations (pHLP rep, lane 1; WT rep, lane 2) contained the hFIX transgene. However, FIG. 14B lane 2 confirms that the vector genome species sedimenting at 86 S observed in the WT Rep preparation (FIG. 11B) was a ~3 kb fragment. Moreover, this species reacted with an $Amp^R$ specific probe (FIG. 14B, lane 2), suggesting that packaging upstream of the 5'ITR had occurred in a rep dependent manner. In contrast, there was no evidence of an $Amp^R$ containing fragment in the rAAV5 FIX vector preps that were generated in the presence of reduced levels of rep 68/78 (FIG. 14B, lane 1).

DNA impurities in the AAV FIX preps were also assessed by Q-PCR using primers and probes specific for $Amp^R$. By Q-PCR, approximately 35% $Amp^R$ titer was detected in AAV5FIX vector preps generated in the presence of "wt" rep, in contrast to less than 1% when the same vector plasmid was used to generate AAV5FIX vector in the presence of reduced rep68/78 (data not shown). These results underscore the utility of AUC analysis for revealing the presence of packaged genomes that would otherwise go undetected by gene specific Southern blot analysis.

The packaging capacity of AAV vectors has been studied extensively, and although numerous reports have demonstrated successful transduction with vectors packaging oversized AAV genomes, the latter have been shown to be fragmented into subgenomic-length DNA. To further explore the applicability of the AUC method, the heterogeneity of AAV vectors produced using oversized genomes was evaluated. An expression cassette harboring the full length CBA promoter driving expression of the β-phosphodiesterase transgene was packaged as an oversized genome of 5.4 kb (FIG. 15A) or as a wild type size genome of 4.6 kb (FIG. 15B). To generate the 4.6 kb genome, the CBA promoter was truncated by reducing the size of the intron as previously reported (Gray, S J et al., (2011) *Hum. Gene Ther.* 22(9):1143-1153).

Figure 15A:
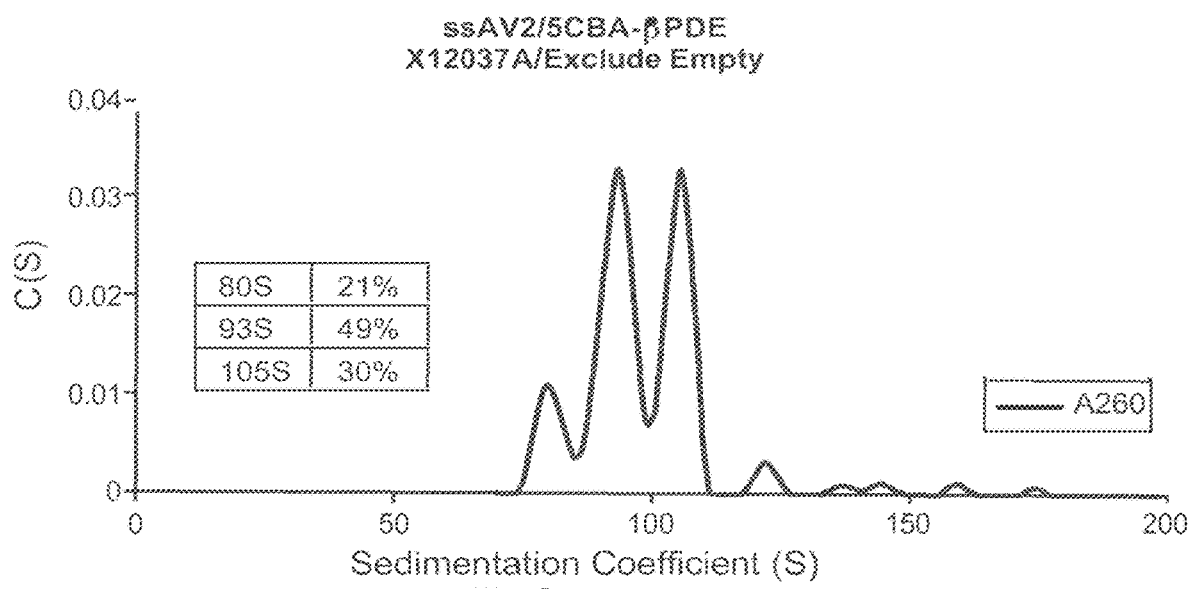
FIGS. 15A and 15B show the fragmentation of oversized AAV vector genomes, as demonstrated by AUC analysis.
Figure 15B:
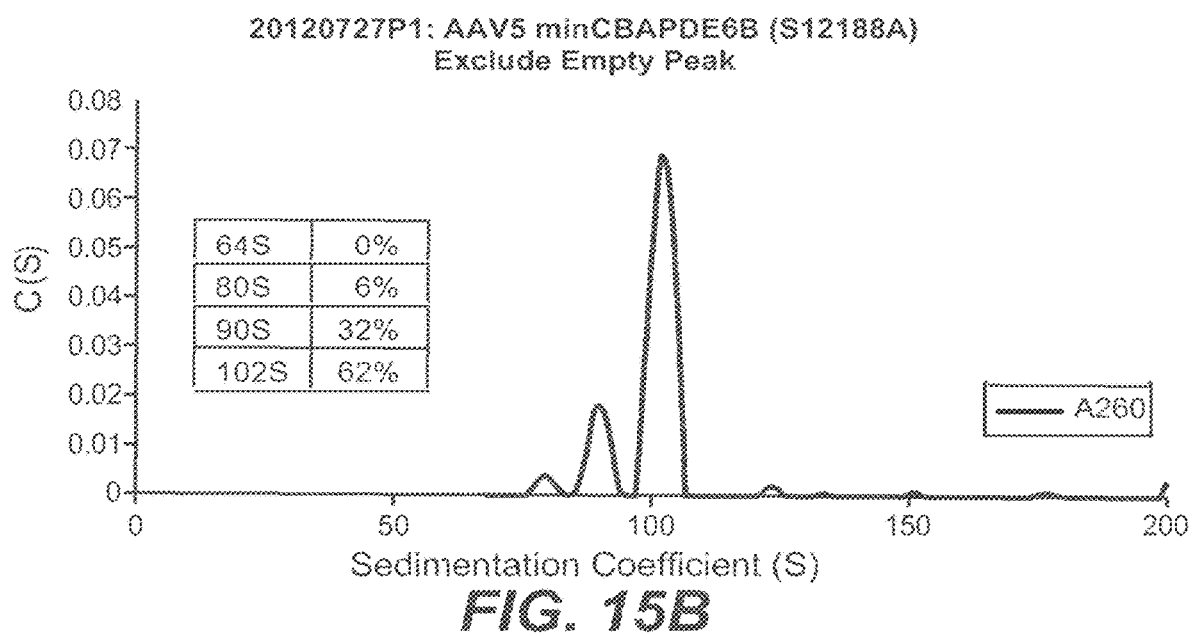

As shown in FIG. 15A, the AUC profile of the AAV vector prep generated using the oversized vector genome demonstrated that nearly half of the vector prep sedimented as a 93 S species, consistent with packaging a fragmented vector genome of approximately 3.5 kb. 30% of the preparation was represented by another sub-genomic vector species of approximately 4.9 kb sedimenting at 105 S. There was no evidence of packaging of a full-length 5.4 kb genome, which was predicted to sediment at 108-109 S. In contrast, AUC analysis revealed that the same transgene under control of the abbreviated CBA promoter sedimented predominantly as a vector species of 102 S, consistent with packaging of the predicted, full-length vector genome of 4.6 kb (FIG. 15B). These results demonstrate the utility of AUC analysis in profiling AAV vectors with oversized genomes, and this profiling is critical, given the observed incidence of genome fragmentation.

This example demonstrated that the AUC method is highly effective in analyzing the genome size of AAV vector capsids in a heterogeneous preparation. By resolving genome-containing capsids by size (e.g., dimeric and monomeric genomes, or partial fragments thereof), the AUC method represents a powerful tool for assaying the quality of AAV vector preps produced under different conditions. Moreover, the results from three distinct vector systems demonstrated that the AUC method is widely useful for quality control and optimization of conditions to yield improved AAV vector preparations. Importantly, the AUC method is able to detect fragmented genomes that are not detectable by Southern blot analysis. Whereas Southern blotting relies on the presence of DNA probe sequence for detection, the AUC method is sequence-independent. The AUC method has also been demonstrated to be an effective tool in analyzing oversized AAV genomes. In total, these results demonstrate the highly advantageous and effective implementation of AUC methods to analyze multiple types of AAV vector preparations, which have been found to display dramatically variable effects on genome packaging.

Example 7: Characterization of Recombinant Adenoviral Vector Preparations by Analytical Ultracentrifugation Adenovirus (Ad) vectors have features that make them attractive as vectors for gene therapy. The generation of Ad vector products requires an analytical method that monitors product quality with regard to homogeneity, purity, and consistency of manufacturing. To meet this demand, the potential use of analytical ultracentrifugation (AUC) as a technique to characterize the homogeneity of Ad vectors was investigated.

Methods

Sample Preparation

In order to support accurate AUC assessment, a recombinant adenovirus serotype 2 vector (Ad2) was prepared and highly purified ty CsCl gradient ultrafiltration to enrich for genome containing particles. Product concentration was determined by optical density measurement at 260 nm ($OD_{260}$) by spectrophotometric methods. To generate reproducible and consistent AUC data, sample adjustments were made to target concentration by optical density measurement at 260 nm from 0.1 to 1.0, either by direct dilution with PBS or further concentration using Amicon Ultra-0.5/30K MWCO Centrifugal Filter Device.

Sedimentation Velocity AUC Data Acquisition

Sedimentation velocity analytical ultracentrifugation (SV-AUC) analysis was performed using a ProteomeLab™ XL-I (Beckman Coulter). 400 μL sample was loaded into the sample sector of a two sector velocity cell, and 400 μL PBS was loaded into the corresponding reference sector. The sample was placed in the four-hole rotor and allowed to equilibrate in the instrument until a temperature of 20° C. and full vacuum were maintained for one hour. Sedimentation velocity centrifugation was performed at 6,000 RPM, 20° C., 0.003 cm radial step setting, with no delay and with no replicates. Raleigh interference optics were used to simultaneously record radial concentration as a function of time until the smallest sedimenting component cleared the optical window (1.2 hour). Assay throughput was limited to a single sample per run based on absorbance scan collection times of greater than one minute, as well as the large size and rapid sedimentation of Ad2.

AUC Data Analysis

The percent full capsid was determined by analyzing approximately 75 scans from interference detection method using the SEDFIT (NIH/see worldwide web at analyticalultracentrifugation.com) continuous size C(S) distribution model. Second ($2^{nd}$) derivative regularization was applied to the fitting with a confidence level of F statistic/ratio=0.68. The following C(S) parameters were held constant: resolution=2505, S min=10, S max=1500 and frictional ratio=1.86935. RI and TI noise subtractions were applied, and the meniscus position was allowed to float, letting the software choose the optimal position. This model fit the data to the Lamm equation, and the resulting size distribution was a "distribution of sedimentation coefficients" that looked like a chromatogram with the area under each peak proportional to concentration in units of Fringes or $OD_{260}$ units. The sedimentation coefficient (in Svedberg units) and the relative concentration (in OD units) were determined for each component in the distribution. Each AUC run was an independent assay, and each analysis was monitored for the following attributes to ensure quality of results: goodness of fit (rmsd), the ratio of $OD_{260\,nm}$/interference signal in fringes (A260/IF ratio) for each peak, consistency of sedimentation coefficients for each species between runs, and overall quality of the scans. The rmsd of this representative example was 0.006584.

Results

Figure 16:
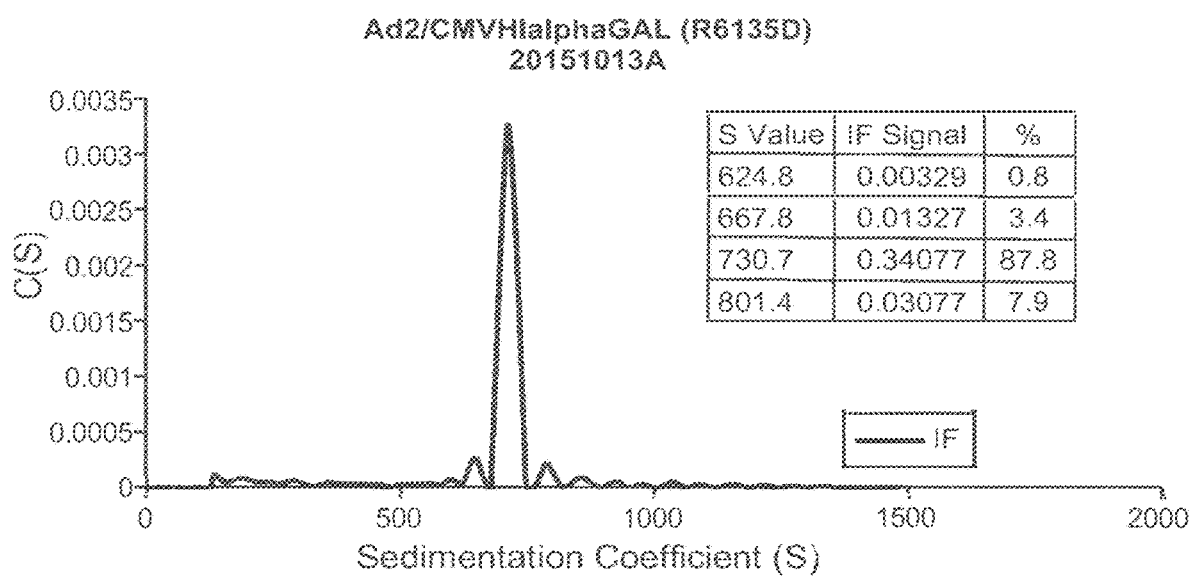
FIG. 16 shows the AUC profiles of pure populations of adenovirus capsids. The sedimentation coefficient (S) and interference values are given for each peak.

Analytical ultracentrifugation (AUC) using classical boundary sedimentation velocity was used to reveal the particle heterogeneities of recombinant adenovirus serotype 2 vectdor (rAd2) vector preps. To monitor the movement of rAd2 particles in response to a centrifugal force, this mixture of rAd2 capsids was scanned using interference optics along a centrifugal field at defined time intervals. Scans represented the acquisition of concentration data as a function of radius r, at times t, to yield a series of concentration scans that revealed the complete migration pattern of constituent vector particles in the rAd2 vector prep. Plotting the differential sedimentation coefficient distribution value, C(S), versus the sedimentation coefficient (in Svedberg units, S) yielded distinct peaks with unique sedimentation coefficients rAd2 species (FIG. 16). The C(S) values were determined using the SEDFIT algorithm described by Schuck (2000) *Biophys.* 1, 78:1606-19.

For the rAd2 vector prep shown in FIG. 16, 87.8% of the rAd2 vector preparation sedimented with an S value of 731, consistent with a vector preparation consisting predominantly of genome containing capsids. These data confirm that adenoviral particles can be resolved by AUC.

What is claimed is:

1. A method of quantifying one or more species of individual variant viral particles comprising fragmented recombinant adeno-associated viral (rAAV) genomes in a heterogeneous mixture of viral particles, said method comprising:
   (i) subjecting the heterogeneous mixture of viral particles to analytical ultracentrifugation under boundary sedimentation velocity conditions to generate sedimenting boundaries, wherein the boundary sedimentation velocity is from about 3,000 rpm to about 20,000 rpm;
   (ii) measuring the rate of movement or migration of the sedimenting boundaries, wherein movement or migration of each species of individual viral particles in the heterogeneous mixture of viral particles results in distinct sedimenting boundaries, each distinct sedimenting boundary corresponding to a resolvable species of viral particle, and wherein the individual viral particles comprise empty particles without genome, particles with full genomes and particles with fragmented genomes;
   (iii) determining the genome size of one or more species of the individual variant viral particles in the heterogeneous mixture of viral particles; and
   (iv) determining the quantity of one or more species of the variant viral particles in the heterogeneous mixture of viral particles.

2. The method of claim 1, wherein each species of the individual variant viral particles in a heterogeneous mixture of viral particles is fully resolved.

3. The method of claim 1, wherein determining the genome size of one or more species of the individual variant viral particles in the heterogeneous mixture of viral particles comprises comparing the sedimentation coefficients of the variant viral particles with a standard curve generated by sedimentation coefficients of viral particles comprising recombinant AAV genomes of known nucleotide sizes.

4. The method of claim 1, wherein the boundary sedimentation velocity is from about 10,000 rpm to about 20,000 rpm.

5. The method of claim 3, wherein the boundary sedimentation velocity is from about 10,000 rpm to about 20,000 rpm.

6. The method of claim 1, wherein the boundary sedimentation velocity is from about 15,000 rpm to about 20,000 rpm.

7. The method of claim 3, wherein the boundary sedimentation velocity is from about 15,000 rpm to about 20,000 rpm.

8. The method of claim 1, wherein the boundary sedimentation is performed at a temperature of about 4° C.

9. The method of claim 3, wherein the boundary sedimentation is performed at a temperature of about 4° C.

10. The method of claim 1, wherein the fragmented genomes are sub-genomic DNA molecules.

11. The method of claim 3, wherein the fragmented genomes are sub-genomic DNA molecules.

12. The method of claim 1, wherein the AUC is run from about 0.5 hours to about 2 hours.

13. The method of claim 3, wherein the AUC is run from about 0.5 hours to about 2 hours.

14. The method of claim 12, wherein the AUC is run from about 1 hours to about 2 hours.

15. The method of claim 13, wherein the AUC is run from about 1 hours to about 2 hours.

16. The method of claim 1, wherein the AUC is run in an ultracentrifuge velocity cells with two sectors in dialysis equilibrium, wherein each sector comprises an optical window.

17. The method of claim 3, wherein the AUC is run in an ultracentrifuge velocity cells with two sectors in dialysis equilibrium, wherein each sector comprises an optical window.

18. The method of claim 16, wherein the AUC is run until the lightest sedimenting component clears the optical window.

19. The method of claim 17, wherein the AUC is run until the lightest sedimenting component clears the optical window.

20. The method of claim 1, wherein the total concentration of viral particles in the heterogeneous mixture of viral particles prior to step (i) is greater than $5 \times 10^{11}$ vg/mL.

21. The method of claim 3, wherein the total concentration of viral particles in the heterogeneous mixture of viral particles prior to step (i) is greater than $5 \times 10^{11}$ vg/mL.

22. The method of claim 1, wherein the total concentration of viral particles in the heterogeneous mixture of viral particles AAV vector preparation prior to step (i) is from about $1 \times 10^{11}$ vg/mL to about $1 \times 10^{13}$ vg/mL.

23. The method of claim 3, wherein the total concentration of viral particles in the heterogeneous mixture of viral particles AAV vector preparation prior to step (i) is from about $1 \times 10^{11}$ vg/mL to about $1 \times 10^{13}$ vg/mL.

24. The method of claim 1, wherein the heterogeneous mixture of viral particles comprises viral particles comprising AAV9 capsid proteins.

25. The method of claim 24, wherein the viral particles comprising AAV9 capsid proteins further comprise at least one AAV2 ITR.

26. The method of claim 24, wherein the heterogeneous mixture of viral particles preparation comprise viral particles encapsidating self-complementary AAV viral genomes.

27. The method of claim 3, wherein the heterogeneous mixture of viral particles comprises viral particles comprising AAV9 capsid proteins.

28. The method of claim 27, wherein the viral particles comprising AAV9 capsid proteins further comprise at least one AAV2 ITR.

29. The method of claim 27, wherein the heterogeneous mixture of viral particles preparation comprise viral particles encapsidating self-complementary AAV viral genomes.

30. The method of claim 1, further comprising determining the relative percentage of each species of the individual viral particles in the heterogeneous mixture of viral particles.

* * * * *